United States Patent
Barbagli et al.

(10) Patent No.: US 8,285,364 B2
(45) Date of Patent: Oct. 9, 2012

(54) SYSTEMS AND METHODS FOR THREE-DIMENSIONAL ULTRASOUND MAPPING

(75) Inventors: Federico Barbagli, San Francisco, CA (US); Aditya Koolwal, Potomac, MD (US); Christopher R. Carlson, Menlo Park, CA (US); Daniel T. Wallace, Santa Cruz, CA (US); Robert G. Younge, Portola Valley, CA (US)

(73) Assignee: Hansen Medical, Inc., Mountain View, CA (US)

( * ) Notice: Subject to any disclaimer, the term of this patent is extended or adjusted under 35 U.S.C. 154(b) by 0 days.

(21) Appl. No.: 13/274,141

(22) Filed: Oct. 14, 2011

(65) Prior Publication Data

US 2012/0035481 A1 Feb. 9, 2012

Related U.S. Application Data

(63) Continuation of application No. 11/906,746, filed on Oct. 2, 2007, now Pat. No. 8,041,413.

(60) Provisional application No. 60/849,049, filed on Oct. 2, 2006, provisional application No. 60/873,901, filed on Dec. 8, 2006, provisional application No. 60/934,688, filed on Jun. 15, 2007, provisional application No. 60/961,189, filed on Jul. 18, 2007, provisional application No. 60/961,191, filed on Jul. 19, 2007.

(51) Int. Cl.
*A61B 5/05* (2006.01)
(52) U.S. Cl. .......................... 600/424; 600/437; 600/459
(58) Field of Classification Search .......... 600/459–471; 604/19, 22, 27; 901/2, 14, 46; 701/300; 702/39, 150
See application file for complete search history.

(56) References Cited

U.S. PATENT DOCUMENTS 5,515,853 A * 5/1996 Smith et al. .................... 600/437
5,622,170 A * 4/1997 Schulz .......................... 600/424
(Continued)

FOREIGN PATENT DOCUMENTS

EP 1005835 A1 6/2000
(Continued)

OTHER PUBLICATIONS

Mun Wai Lee et al., "Particle Filter with Analytical Inference for Human Body Tracking", Proceedings of the Workshop on Motion and Video Computing, Motion '02, IEEE, Nov. 2002 (7 pages).

(Continued)

*Primary Examiner* — Parikha Mehta
(74) *Attorney, Agent, or Firm* — Vista IP Law Group LLP

(57) ABSTRACT

An automated medical system comprises a first instrument assembly including a first ultrasound transducer having a first transducer field of view that transmits and receives ultrasound signals in imaging planes disposed circumferentially about a guide instrument, and a second instrument assembly including a second ultrasound transducer having a second transducer field of view coupled to one of a second flexible guide instrument and a working instrument. A computing system is operatively coupled to the respective first and second transducers and configured to determine a relative spatial orientation of the respective first and second transducers based at least in part on detecting a signal transmitted by one of the first and second transducers and received by the other of the first and second transducers, the received signal having an amplitude indicating the receiving one of the transducers is in the field of view of the transmitting one of the transducers.

7 Claims, 42 Drawing Sheets

U.S. PATENT DOCUMENTS

| | | | |
|---|---|---|---|
| 5,810,008 | A | 9/1998 | Dekel et al. |
| 6,027,451 | A | 2/2000 | McGee et al. |
| 6,106,517 | A | 8/2000 | Zupkas |
| 6,645,195 | B1 | 11/2003 | Bhat et al. |
| 6,799,065 | B1 | 9/2004 | Niemeyer |
| 6,804,547 | B2 | 10/2004 | Pelzer et al. |
| 7,618,371 | B2 | 11/2009 | Younge et al. |
| 7,976,539 | B2 | 7/2011 | Hlavka et al. |
| 8,005,537 | B2 | 8/2011 | Hlavka et al. |
| 2007/0043338 | A1 | 2/2007 | Moll et al. |

FOREIGN PATENT DOCUMENTS

| | | |
|---|---|---|
| WO | 9729709 A1 | 8/1997 |
| WO | 03055133 A1 | 7/2003 |
| WO | 2005087128 A1 | 9/2005 |

OTHER PUBLICATIONS

PCT International Search Report for PCT/US2007/021278, Applicant Hansen Medical, Inc., Forms PCT/ISA/210 and 220, dated Jun. 5, 2008 (6 pages).

PCT Written Opinion of the International Search Authority for PCT/US2007/021278, Applicant Hansen Medical, Inc., Form PCT/ISA/237, dated Jun. 5, 2008 (7 pages).

Communication Pursuant to Article 94(3) EPC for related application in Europe, EP application No. 07839220.6, Applicant Hansen Medical, Inc., dated Aug. 17, 2009, 2 pages.

Reply to communication pursuant to Article 94(3) EPC for related application in Europe, EP application No. 07839220.6, Applicant Hansen Medical, Inc., reply dated Dec. 21, 2009, 15 pages.

Communication Pursuant to Article 94(3) EPC for related application in Europe, EP application No. 07839220.6, Applicant Hansen Medical, Inc., dated Jan. 22, 2010, 4 pages.

Reply to communication pursuant to Article 94(3) EPC for related application in Europe, EP application No. 07839220.6, Applicant Hansen Medical, Inc., reply dated May 31, 2010, 12 pages.

Communication Pursuant to Article 94(3) EPC for related application in Europe, EP application No. 07839220.6, Applicant Hansen Medical, Inc., dated Jun. 23, 2010, 3 pages.

Reply to communication pursuant to Article 94(3) EPC for related application in Europe, EP application No. 07839220.6, Applicant Hansen Medical, Inc., reply dated Jul. 26, 2010, 8 pages.

* cited by examiner

SYSTEMS AND METHODS FOR THREE-DIMENSIONAL ULTRASOUND MAPPING

RELATED APPLICATION DATA

The present application is a continuation of U.S. patent application Ser. No. 11/906,746, filed Oct. 2, 2007, now U.S. Pat. No. 8,041,413, which claims the benefit under 35 U.S.C. §119 to U.S. Provisional Patent Application Ser. No. 60/849,049, filed on Oct. 2, 2006; U.S. Provisional Application Ser. No. 60/873,901, filed on Dec. 8, 2006; U.S. Provisional Patent Application Ser. No. 60/934,688, filed on Jun. 15, 2007; U.S. Provisional Application Ser. No. 60/961,189, filed on Jul. 18, 2007; and U.S. Provisional Patent Application Ser. No. 60/961,191, filed on Jul. 19, 2007. The foregoing applications are all incorporated by reference into the present application in their entirety for all purposes.

FIELD OF INVENTION

The invention relates generally to systems and methods for ultrasound imaging, and, more particularly, to systems and methods for producing three-dimensional maps or models of body cavities or organs for minimally invasive surgery.

BACKGROUND

Limited physical and visual access to internal tissues and organs are typical challenges for performing minimally invasive surgery (MIS), as opposed to conventional surgical procedures wherein a patient's body cavity is opened to permit easier access. To advance the art of minimally invasive surgery, there is a need to overcome the limitations of access to internal tissues and organs; in particular, the limitation of visual access to the tissues and organs that are being diagnosed and treated.

SUMMARY OF THE INVENTION

In one embodiment, an automated medical system, comprises a first instrument assembly including a first flexible guide instrument having an interior lumen and a distal end opening, and an ultrasound instrument positioned in and axially movable relative to the first guide instrument lumen. The ultrasound instrument may be extended through the distal end opening of the first guide instrument and is rotatable relative to the first guide instrument such that a first transducer coupled to the ultrasound instrument and having a first transducer field of view can transmit and receive ultrasound signals in imaging planes disposed circumferentially about the guide instrument. The system further comprises a second instrument assembly including a second flexible guide instrument having an interior lumen and a distal end opening, a working instrument positioned in the second guide instrument lumen, and a second transducer having a second transducer field of view coupled to one of the second flexible guide instrument and working instrument. A computing system is operatively coupled to the respective first and second transducers and configured to control and process ultrasound signals transmitted and received by the respective first and second transducers. In particular, the computing system is configured to determine a relative spatial orientation of the respective first and second transducers based at least in part on detecting a signal transmitted by one of the first and second transducers and received by the other of the first and second transducers, the received signal having an amplitude indicating the receiving one of the transducers is in the field of view of the transmitting one of the transducers.

BRIEF DESCRIPTION OF THE DRAWINGS

The present invention will be readily understood by the following detailed description, taken in conjunction with accompanying drawings, illustrating by way of examples the principles of the invention. The drawings illustrate the design and utility of preferred embodiments of the present invention, in which like elements are referred to by like reference symbols or numerals. The objects and elements in the drawings are not necessarily drawn to scale, proportion, or precise positional relationship; instead emphasis is focused on illustrating the principles of the invention.

DETAILED DESCRIPTION OF THE ILLUSTRATED EMBODIMENTS

Figure 1:
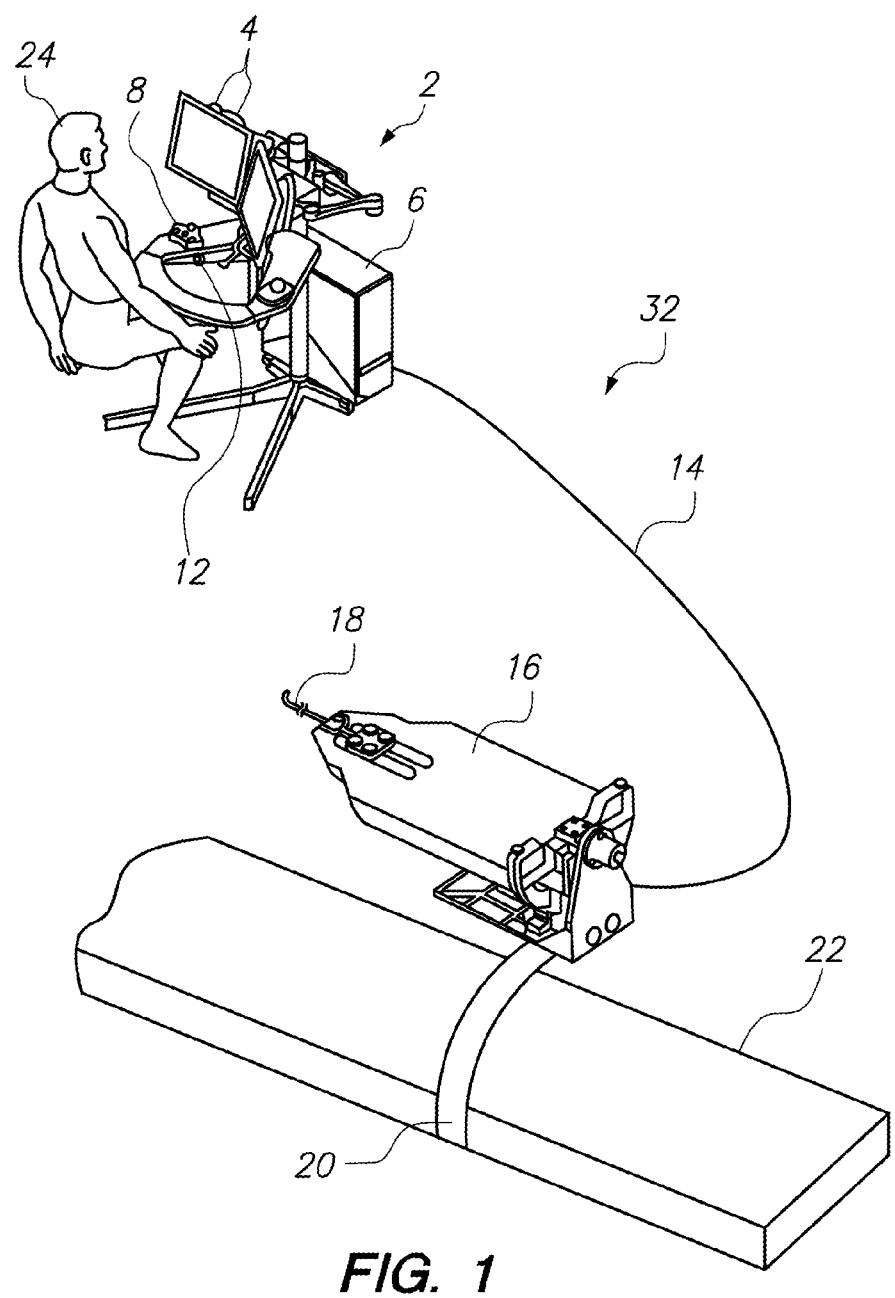
FIG. 1 illustrates one embodiment of a robotic surgical system.

U.S. patent application Ser. No. 10/923,660, filed on Aug. 20, 2004; U.S. patent application Ser. No. 11/185,432, filed on Jul. 19, 2005; U.S. patent application Ser. No. 11/202,925, filed on Aug. 12, 2005; and U.S. patent application Ser. No. 11/481,433, filed on Jul. 3, 2006, are incorporated herein by reference in their entirety.

Reference will now be made in detail to the preferred embodiments of the present invention, examples of which are illustrated in the accompanying drawings. While the invention will be described in conjunction with the preferred embodiments, it will be understood that they are not intended to limit the invention to these embodiments. On the contrary, the invention is intended to cover modifications, alternatives, and equivalents that may be included within the spirit and scope of the invention. Furthermore, in the following detailed description of the embodiments, numerous specific details are set forth in to order to provide a thorough understanding of the present invention. However, it will be readily apparent to one skilled in the art that the present invention may be practiced without these specific details. In other instances, well-known methods, procedures, and components have not been described in detail so as not to unnecessarily obscure aspects of the present invention.

Standard surgical procedures typically involve using a scalpel to create an opening of sufficient size to enable a surgical team to gain access to an area in the body of a patient for the surgical team to diagnose and treat one or more target sites. When possible, minimally invasive surgical procedures may be used instead of standard surgical procedures to minimize physical trauma to the patient and reduce recovery time for the patient to recuperate from the surgical procedures. Minimally invasive surgical procedures typically require using extension tools (e.g., catheters, etc.) to approach and address the target site. The extension tools may be manually operated systems or robotic systems. In some minimally invasive surgical procedures, as those enabled by the Sensei™ Robotic Catheter System from Hansen Medical, Inc. in Mountain View, Calif., U.S.A., the target site is approached through natural pathways (e.g., blood vessels, gastrointestinal tract, etc.) from a remote location either through a natural body orifice or a percutaneous incision. As can be appreciated, the surgeon may have limited access to information or feedback (e.g., visual, tactile, etc.) to accurately navigate the extension tools, such as one or more catheters, and place the working portions of the extension tools at precise locations to perform the necessary diagnostic and/or interventional procedures. Even with such potential limitations, minimally invasive surgical procedures may be more effective and beneficial for treating the patient, instead of standard open surgery.

Minimally invasive diagnostic and interventional operations may require the surgeon to remotely approach and address the operation or target site by using extension tools. The surgeon usually approaches the target site through either a natural body orifice or a small incision in the body of the patient. In some situations, the surgeon may use multiple extension tools and approach the target site through both a natural body orifice as well as a small incision in the body of the patient. Typically, the natural body orifice or small incision is located at some distance away from the target site. Extension tools enter the body through the natural body orifice or small incision, and the extension tools are guided, manipulated, maneuvered, and advanced toward the target site typically by way of natural body pathways (e.g., blood vessels, esophagus, trachea, small intestine, large intestine, urethra, etc.). The extension tools might include one or more catheters and other surgical instruments. The catheters may be manually controlled catheters or robotically operated catheters. In most situations, the surgeon has limited visual and tactile information to discern the location of the catheters and surgical instruments relative to the target site and/or other organs in the patient.

For example, in the treatment of cardiac arrhythmias such as atrial fibrillation (AF), cardiac ablation therapy is applied to the left atrium of the heart to restore normal heart function. For this operation, one or more catheters (e.g., sheath catheter, guide catheter, ablation catheter, etc.) may be inserted through an incision at the femoral vein near the thigh or pelvic region of the patient, which is located at some distance away from the operation or target site. In this example, the operation or target site for performing cardiac ablation is in the left atrium of the heart. Catheters may be guided (e.g., by a guide wire, etc.), manipulated, maneuvered, and advanced toward the target site by way of the femoral vein to the inferior vena cava into the right atrium and through the interatrial septum to the left atrium of the heart. Currently, the surgeon has limited visual and tactile information to assist him or her with maneuvering and controlling the catheters. In particular, because of limited information, it is especially difficult for the surgeon to maneuver and control one or more distal portions of the catheters to perform cardiac ablation at precise locations or spots in the left atrium of the heart. As will be explained below, embodiments of the present invention provide improved visual information to the surgeon to assist him or her with "seeing" the operation site, such that the surgeon may be able to position the catheter more precisely to address the operation or target sites in the patient. For example, with improved visual information, the surgeon may be able to apply cardiac ablation at the desired locations or spots in the left atrium of the heart in a more precise manner to address cardiac arrhythmias such as atrial fibrillation.

Figure 2:
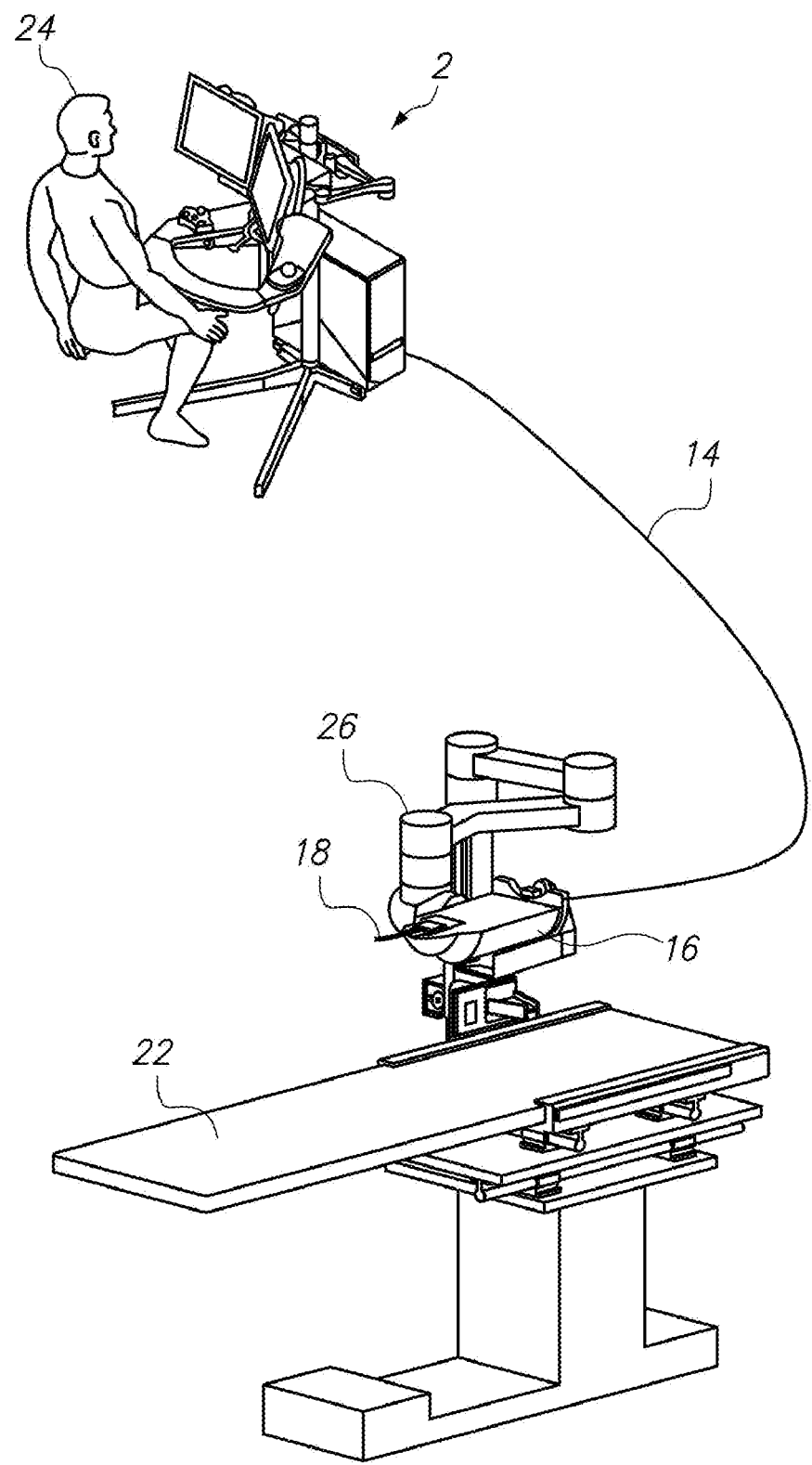
FIG. 2 illustrates another embodiment of a robotic surgical system.

FIG. 1 illustrates one embodiment of a robotic surgical system (32), e.g., the Sensei™ Robotic Catheter System from Hansen Medical, Inc. in Mountain View, Calif., U.S.A., with an operator control station (2) located remotely from an operating table (22) to which an instrument driver (16) and instrument (18), e.g., the Artisan™ Control Catheter also from Hansen Medical, Inc. in Mountain View, Calif., U.S.A., are supported by an instrument driver mounting brace (20). A wired connection (14) transfers signals between an electronics rack (6) at the operator control station (2) and the instrument driver (16). The electronics rack (6) includes system hardware and software that substantially operate and perform the many functions of the robotic surgical system (32). The instrument driver mounting brace (20) is a substantially arcuate-shaped structural member configured to position the instrument driver (16) above a patient (not shown) lying on the operating table (22). The wired connection (14) may transmit manipulation and control commands from an operator or surgeon (24) who is working at the operator control station (2) to the instrument driver (16) to operate the instrument (18) to perform minimally invasive operations on the patient lying on the operating table (22). The wired connection (14) may also transmit information (e.g., visual views, tactile, force feedback, position, orientation, shape, localization, electrocardiogram, etc.) from the instrument (18), patient, and operation site monitors (not shown in this figure) to the operator control station (2) for providing the necessary information to the operator or surgeon (24) to facilitate monitoring of the instrument, patient and target site for performing precise manipulation and control of the instrument (18) during the minimally invasive surgical procedures. The wired connection (14) may be a hard wire connection, such as an electrical wire configured to transmit electrical signals (e.g., digital signals, analog signals, etc.), an optical fiber configured to transmit optical signals, a wireless link configured to transmit various types of signals (e.g., RF signals, microwave signals, etc.), etc., or any combinations of electrical wire, optical fiber, wireless link, etc. The information or feedback may be displayed on one or more monitors (4) at the operator control station (2). FIG. 2 illustrates another embodiment of a robotic surgical system (32).

Figure 3:
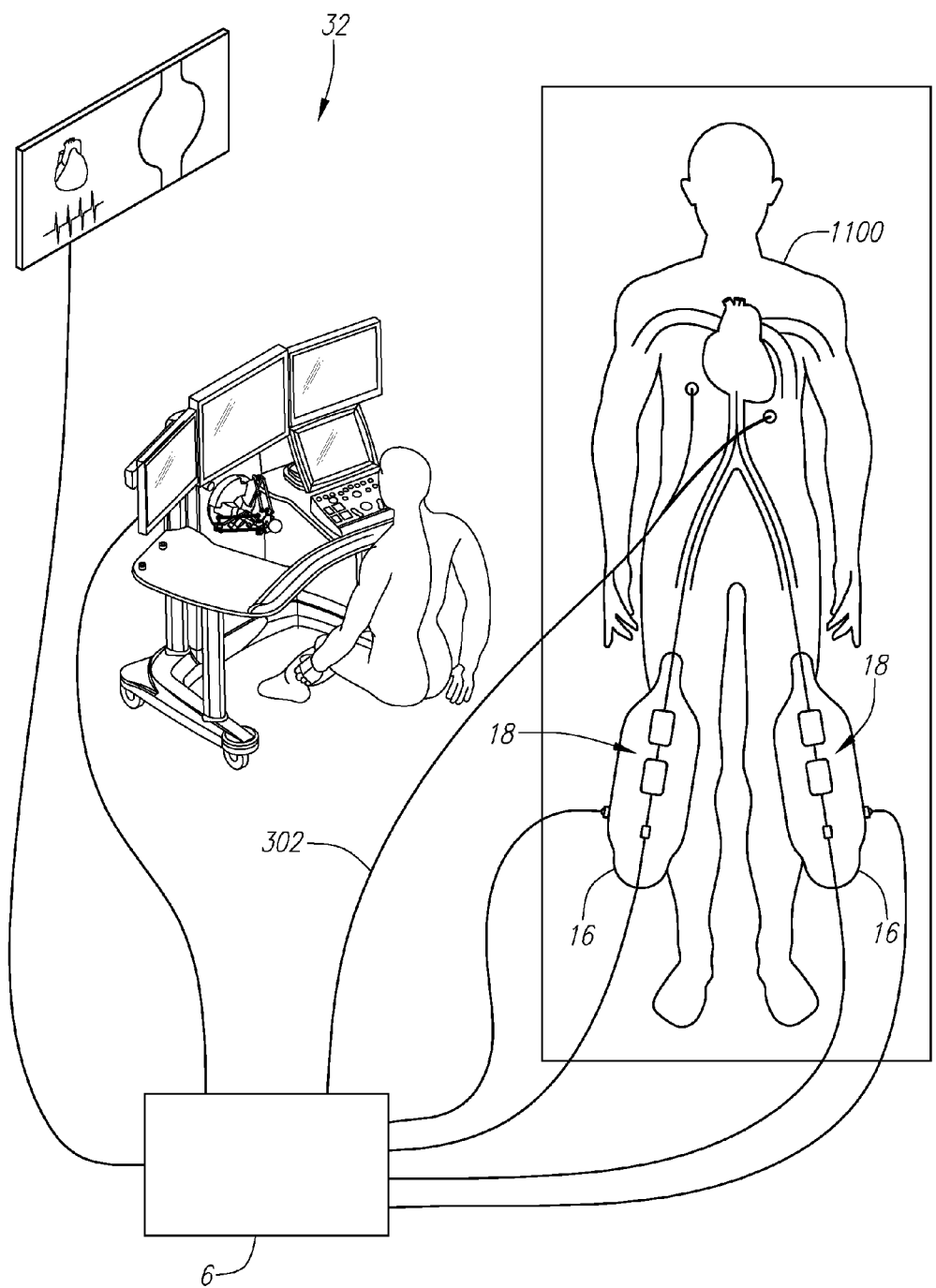
FIG. 3 illustrates one embodiment of a robotic surgical system being used to perform diagnostic and/or interventional operations.

FIG. 3 illustrates one embodiment of a robotic system (32) being used to perform diagnostic and/or interventional operations. Referring to FIG. 3, two instruments (18) are being used on a patient (1100) for performing minimal invasive surgical operations. Each of the instruments (18) may include a robotic catheter, a combination of robotic catheters, a robotic catheter having one or more ultrasound transducers, a robotic catheter having one or more surgical instruments, or any combinations thereof. As will be discussed in further detail, monitors (302) may be used to monitor the heart beat of the patient as a three-dimensional ultrasound map or model of the heart of a patient is produced during diagnostic and/or therapeutic procedures.

Figure 4A:
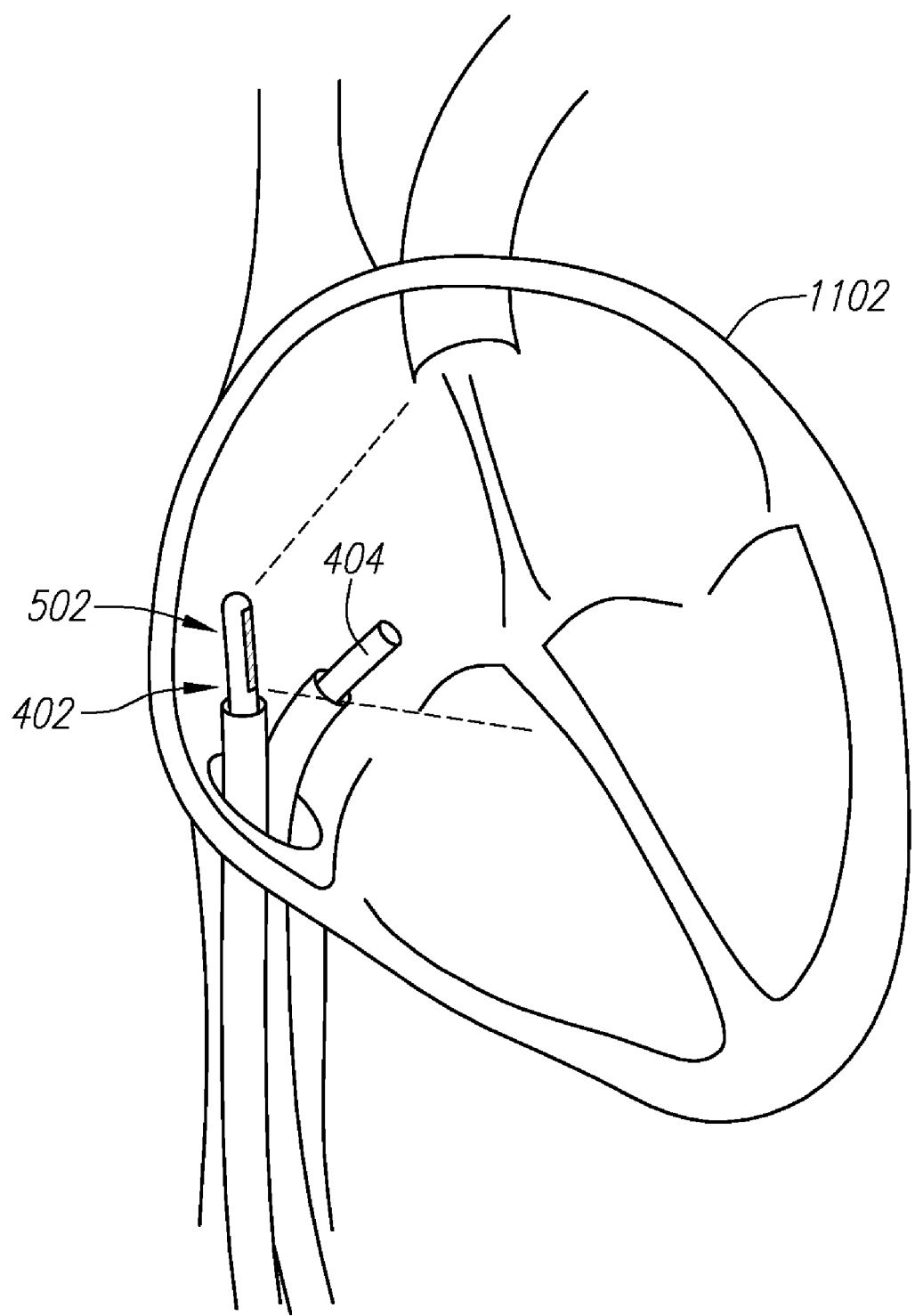
FIGS. 4A-M illustrate that two catheters have been advanced into the right atrium of the heart of a patient.

FIG. 4A illustrates that two catheters have been advanced into the right atrium of the heart of a patient. For example, one of the two catheters may be an intracardiac echocardiographic (ICE) catheter assembly (402) that may include one or more ultrasound transducers (502) (e.g., linear array ultrasound transducers, phased array ultrasound transducers, etc.) capable of producing two dimensional intracardiac echocardiograms. The ICE catheter (402) may be capable of producing two dimensional intracardiac echocardiograms of the heart (1102). In some situations, instead of the complete organ, the intracardiac echocardiograms may only provide an image of a part of an organ. For example, if a subject organ is the heart, the intracardiac echocardiogram may provide an image the left atrium, instead of all the chambers of the heart. The intracardiac echocardiograms may also include the image of a robotic catheter (404) that is being advanced toward the left atrium of the heart through the septum. The robotic catheter (404) may include a sheath catheter, a guide catheter, an ablation catheter, etc. For a detailed discussion of intracardiac echocardiogram please refer to "Intracardiac Echocardiography", which is edited by Frank E. Silvestry MD and Susan E. Wiegers MD and published by Informa Healthcare on Nov. 29, 2005, and the publication is incorporated by reference herein in its entirety.

Figure 4B:
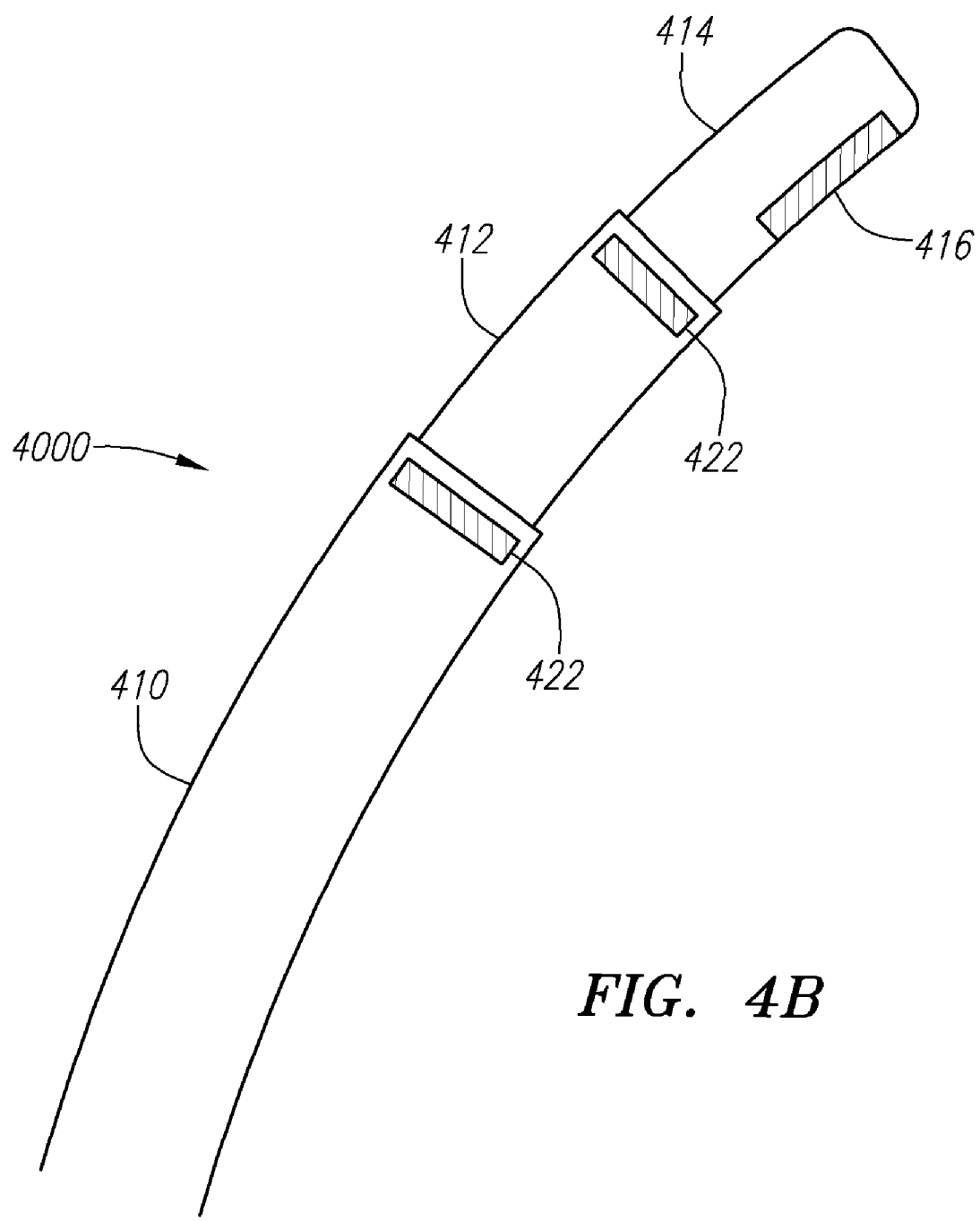
Figure 4C:
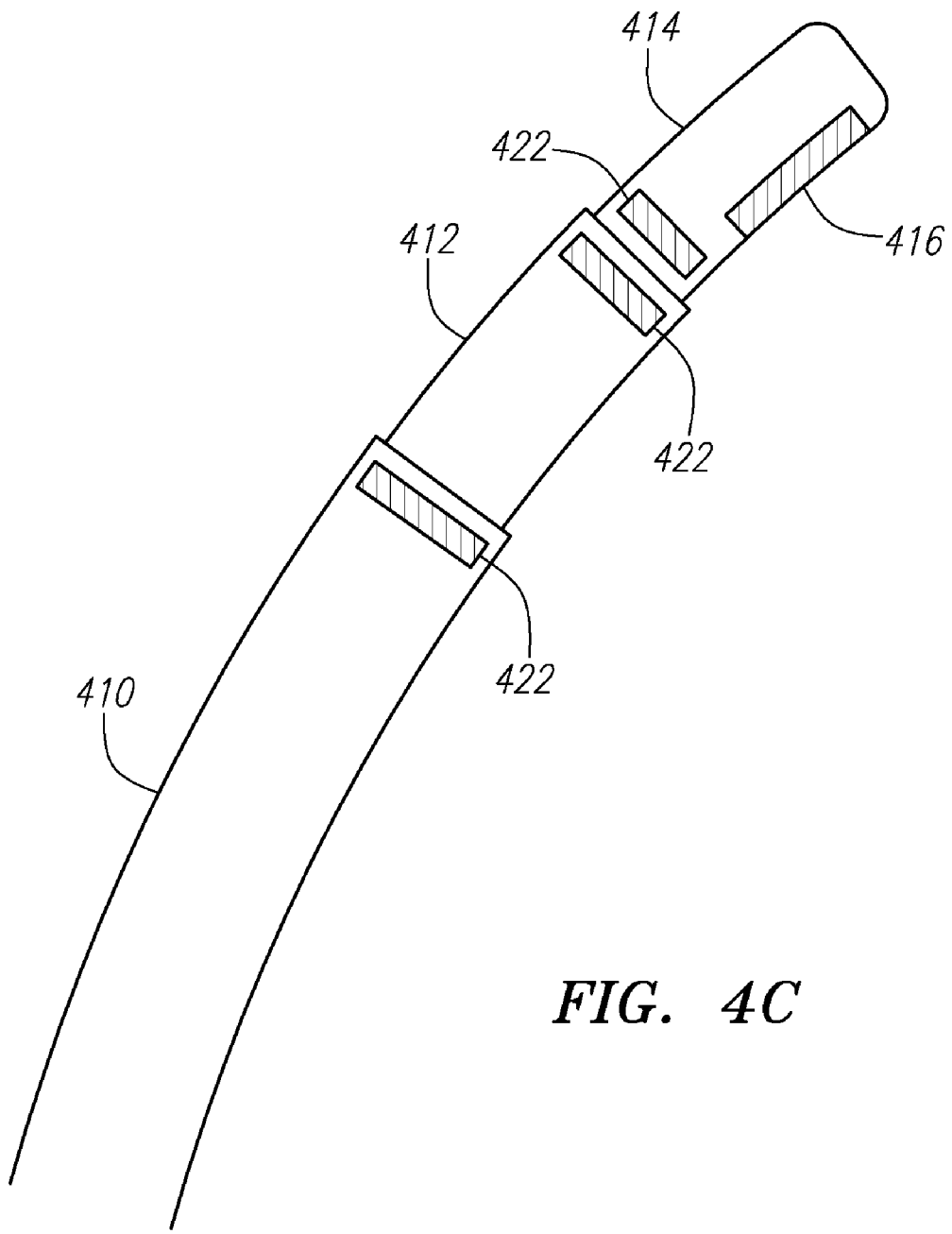

All of the following technologies may be utilized with manually or robotically steerable instruments, such as those described in the aforementioned patent application U.S. Ser. No. 11/481,433. Referring to FIG. 4B, an assembly (4000), which may be part the instrument (18), is depicted as comprising a robotic sheath instrument (410), robotic guide instrument (412), and ultrasound catheter (414). The terms "robotic sheath instrument (410)" and "robotic guide instrument (412)" shall have the meanings prescribed in the above-mentioned patent application (Ser. No. 11/481,433). The depicted guide instrument (412) is movably positioned within the working lumen of a sheath instrument (410) to enable relative insertion of the two instruments (412, 410), relative rotation, or "roll" of the two instruments (412, 410), and relative steering or bending of the two instruments (412, 410) relative to each other, particularly when a distal portion of the guide instrument (412) is inserted beyond the distal tip of the sheath instrument (410). The depicted assembly (4000) comprises localization sensors (422) or devices (422) coupled to both the sheath instrument (410) and/or guide instrument (412). Suitable localization sensors (422) or devices (422) are described in the aforementioned patent application, U.S. Ser. No. 11/481,433. Preferably the localization sensors (422) are configured to provide three-dimensional location data (i.e., X, Y, Z coordinates) in real time or near real time for the sensor location as coupled to the pertinent instrument (e.g., 410, 412). One or more of the sensors (422) or devices (422) may also be configured to provide orientational information as well—for example, yaw, pitch, and roll information for the position of the pertinent catheter or instrument to which the device (422) or sensor (422) is coupled. The depicted assembly (4000) also comprises an ultrasound imaging catheter (414) comprising an ultrasound transducer (416). The ultrasound imaging catheter (414) is positioned through the working lumen of the guide instrument (412) and may be configured to be either relatively firmly coupled to prevent relative motion between the guide instrument (412) and ultrasound catheter (414), or movably coupled to allow relative insertion and/or roll between the guide instrument (412) and ultrasound catheter (414). In the event the two are movably coupled, it is desirable in one embodiment to also have a localization device (422) coupled to the ultrasound catheter (414), as depicted in FIG. 4C. The ultrasound transducers (416) depicted in FIGS. 4B and 4C preferably are linear array or phased array type ultrasound transducers, and ultrasound catheters comprising such transducers are available from manufacturers such as the Acuson division of Siemens under the trade name "AcuNav", for example.

Figure 4D:
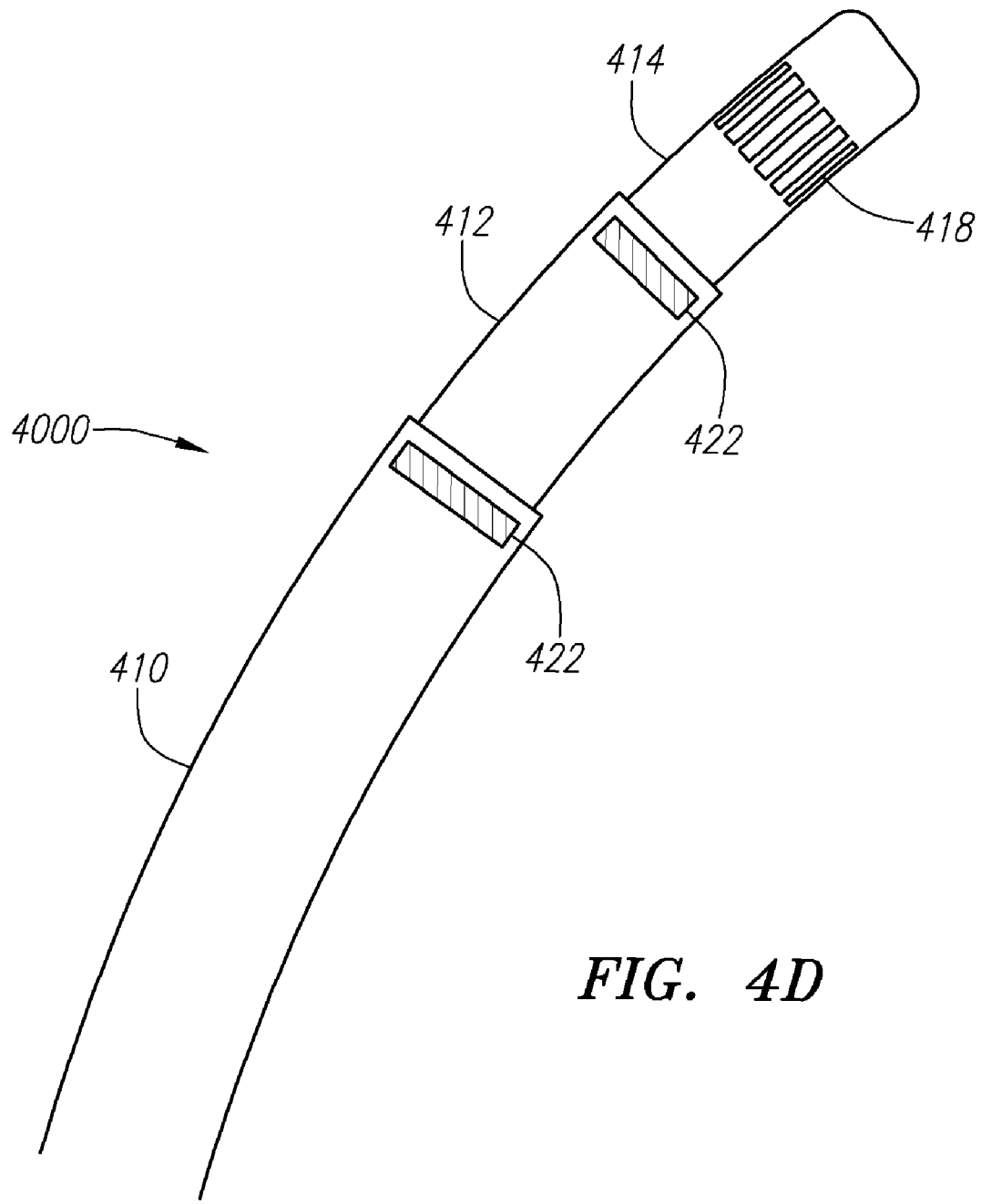

FIG. 4D depicts another variation similar to that of FIG. 4b, with the exception that the ultrasound catheter (414) comprises a set of circumferential ultrasound transducers (418) which may be selectively activated to enable perimetric image capture without as much roll activity as would be required by a more conventional linear or phased array transducer to capture an image of tissue or structures surrounding the entire perimeter of the ultrasound catheter (i.e., a conventional linear or phased array transducer would need to be rolled by about approximately 360 degrees to capture images about the entire perimeter, while a circumferential transducer set may be sequentially or simultaneously activated to capture a similar set of images about the perimeter). Catheters comprising circumferential transducer sets such as that depicted in FIG. 4D are available from suppliers such as Volcano Therapeutics, Inc.

Figure 4E:
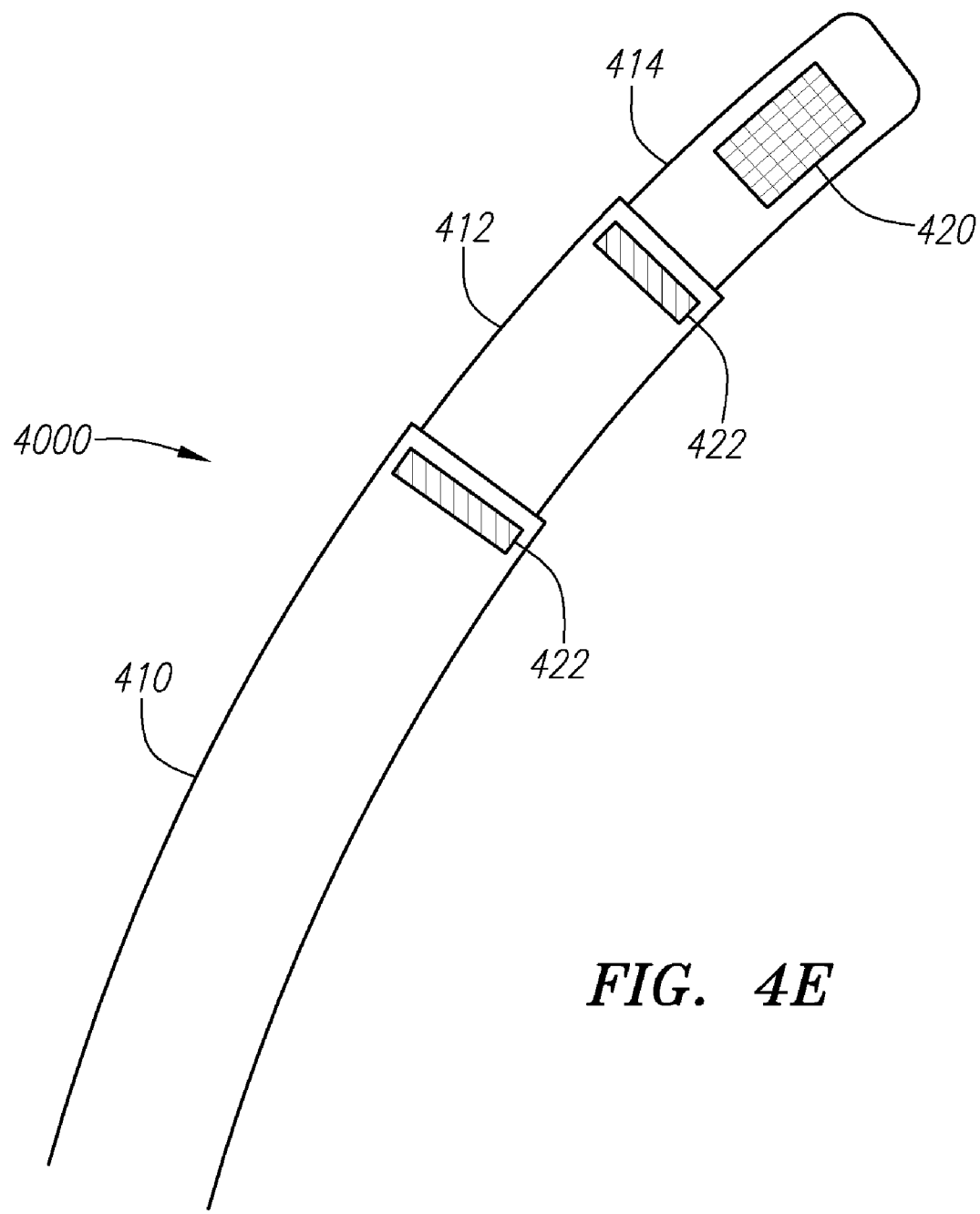

FIG. 4E depicts an embodiment similar to that depicted in FIG. 4B, with the exception that the ultrasound catheter (414) comprises a two-dimensional ultrasound transducer matrix (420) comprising a matrix of elements or cells, each of which may be activated to capture image data which, in the aggregate, may be utilized to produce a three-dimensional image of a nearby structure. Two-dimensional matrix transducers are manufactured by suppliers such as Phillips and may be positioned relative to the ultrasound catheter structure in a planar configuration, semi-circumferential configuration, or other geometric configurations.

Figure 4F:
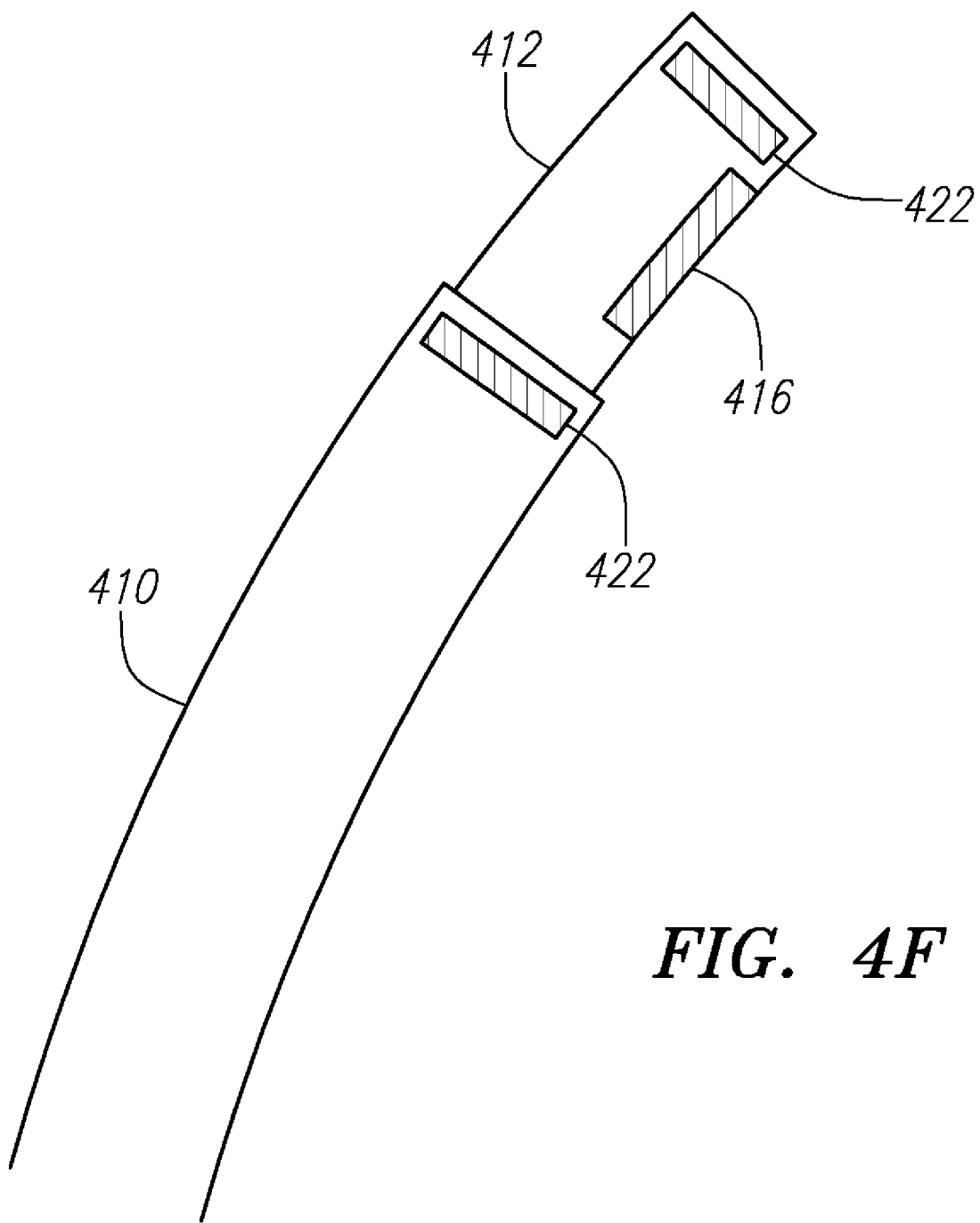
Figure 4G:
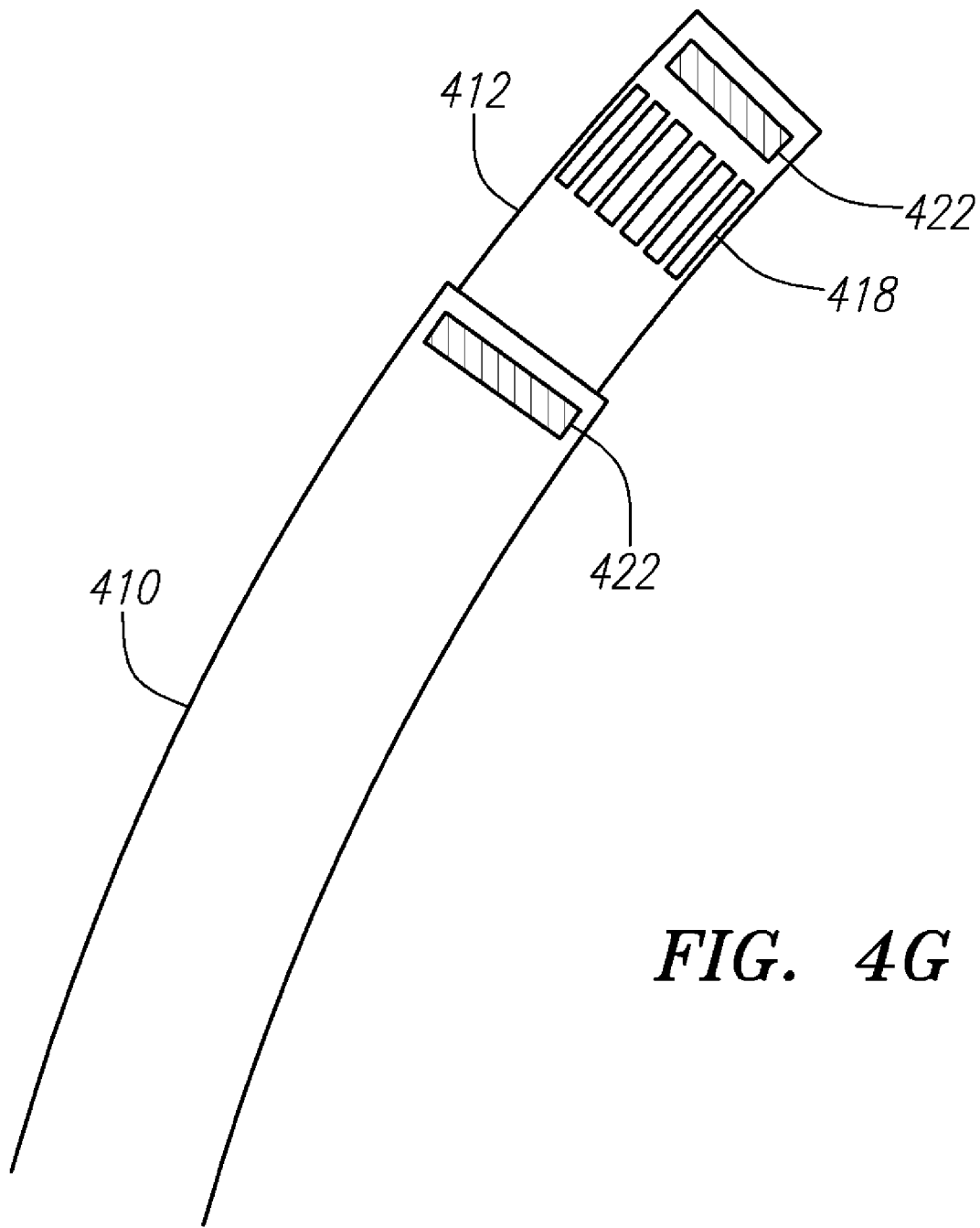
Figure 4H:
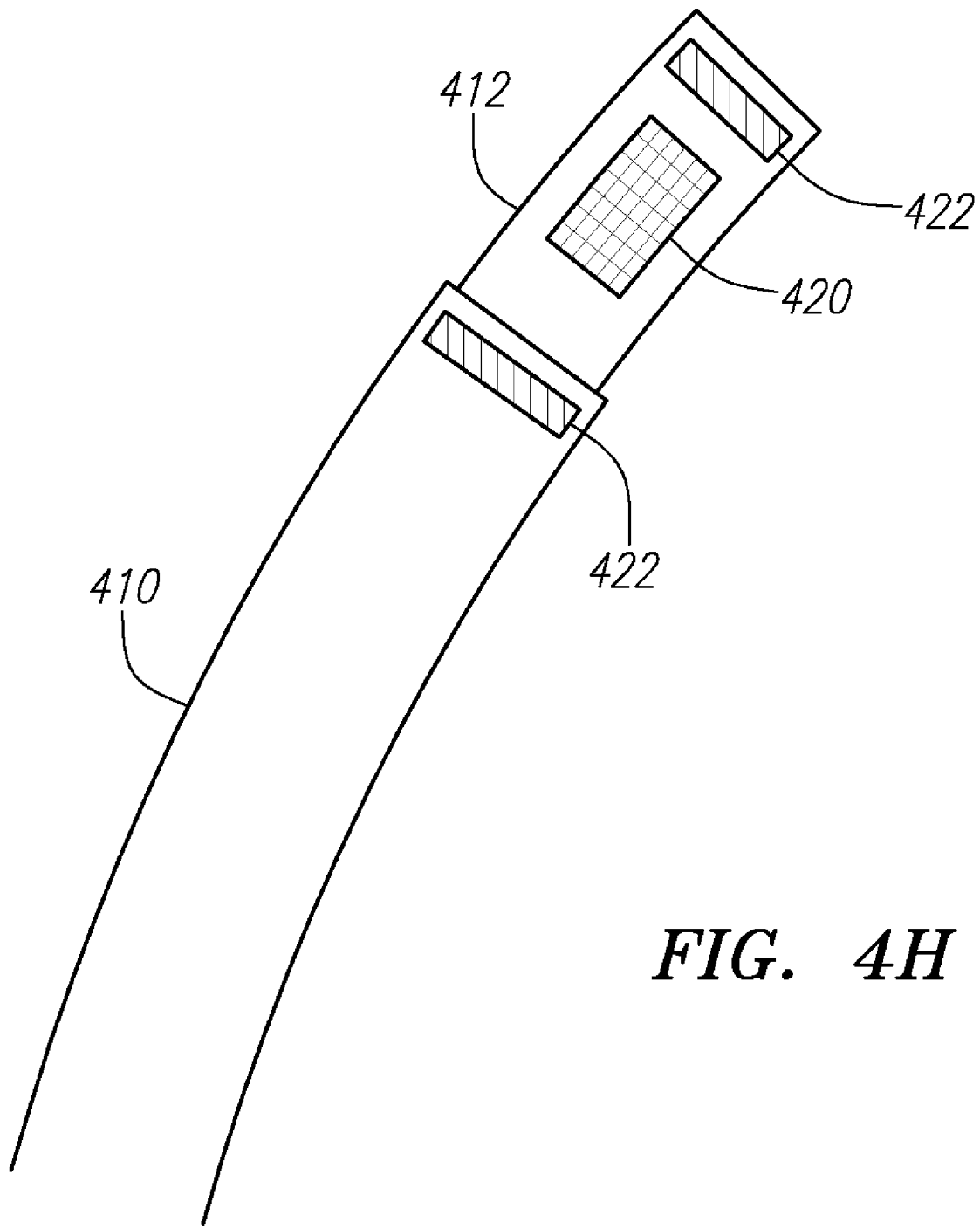
Figure 4I:
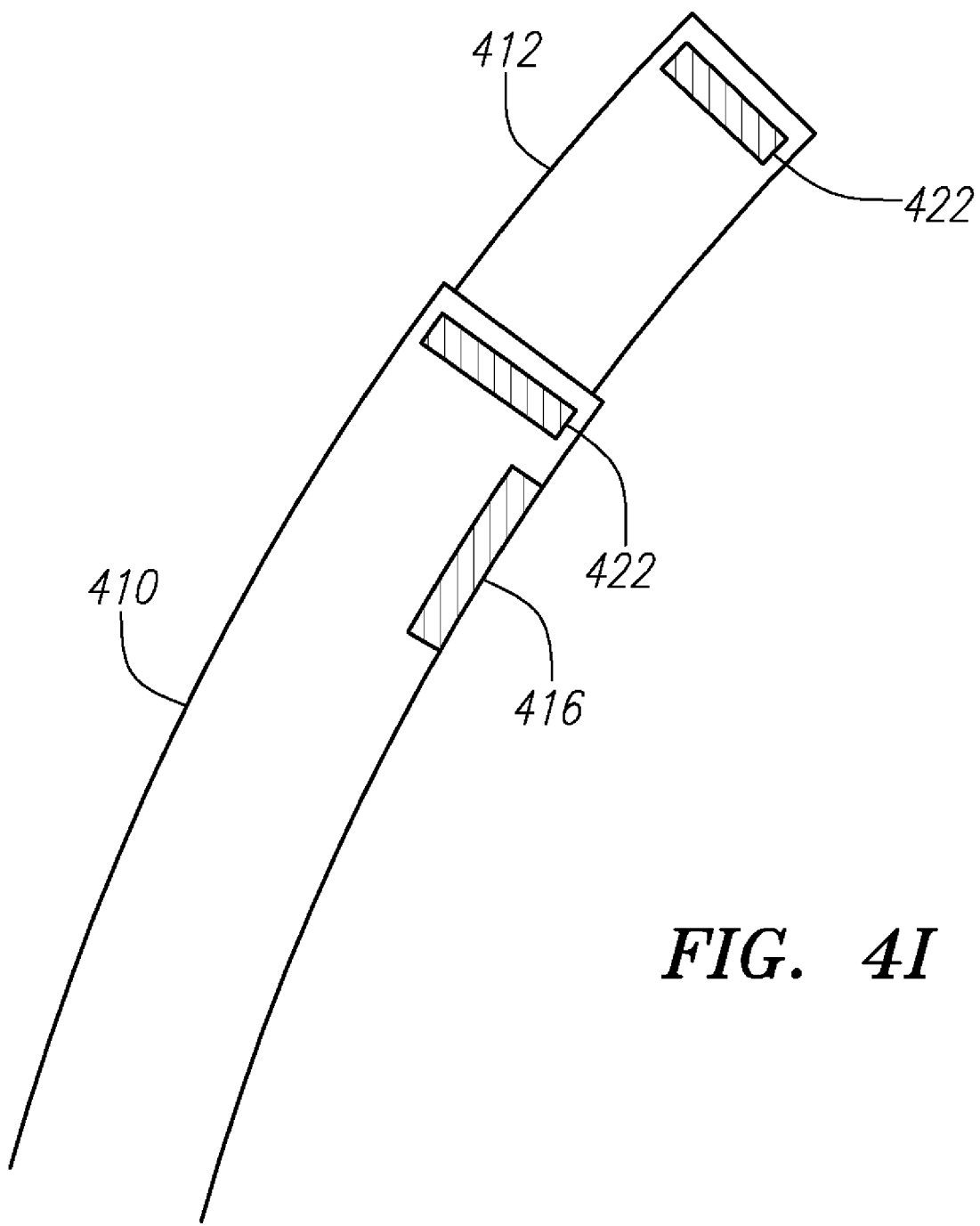
Figure 4J:
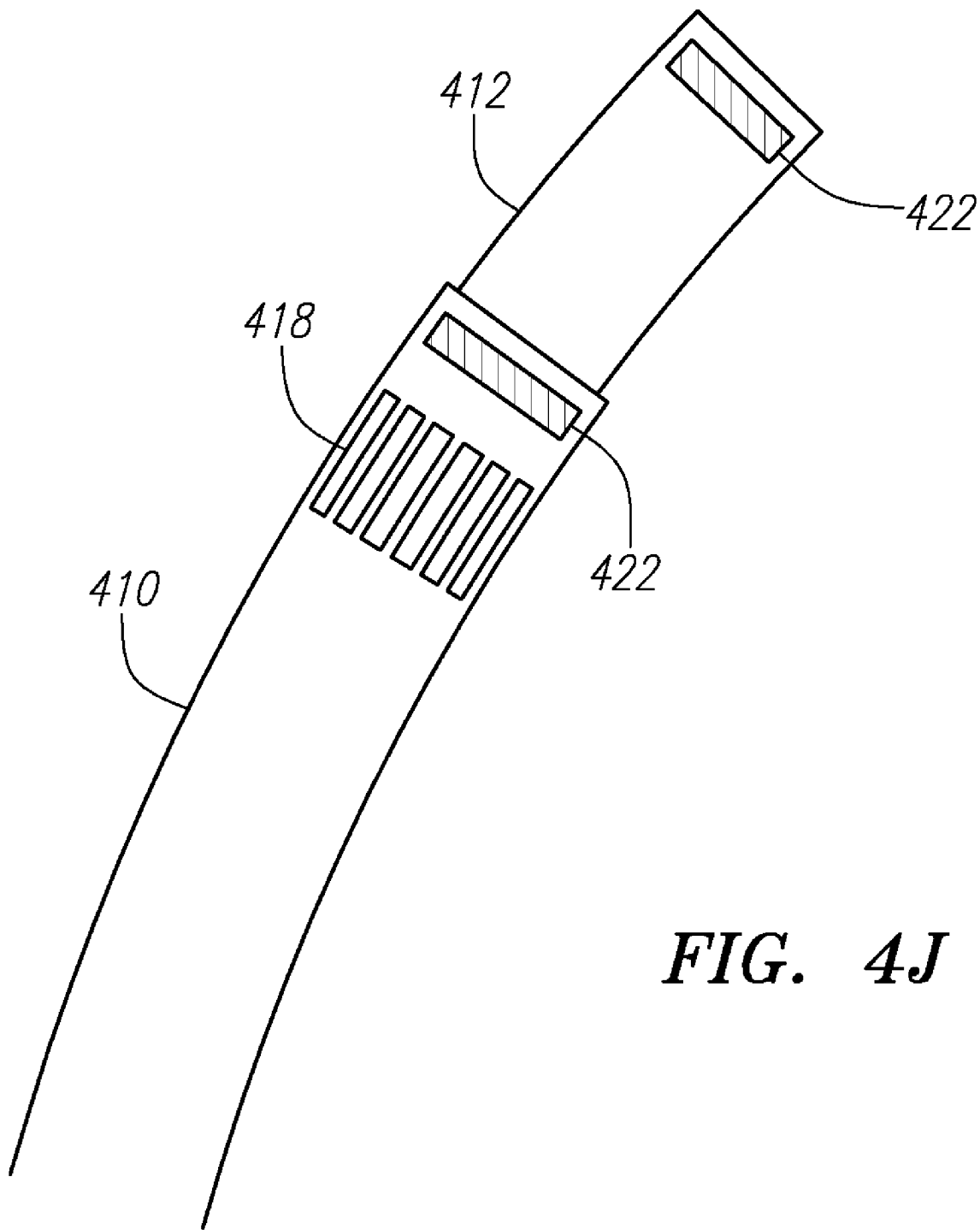
Figure 4K:
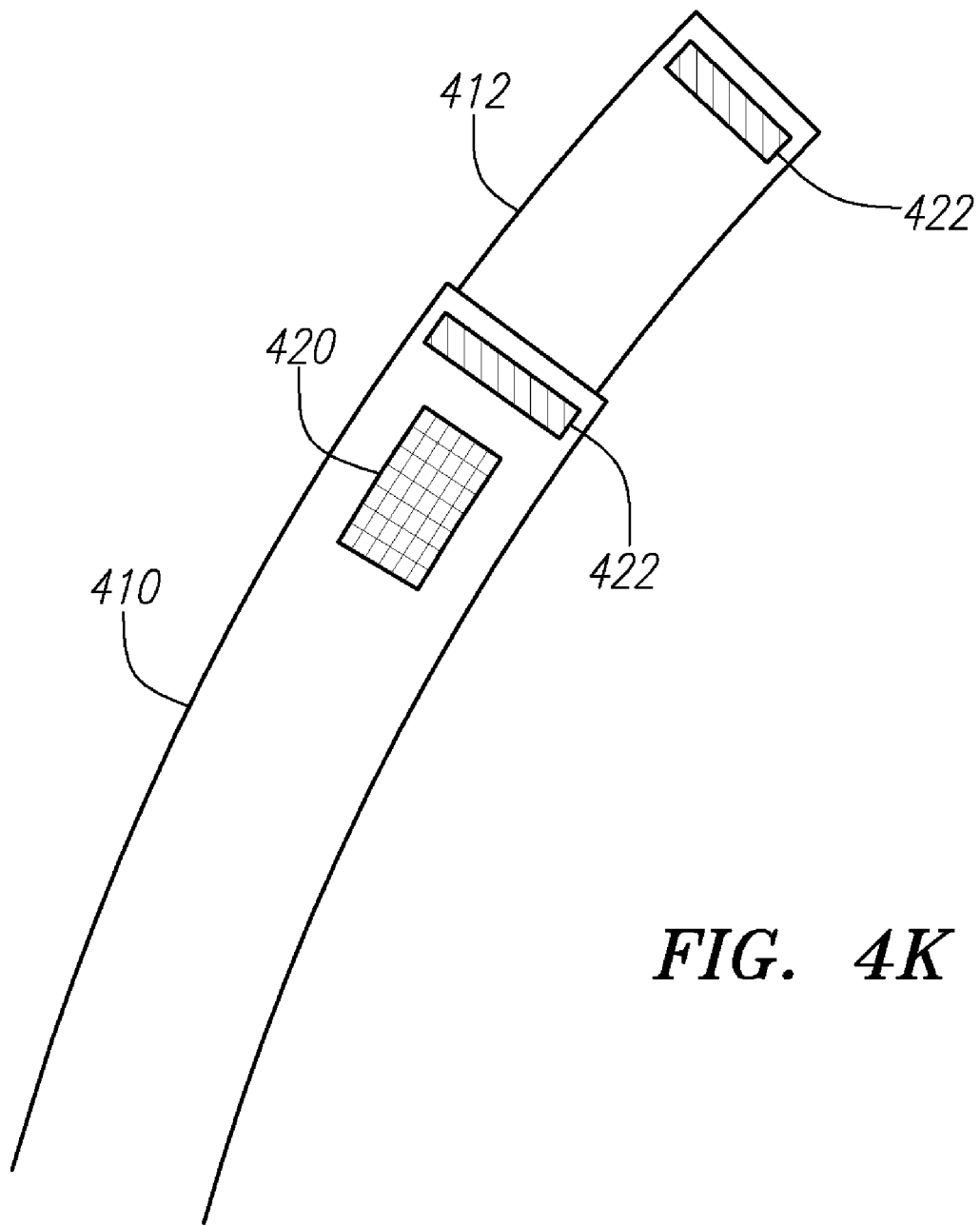

FIG. 4F through FIG. 4H depict more integrated embodiments, wherein various types of ultrasound transducer configurations (linear or phased array configuration in FIG. 4F, circumferential configuration in FIG. 4G, and two-dimensional matrix configuration in FIG. 4H) are depicted coupled directly to a guide instrument (412). Similarly, the various ultrasound transducer variations may be coupled to a sheath instrument (410) structure, as depicted in FIGS. 4I, 4J, and 4K. In other embodiments (not shown), both a guide (412) and sheath (410) instrument of a particular instrument (18) assembly may be instrumented with various types of ultrasound transducers.

Figure 4L:
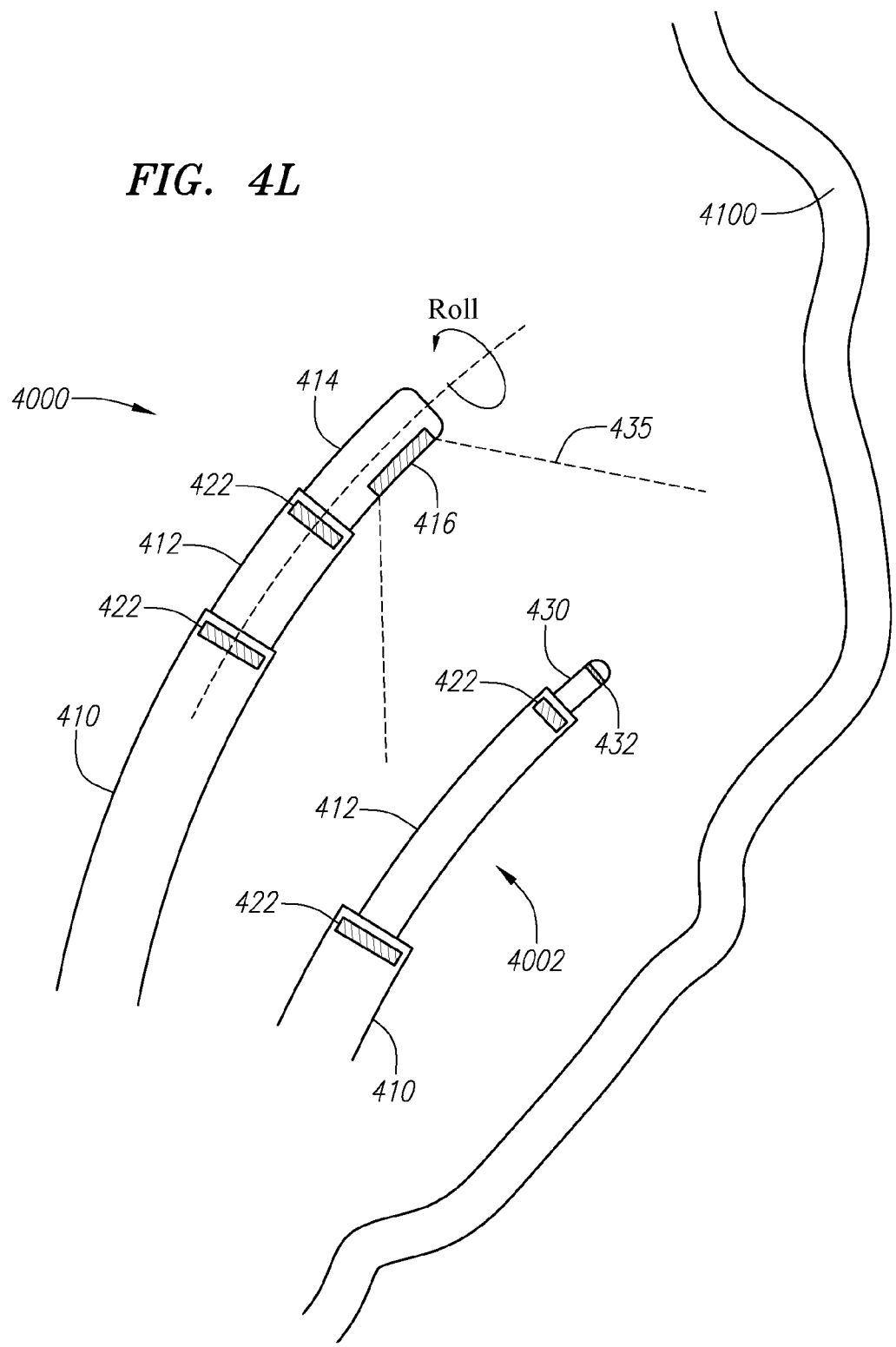

Referring to FIG. 4L, an assembly (4000) such as that depicted in FIG. 4L is depicted in use as an imaging platform along with another robotic catheter instrument assembly (4002) in use as an interventional platform comprising a sheath instrument (410), a guide instrument (412), and an electrophysiology catheter (430) positioned through the working lumen of the such guide instrument (412), the electrophysiology catheter (430) comprising an electrode (432) configured for cardiac mapping and/or ablation uses. Configurations similar to those depicted in FIGS. 4B through 4K may be utilized for the imaging platform instrumentation. As depicted in FIG. 4L, as the ultrasound transducer (414) of the imaging platform assembly (4000) is rotated or rolled about the axis of roll rotation of the ultrasound catheter relative to the guide (412) and sheath (410) instruments, the field of view (435) of the depicted linear or phased array transducer may be utilized to capture ultrasound images or "slices" oriented in space about the imaging platform assembly (4000) and preferably capturing in one or more of these images at least a portion of the interventional assembly (4002), most preferably the distal portion of the interventional assembly (4002) and nearby tissue structures (4100), in the case of an electrophysiological intervention with a distal electrode, as depicted in FIG. 4L. At the heart of the system of instrumentation depicted in FIG. 4L is localization of two instrument platforms (4000, 4002), and ultrasound imaging of one of the platforms by the other in a fashion wherein the field of view (435) of imaging is movable to accommodate relative movement between the two platforms, capturing of various nearby other structures, etc, through the use of movement (yaw, pitch, insertion, roll) of the platform comprising the ultrasound transducer. Localization data from the two platforms (4000, 4002) enables computation of the relative positioning of the two assemblies. Depending upon the range of relative motion between guide instrument (412) and sheath instrument (410), it may be overly redundant to have localization devices coupled to both, as depicted in FIG. 4L. As discussed above, it may be useful in other variations to have localization devices coupled to the structure positioned within the guide instrument (412) working lumen, whether such structure is an ultrasound catheter, electrophysiology catheter, etc—depending upon the relative motion anticipated between such structure and the pertinent guide instrument (412). An interventional assembly (4002) comprising an electrophysiology catheter (430) is utilized herein for illustrative purposes—and the techniques and systems disclosed herein may be equally applied with other interventional instruments—or non-interventional instruments (i.e., simple mechanical probes, needles, remotely actuated tools such as graspers, etc) similarly configured (in which case the "interventional assembly" is more aptly termed the "second assembly").

Determining roll orientation may be a challenge with conventional localization sensing devices, and for this reason, it is preferable in some embodiments to facilitate determination of the roll (or rotational) positioning of the imaging platform assembly (4000) relative to other instrumentation, nearby tissue structures, or other nearby structures such as the operating table. In one embodiment, roll orientation may be determined by relative positioning to previously registered anatomical or other landmarks on nearby structures. Landmarks may be anatomical (i.e., a particularly dense or thick portion of tissue), or may be mathematical (i.e., points with high eigenvalues may be used with data processing algorithms such as optical flow algorithms to detect landmarks of particular texture, etc).

Figure 4M:
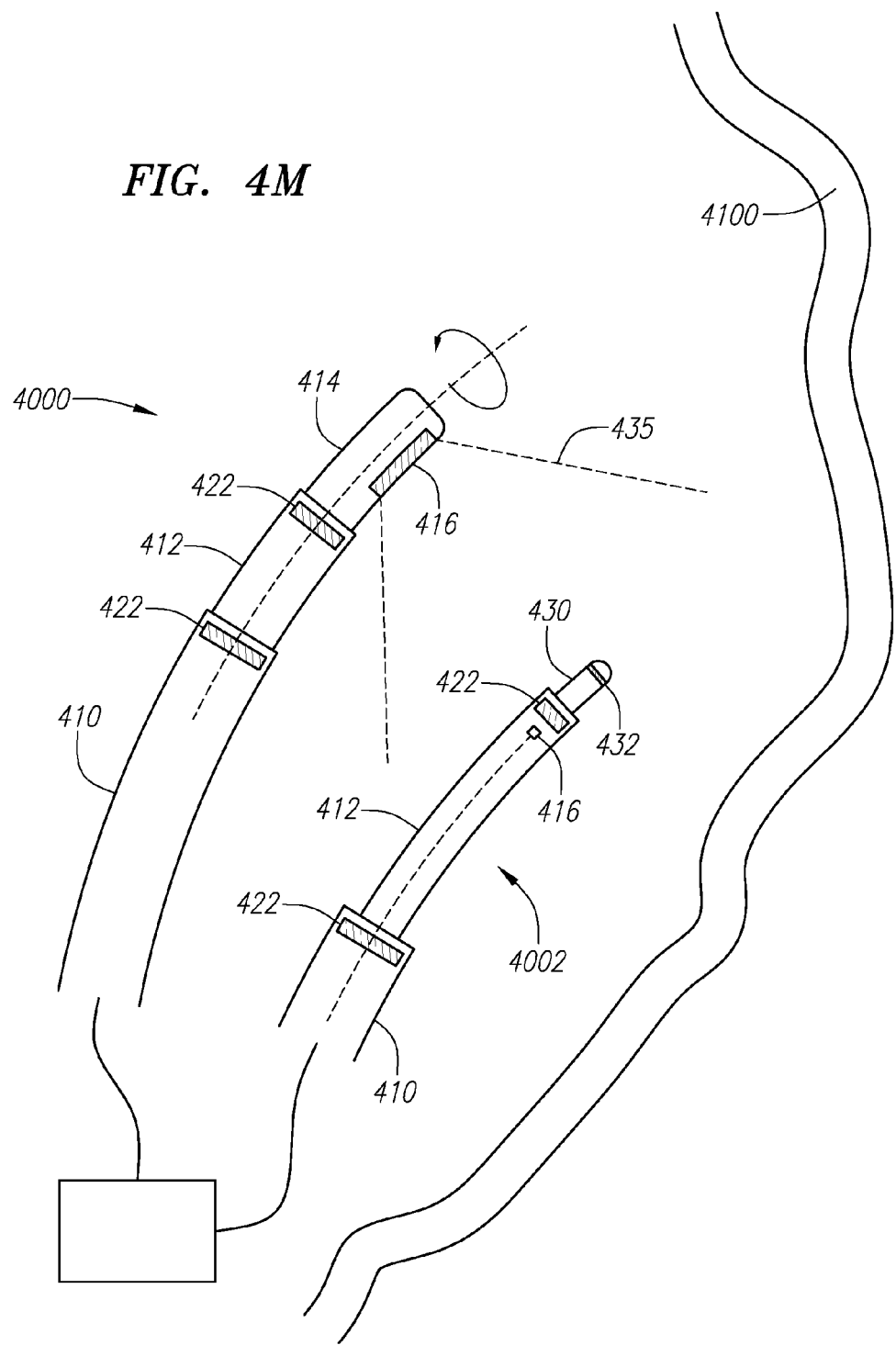

Alternatively, an additional transducer may be utilized. Given a system such as that depicted in FIG. 4M, wherein the interventional assembly (4002) embodiment comprises an ultrasound catheter (414) coupled to such assembly, in this case coupled to the guide instrument (412), several techniques may be utilized to determine the roll orientation of the imaging platform assembly (4000). In one embodiment, the ultrasound transducer (416) of the interventional assembly (4002) may be utilized to transmit ultrasound energy detectable as a "hot" or "bright" spot by the ultrasound transducer of the imaging platform assembly (4000). The ultrasound transducer (416) of the interventional assembly (4002) may comprise a single crystal ultrasound transmitter, which in one embodiment is rolled by the robotic catheter assembly (4002) to provide more detectability by the imaging assembly (4000) from different directions, or may comprise a circumferentially arranged set of single crystals configured for relatively easy detection by the imaging assembly (4000). With such embodiments, when the imaging assembly (4000) ultrasound transducer (416) detects a "ping" from the other instrument assembly (e.g., 4002), a computing system may determine the roll position of the imaging assembly (4000) when the "ping" was detected given the localization data from both assemblies. In another variation, the transducer or transducers on the second assembly (4002) may be configured to be in receive mode, and to signal the computing system when it is receiving ultrasound energy transmitted from the ultrasound transducer (416) on the imaging platform assembly (4000), thereby allowing the computing system to calculate the roll orientation of the imaging platform assembly (4000) ultrasound transducer (416) with use of the localization data from both assemblies (4000, 4002). In another variation wherein one of the imaging platform assembly (4000) or second assembly (4002) does not comprise a localization sensor or device, one or more ultrasound transducers coupled to the second assembly (4002) may be utilized, along with acoustic line data from the ultrasound mainframe associated with the imaging platform assembly (4000) transducer to localize the imaging platform assembly (4000), since a vector may be calculated between the receiving ultrasound transducer on the second assembly (4002) and the transmitting ultrasound transducer on the imaging assembly (4000) given the signal strength received by the receiving transducer versus time and the actuation activation along the transducer array of the transmitting transducer. In other words, one has localization information for one assembly, and with the acoustic line data for the activation timing of the array, the geometric positioning and field of view of the transmitting array, and receiving intensity profile versus time of the receiving transducer, one may calculate a precise vector in space from one assembly to the other, thus enabling the calculation of the spatial positioning of one assembly relative to the other. Given the relative spatial positioning and localization data for one assembly, the location of the other assembly may be calculated and this information may be used for orientation calculation, etc.

Referring back to the illustrative system of catheter assemblies depicted in FIG. 4L, ultrasound and localization may be utilized to provide an image mapping of a volume about which the field of view (435) of the transducer of the imaging assembly (4000) has been rolled, pitched, yawed, inserted, etc. Indeed, one of the advantages of positioning an ultrasound transducer upon a robotically steerable assembly, such as those depicted in FIGS. 4B through 4K, is that the transducer may be precisely positioned. In other variations, non-robotic steerable catheters may be utilized. In one variation, a transducer comprising an imaging assembly (4000) maybe navigated all about through a subject volume, such as a chamber of a heart, bladder, kidney, esophagus (as in the case of trans-esophageal echocardiography) etc., to facilitate the capture of many slices of ultrasound data which may be assembled, given relative location and orientation data, into voxels, or volumetric pixels, which may be utilized by an operator for navigational, diagnostic, interventional, etc uses. Gating techniques may be utilized to decrease or eliminate the impact of cyclic motion such as that associated with heart cycles or breathing. In another variation, data may be acquired throughout a given sampling period of time for later analysis versus time to produce two or three dimensional images versus time, somewhat like a movie (sometimes referred to as "4-D" ultrasound imaging—or 3-D ultrasound versus time).

Figure 5A:
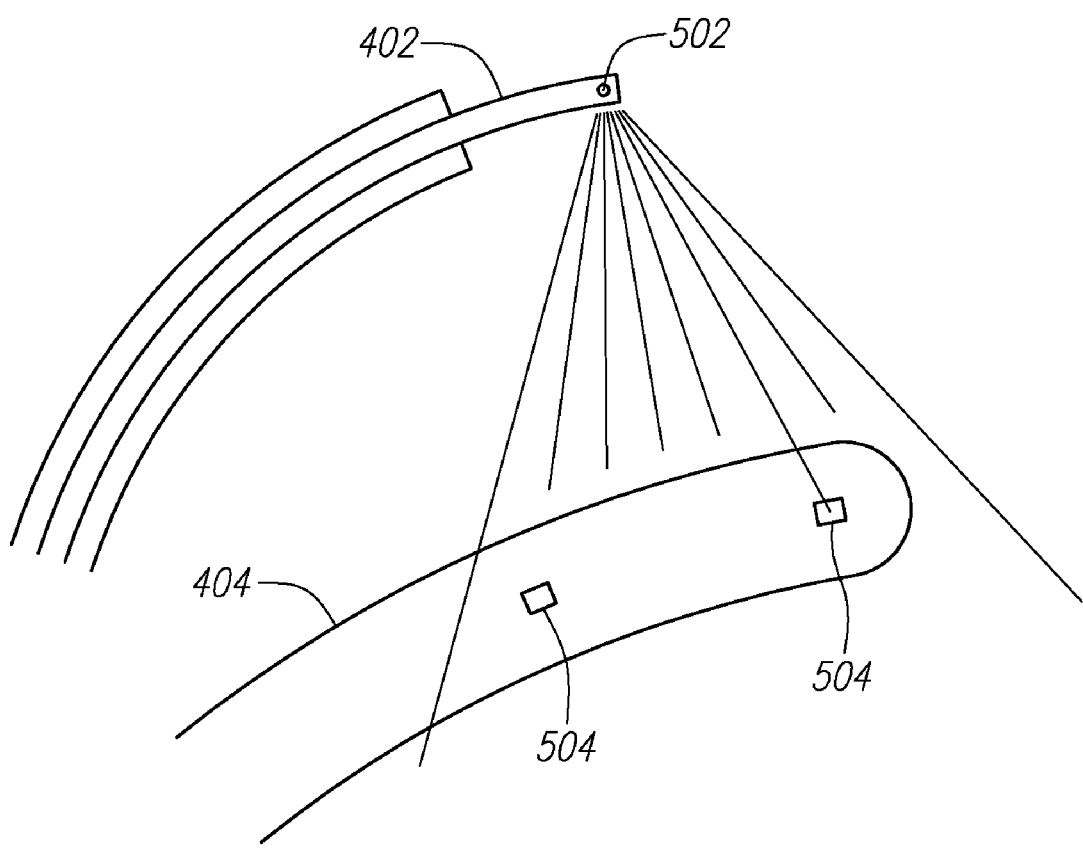
FIG. 5A illustrates one embodiment of a robotic catheter and an intracardiac echocardiographic catheter.
Figure 5B:
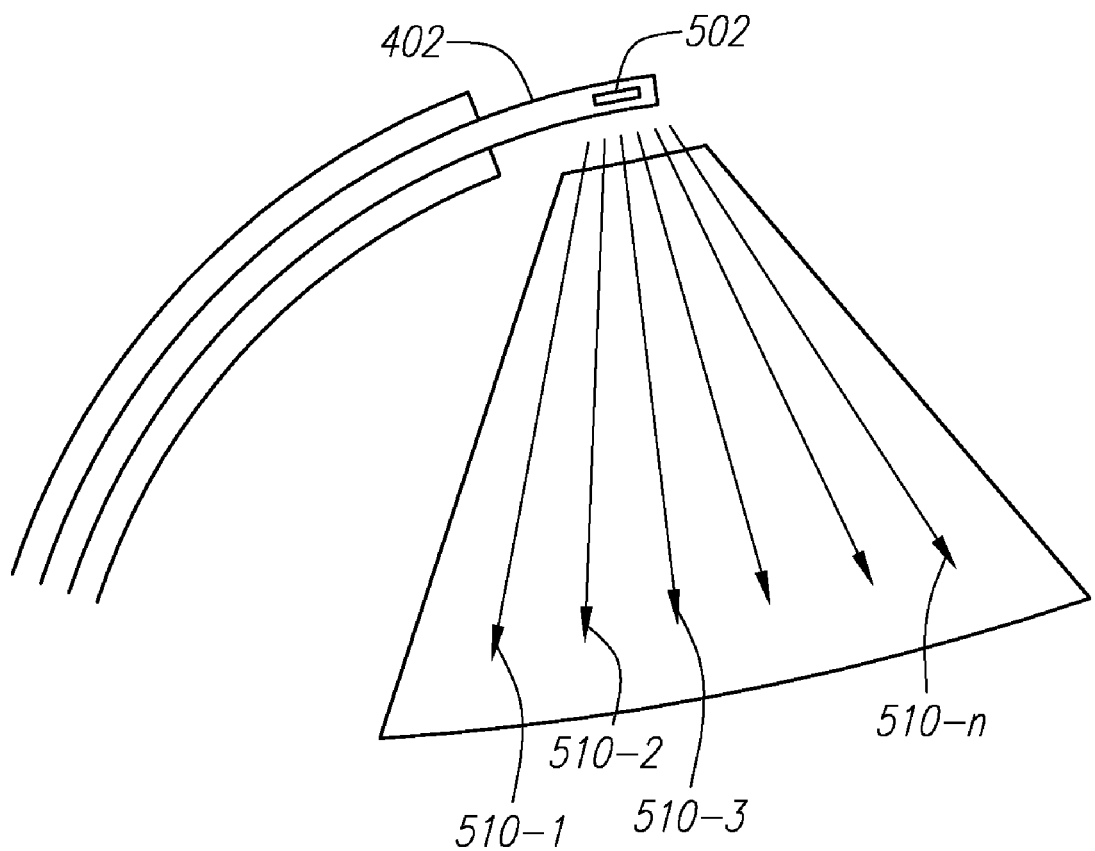
FIG. 5B illustrates transmission of ultrasound signals in one plane of transmission.
Figure 5C:
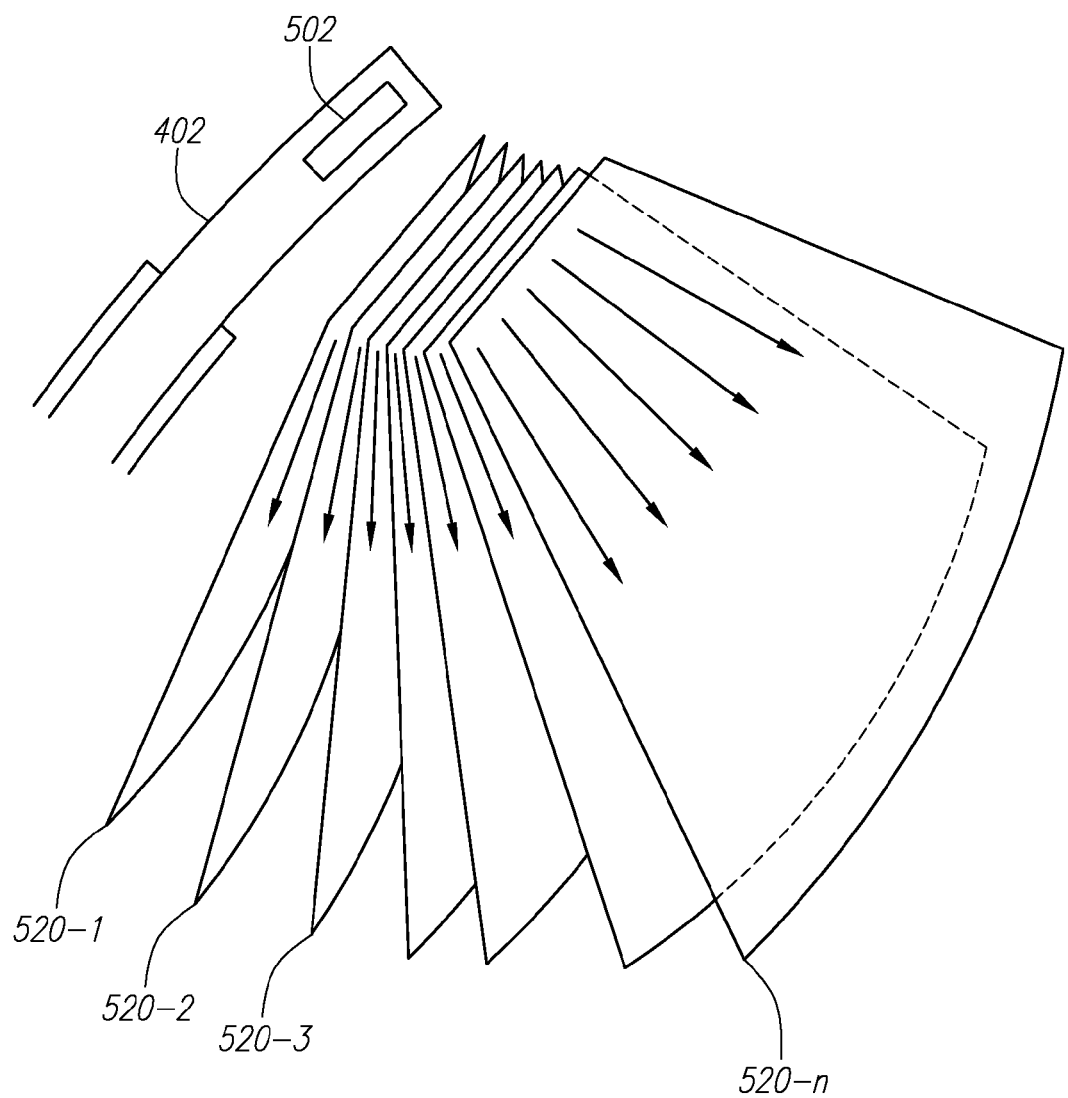
FIG. 5C illustrates transmission of ultrasound signals in multiple planes of transmission.

FIG. 5A illustrates that a catheter (404) may be equipped with one or more transponders (504) that are capable of interfacing (e.g., transmit as well as receive ultrasound signals) with the one or more ultrasound transducers (502) on imaging catheter (402), e.g., an ICE catheter, such that a signal (e.g., peak signal, insonified signal, etc.) may be generated when a transponder (504) is within the line and/or plane of an ultrasound transmission signal of the ultrasound transducer (502) of the ICE catheter (402). As illustrated in FIG. 5B, the ultrasound transducer (502) may be configured to transmit ultrasound signals (510-1, 510-2, 510-3 . . . , 510-n) in a plane to produce a planar sweep of ultrasound signals. The ultrasound signal (510-1, 510-2, 510-3 . . . , 510-n) may be transmitted in any appropriate manner (e.g., sequentially, etc.), such that each signal may be identified or distinguished by the system circuitry (not shown). As illustrated in FIG. 5C and will be discussed in further detail below, the ICE catheter (402) may also be rotated so that the transducer (502) not only transmit ultrasound signals substantially on one plane, but also configured to transmit ultrasound signals substantially in multiple planes (520-1, 520-2, 520-3, . . . , 520-n) as the catheter (402) is rotated. The system circuitry may also be configured to identify and distinguish the planes of transmission and the lines of transmission on each plane.

Figure 5D:
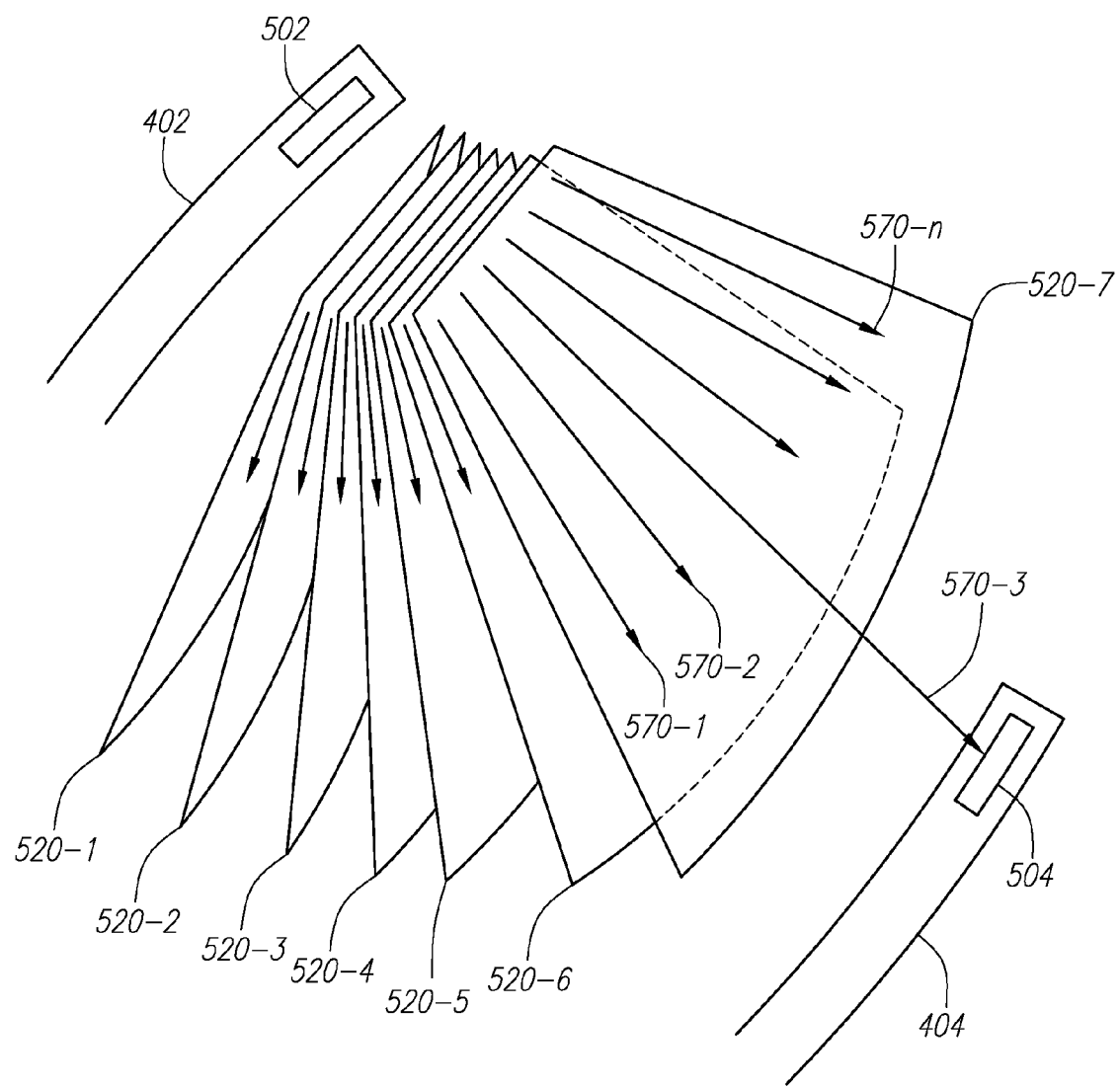
FIG. 5D illustrates transmission of ultrasound signals from a transducer and the direct reception of an ultrasound signal from a transponder.

Accordingly, transducer (502) may complete three-dimensional sweeps of ultrasound transmissions (e.g., lines of transmissions on multiple planes), and the transponder (504) may be in the direct path of transmission (line and plane of transmission) for one of the ultrasound signals as the transducer (502) completes the three-dimensional ultrasound sweeps. For example, ultrasound transmission line 570-3 on transmission plane 520-7 may be a direct transmission to the ultrasound transponder (504), as illustrated in FIG. 5D.

Figure 5E:
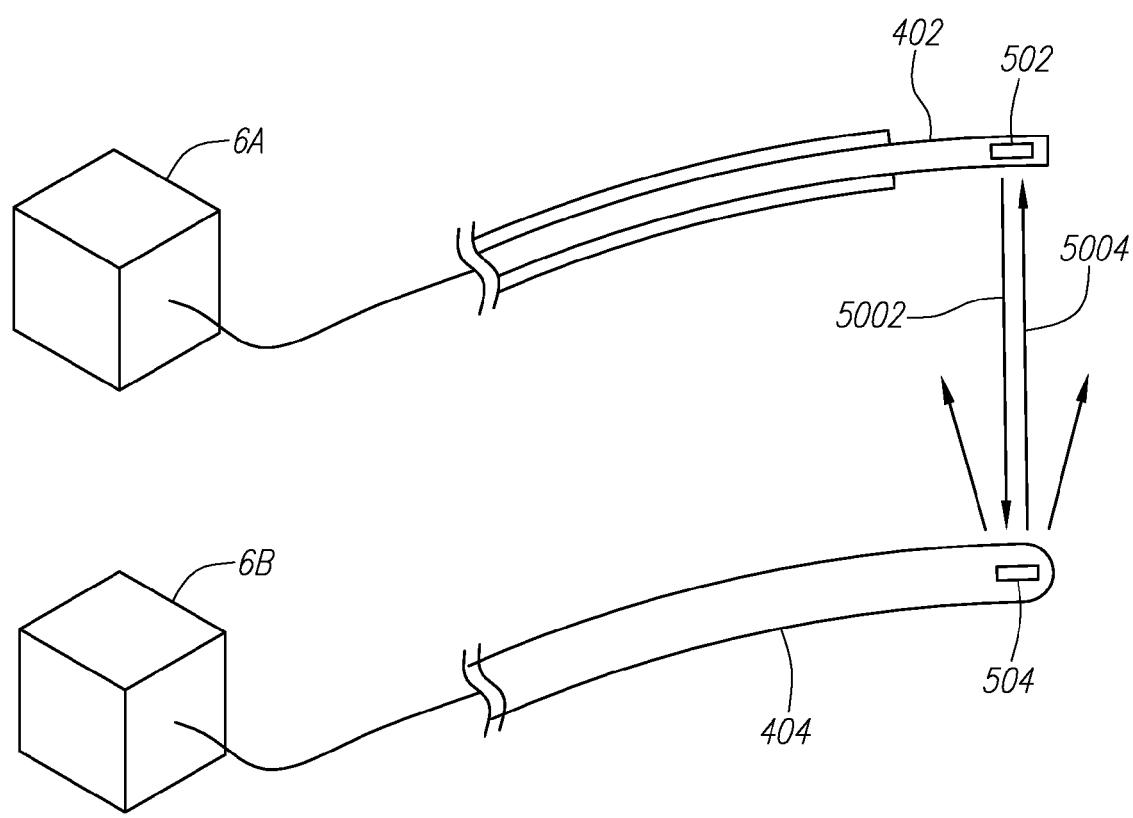
FIG. 5E illustrates one embodiment of an intracardiac echocardiographic catheter and robotic catheter system.
Figure 5F:
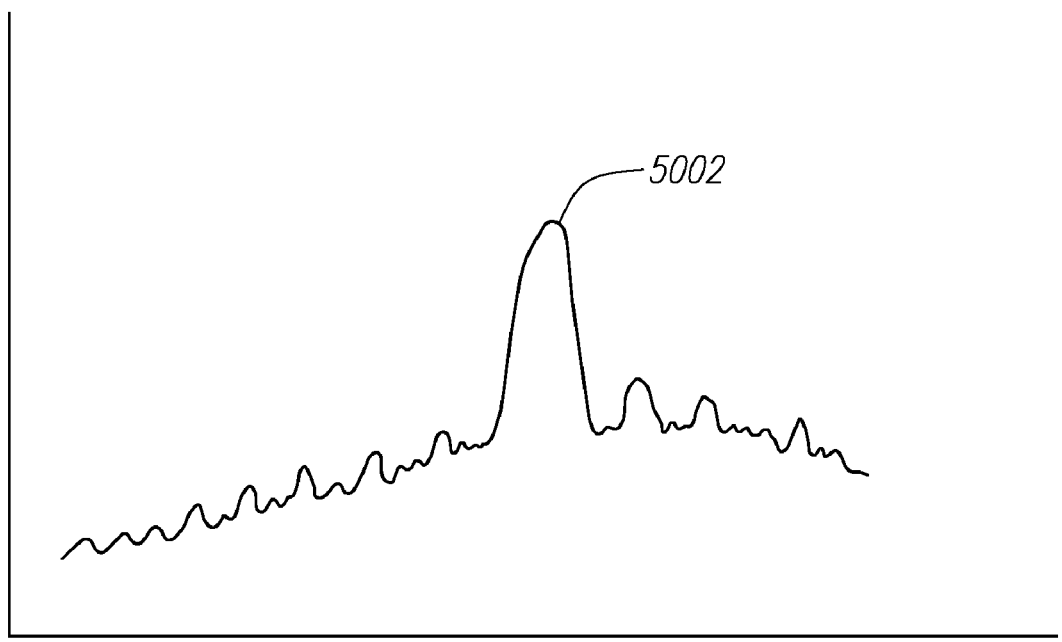
FIG. 5F illustrates a graph of the ultrasound signals.

In one embodiment, the transducer (502) may be configured to transmit as well as receive ultrasound signals as illustrated in FIG. 5E. System circuitry (e.g., hardware, software, firmware, etc.) for operating the transducer (502) for transmitting, receiving, and processing ultrasound signals may be housed in a sub-electronics rack (6A), which may be connected (e.g., by hard wire or wirelessly) to the system electronics rack (6). FIG. 5E illustrates that transducer (502) is transmitting an ultrasound signal (5002) which may be on a transmission line and transmission plane that is substantially directed toward the ultrasound transponder (504). The transponder (504) may also be configured to transmit as well as receive ultrasound signals as illustrated in FIG. 5E. System circuitry (e.g., hardware, software, firmware, etc.) for operating the transponder (504) for transmitting, receiving, processing, and amplifying ultrasound signals may be housed in a sub-electronics rack (6B), which may be connected to the system electronics rack (6). The substantially direct ultrasound signal (5002) from the transducer (502) may activate a substantially strong signal (5004), amplified signal (5004), or peak signal (5004) from the transponder (504) in response to such a substantially direct transmission. For instance, circuitry in the sub-electronics rack (6B) may be configured to measure the intensity of the signal (5002) and identify or compare a threshold magnitude, value, or transmission intensity for identifying that the signal (5002) is indeed a direct signal. In addition, circuitry in the sub-electronics rack (6B) may be configured to produce graphs of all the signals received from transducer (502) and from the graphs an operator may be able to identify a threshold magnitude, value, or transmission intensity for identifying that the signal (5002) is indeed a direct signal. FIG. 5F illustrates one example of a graph in which the intensity of the ultrasound signal (5002) from the transducer (502) may be determined as a direct signal.

Figure 5G:
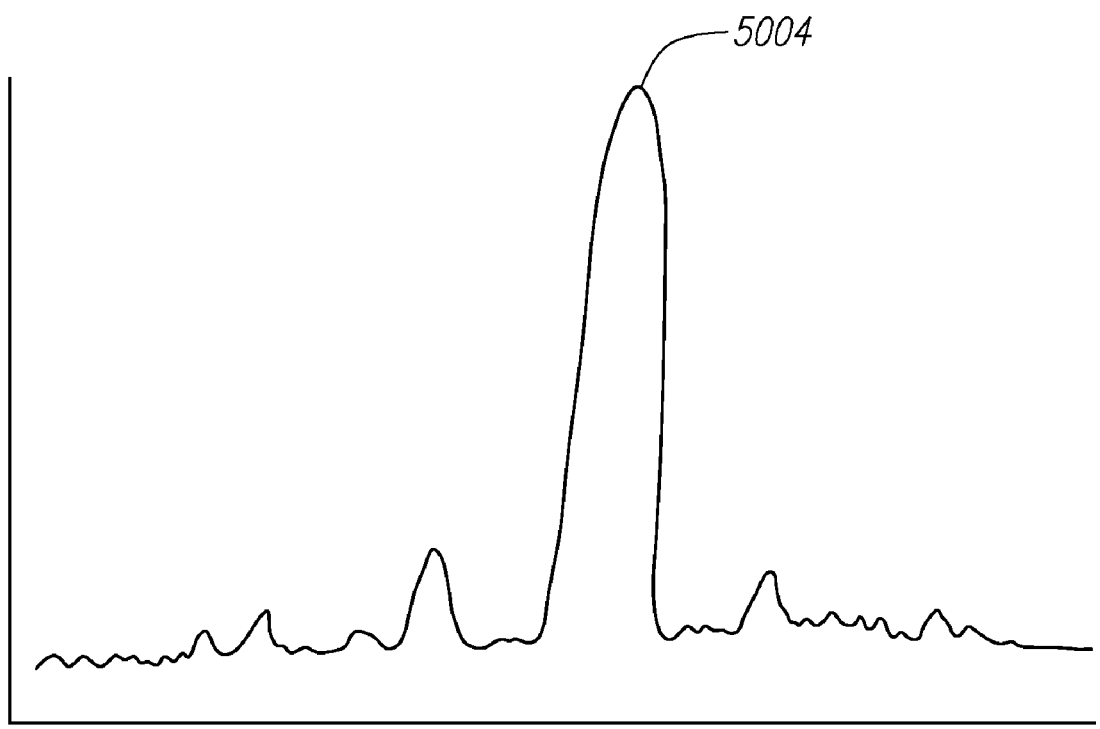
FIG. 5G illustrates another graph of the ultrasound signals.

Referring back to the operation of the transducer (502), the peak signal (5004) may be received by the ultrasound transducer (502), and the circuitry in the sub-electronics rack (6A) would record and process the peak signal (5004). Similar to the circuitry (6B) of the transponder (504), circuitry in the sub-electronics rack (6A) may have the measurements of all the signals received from transponder (504) and from the measurements the transducer circuitry (6A) may be able to identify a threshold magnitude, value, or transmission intensity for identifying that the peak signal (5004) is indeed a peak signal. In addition, circuitry in the sub-electronics rack (6A) may be configured to produce graphs of all the signals received from transponder (504) and from the graphs an operator may be able to identify a threshold magnitude, value, or transmission intensity for identifying that the peak signal (5004) is indeed a peak signal. FIG. 5G illustrates one example of a graph in which the intensity of the ultrasound signal (5004) from the transponder (504) may be determined as a peak signal. If the signal (5004) is a peak signal, then the logic circuitry in the sub-electronic rack (6A) would determine the time-of-flight from the initiation of signal (5002) to the reception of signal (5004). The distance between the transducer (502) or the ICE catheter (402) and the transponder (504) or the robotic catheter (404) may be determined from the time-of-flight. Since the sub-system electronic circuitry (6A) has a record of the line and plane of transmission of the transmitted signal (5002) related to the spatial position of the robotic catheter (404) relative to the ICE catheter (402), the additional information of distance from the ICE catheter (402) would enable the determination of substantially precise location of the robotic catheter (404) relative to the ICE catheter (402). As will be discussed further, the position, orientation, or localization of the ICE catheter (402) and the robotic catheter (404) in a spatial volume may be determined from the three-dimension map of the spatial volume. e.g., left atrium of the heart.

Referring back to FIG. 5E, the response signal (5004) from the transponder (504) may include various information or data about the robotic catheter (404); for example, the response signal may include but not limited to position, orientation, and shape information of the robotic catheter (404). Such information may be used to confirm the spatial position of the robotic catheter (404) relative to the ICE catheter (402) as well as its position, orientation, etc. a spatial volume such as left atrium of the heart. The distance between the ICE catheter (402) and the robotic catheter (404) may be determined or calculated from the time-of-flight of the transmitted ultrasound signal initiated from the transducer (502) on ICE catheter (402) and the reception of a substantially strong or peak response signal transmitted from the transponder (504) on the robotic catheter (404) by the transducer (502). For example, the distance may be determined or calculated by half of the time that would be required for transmitting an ultrasound signal initiated from the transducer (502) and the reception of a substantially strong or peak response signal from the transponder (504) by the transducer (502). As may be apparent to one skilled in the art, the electronics racks (6, 6A, 6B) are configured with all of the necessary hardware, software, and firmware for performing all the operations as discussed.

Figure 5H:
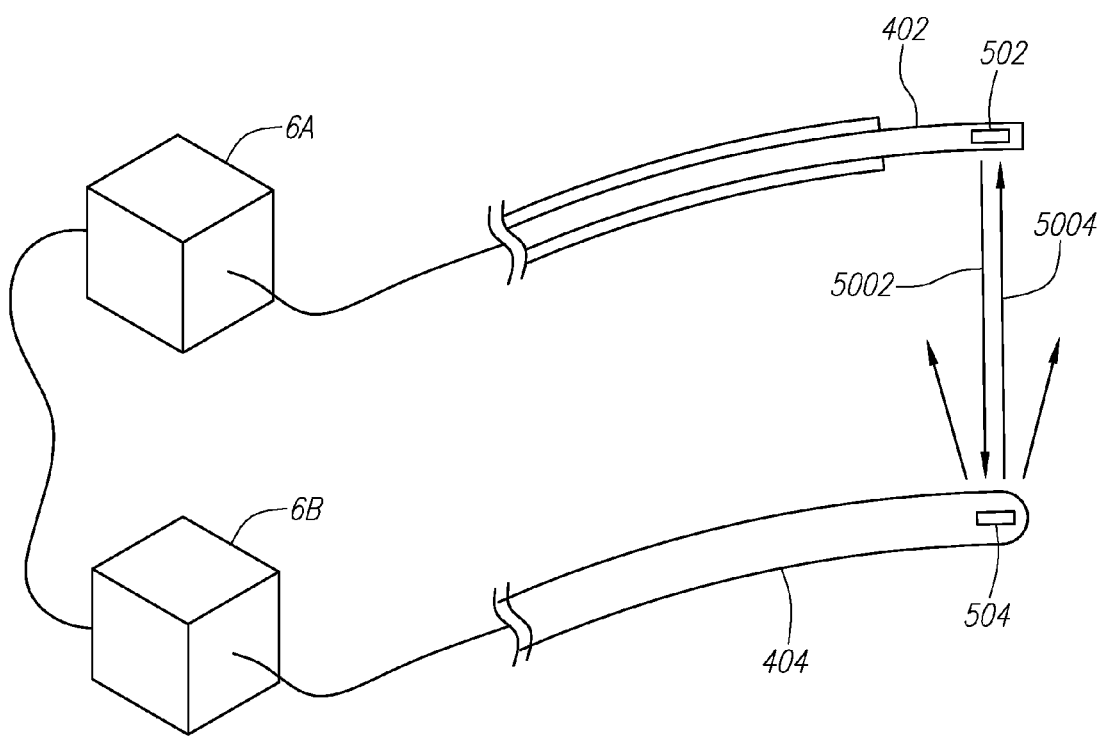
FIG. 5H another embodiment of an intracardiac echocardiographic catheter and robotic catheter system.

FIG. 5H illustrates another embodiment in which the transponder (504) is connected to hardware and software for determining the distance between the ICE catheter (402) and the robotic catheter (404). Similar to the discussion above, the transducer (502) transmits an ultrasound signal substantially directly to the transponder (504). In other words, the transponder (504) on a robotic catheter (404) is substantially in the direct path (line and plane) of transmission of the ultrasound signal (5002) transmitted from the ultrasound transducer (502) on the ICE catheter (402). In this embodiment, similar to the discussion above, the transducer (502) and the transponder (504) may be connected to hardware, software, firmware that are configured to distinguish an ultrasound signal that is transmitted directly to the transponder (504) from transducer (502). For example, the hardware and software may be configured to measure, record, and determine the strength, magnitude, or intensity of the received ultrasound signals from the transducer (502) and identify a substantially direct transmission as oppose to a substantially indirect transmission from the transducer (502). Because the hardware and software are coupled to both the transducer (502) and the transponder (504), they are capable of identifying and determining the initial time when a particular signal is transmitted substantially directly to the transponder (504) from the transducer (502). Based on the time-of-fire or time-of-transmission of the transmitted signal from the transducer (502) and the time-of-reception of the transmitted signal from the transponder (504), the time-of-flight may be determined. Accordingly, the distance between the transducer (502) or the ICE catheter (402) and the transponder (504) or the robotic catheter (404) may be determined from the time-of-flight of the ultrasound signal (5002).

Figure 6:
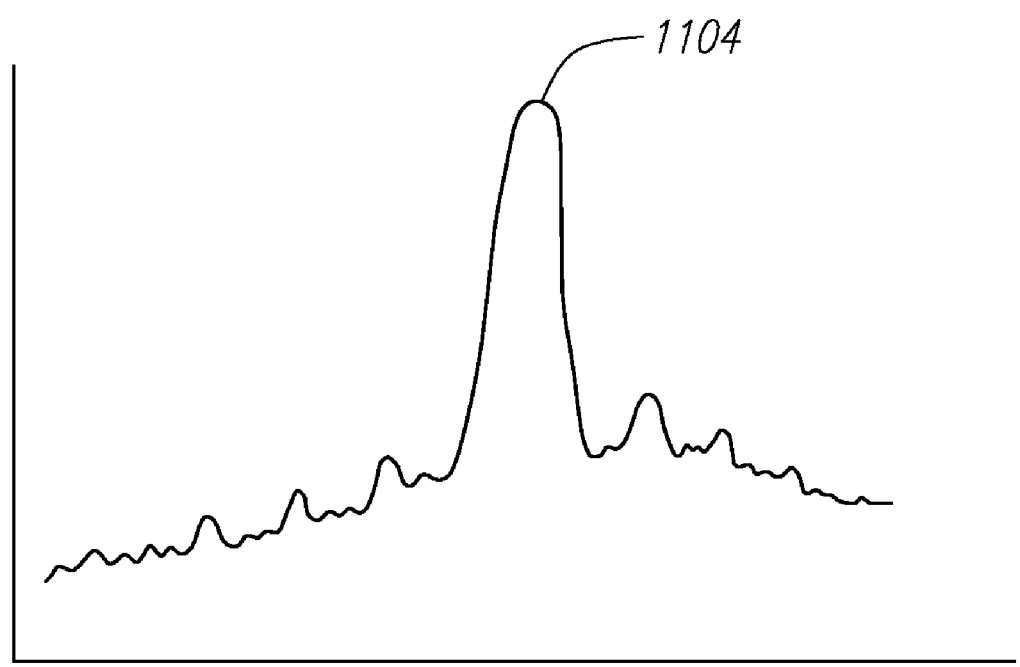
FIG. 6 illustrates another graph of ultrasound signals.

FIG. 6 illustrates the signal or insonified signal spike (1104) that may be produced and transmitted to the electronics rack (6) for processing to indicate that the robotic catheter (404) is in the direct line and plane of sweep of the ICE catheter (402).

Figure 7:
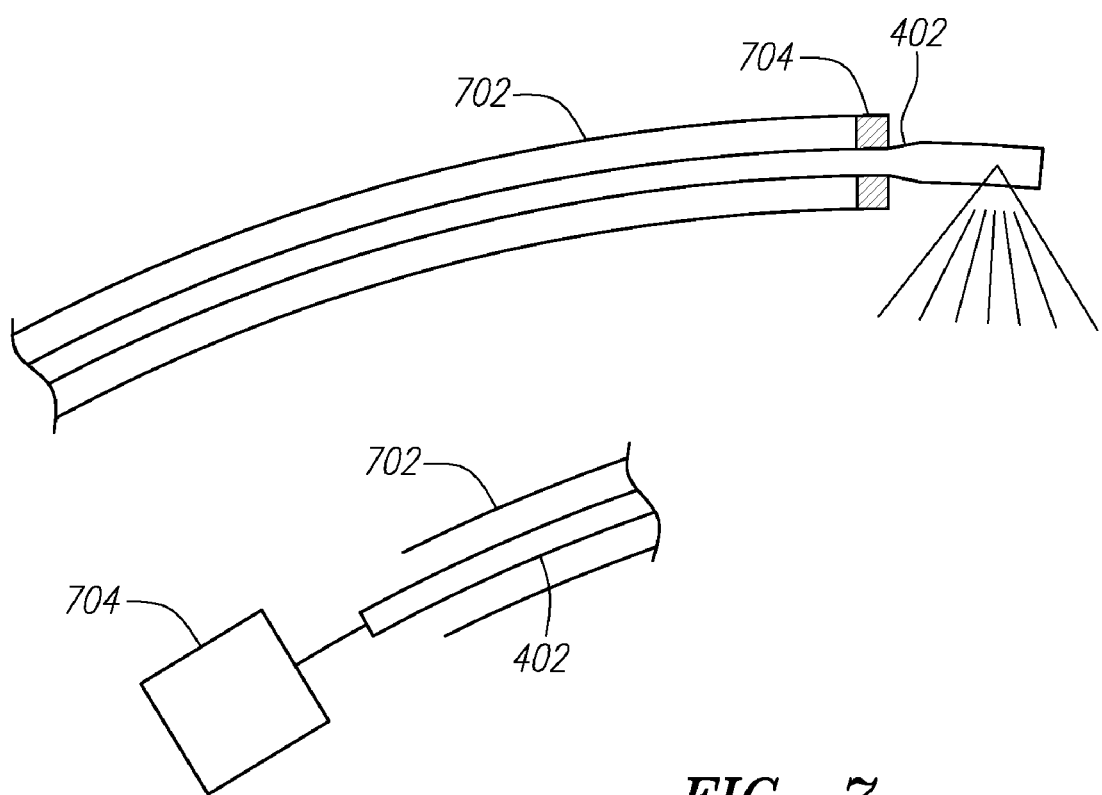
FIG. 7 illustrates one embodiment of an intracardiac echocardiographic catheter.

As can be appreciated, the transducer on the ICE catheter transmits lines of ultrasonic signals in a plane of transmission as the ICE catheter is rotated or swept by a rotational drive (704) as illustrated in FIG. 7. The rotational drive (704) may be controlled and monitored by the system hardware and software in the electronics rack (6). The system software may be programmed to identify the particular line or lines and plane or planes of transmission that cause one or more signal spikes as the ultrasonic signals are received by one or more transponders (504) coupled to the robotic catheter (404). By measuring the time-of-fire of the ultrasonic signal from the transducer (502) on the ICE catheter (402) and the time of reception of the ultrasonic signal from the transponder (504) on the robotic catheter (404) and calculating the time-of-flight of the ultrasonic signal, the system software would be able to calculate the distance between the ICE catheter (402) and the robotic catheter (404).

As can be further appreciated, the position, orientation, and localization of the ICE catheter (402) and robotic catheter (404) may be respectively determined by various means (e.g., shape sensing fiber optics, positional sensing monitors, etc.). Accordingly, the system hardware and software may compile and process all the respective localization information (e.g., the ultrasonic line and plane of transmission from the ICE catheter that caused the insonified signals; the distance between the ICE catheter and robotic catheter; and the position, orientation, and shape of the ICE catheter and robotic catheter) of the ICE catheter (402) and the robotic catheter (404) to produce a spatial relationship between the ICE catheter (402) and robotic catheter (404). In addition, as will be discussed in more detail, the ICE catheter (402) may be rotated (e.g., about 120 degrees or more) to produce two-dimensional intracardiac echocardiograms that may be "stitched" and filtered to produce three-dimensional maps of the heart. The information on the ICE catheter (402) and robotic catheter (404) may be combined with the three-dimensional map of the heart such that the spatial relationship of the ICE catheter and robotic catheter in a particular volume of space such as the left atrium of the heart may be determined and displayed.

FIG. 7 illustrates that the ICE catheter (402) is configured to be rotated by a rotational drive (704). The rotational drive (704) may be located near the proximal portion of the ICE catheter (402) and the sheath catheter (702). The sheath catheter (702) may be configured to provide certain amount of manipulation control, e.g., yaw, pitch, etc. A rotational bearing (704) may be operatively coupled to the sheath catheter (702) to facilitate separate or independent rotational movements of the ICE catheter (402). The rotational bearing may be located near the distal portion of the sheath catheter (702) to facilitate the rotational movements of the ICE catheter (402).

Figure 8:
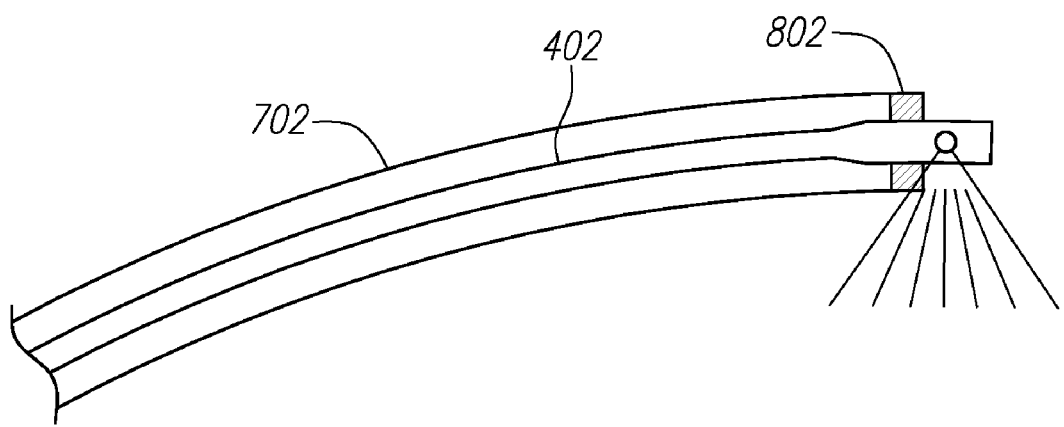
FIG. 8 illustrates another embodiment of an intracardiac echocardiographic catheter.

As illustrated in FIG. 8, a collar (802) may be coupled to the sheath catheter (702) near the distal portion of the sheath catheter. The ICE catheter (402) may be rotated within the collar (802). The collar (802) may include transponders or an array of transponders that are positioned along the circumstance of the collar (802). As the ICE catheter (402) is rotated, the transducer on the ICE catheter would interface with one of the transponders on the collar (802) as the transponder falls within the line or plane of transmission during the rotational sweep of the ICE catheter. The transponders on the collar (802) may be used as position indicators or angular indicators for the line or plane of transmission of the ICE catheter. In other words, the transponders on the collar (802) may be used to determine the angle of rotation of the ICE catheter (402) and the angular position of the line or plane of transmission. As will be discussed in more detail below, these information will be useful for constructing a three-dimensional map from the two dimensional intracardiac echocardiograms.

Figure 9:
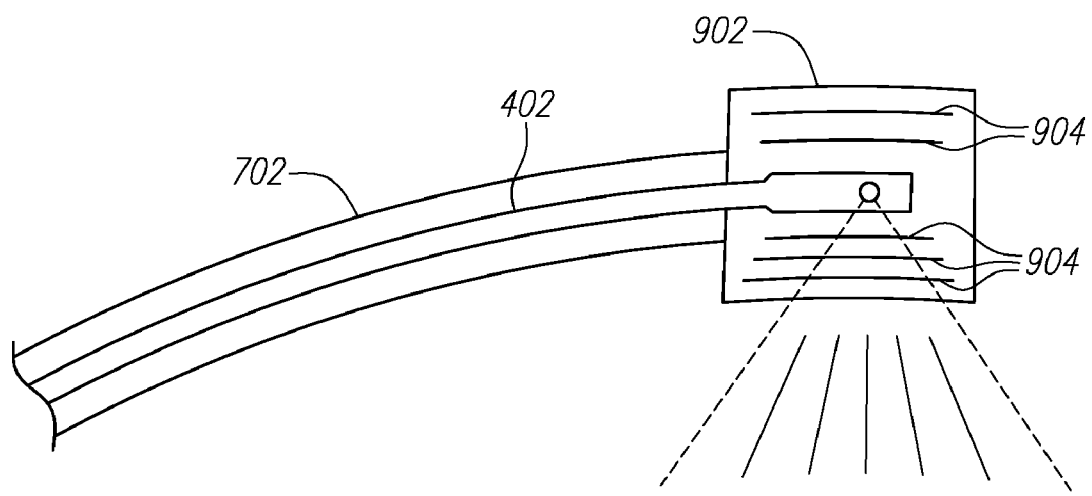
FIG. 9 illustrates a further embodiment of an intracardiac echocardiographic catheter.

FIG. 9 illustrates an ultrasound transparent cover (902) coupled to the sheath catheter (702). Generally, the transparent cover (902) does not interference with ultrasound transmission from the ICE catheter (402). However, the transparent cover (902) may include ultrasound opaque markers (904) along it circumference, such that the opaque markers (904) substantially interfere with ultrasound transmission when the line or plane of transmission crosses the markers. Accordingly, the opaque markers (904) may be used as positional or angular markers for identifying the angular position of the line or plane of transmission as the ICE catheter (402) is rotated.

Figure 10:
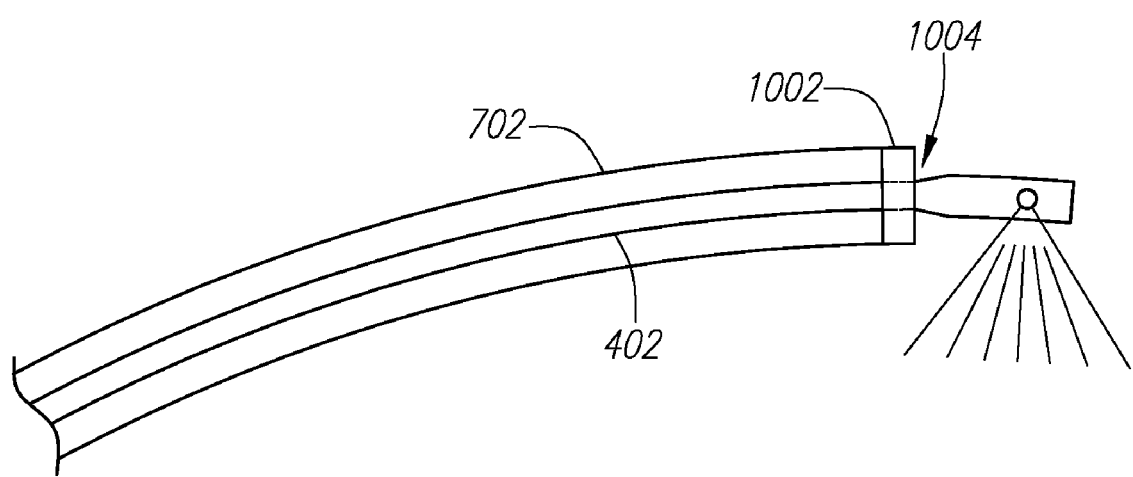
FIG. 10 illustrates yet another embodiment of an intracardiac echocardiographic catheter.
Figure 11:
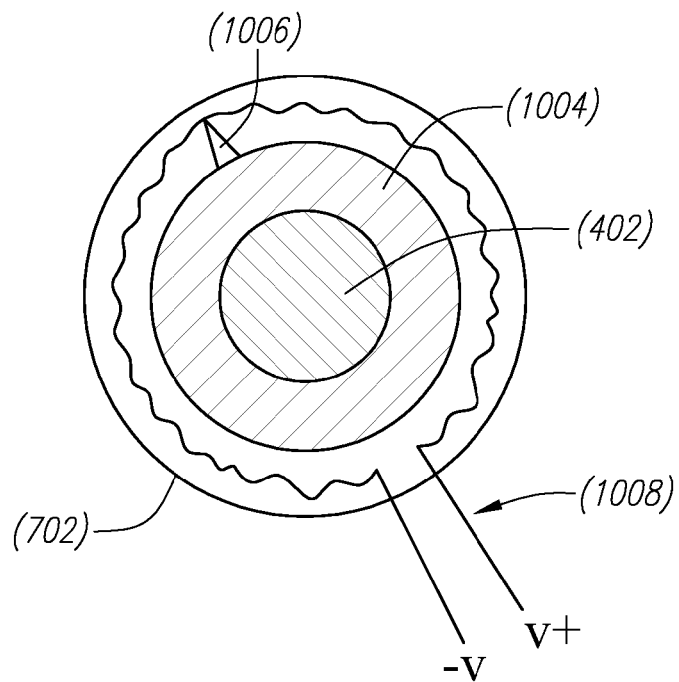
FIG. 11 illustrates a cross sectional view of one embodiment of an intracardiac echocardiographic catheter.
Figure 13:
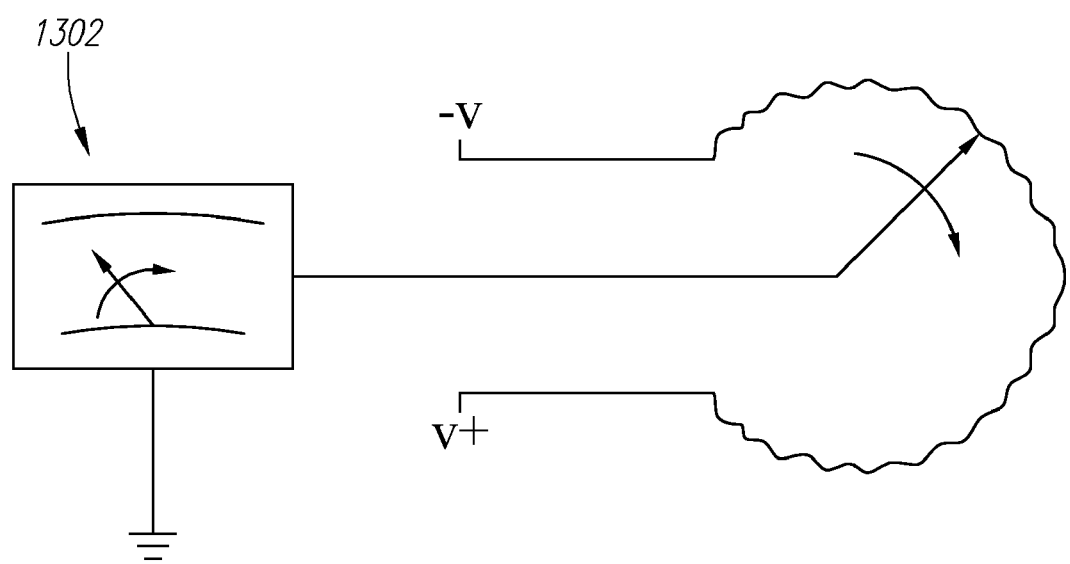
FIG. 13 illustrates an electrical circuit.

FIG. 10 illustrates a potentiometer system (1002) coupled to the sheath catheter (702). Alternatively, the interface between the ICE catheter (402) and the sheath catheter (702) may comprise an encoder (not shown) configured to detect rotation. The potentiometer system (1002) operates electrically for determining the angular position of the ICE catheter (402). FIG. 11 provides a more detail view of the potentiometer system (1002). The potentiometer system (1002) includes a rotational bearing (1004) that may be fixedly coupled to the ICE catheter (402) and rotatably coupled to the sheath catheter (702), such that the rotational bearing (1004) substantially rotates with the ICE catheter (402) within the sheath catheter (702). Referring to FIG. 11, the potentiometer system (1002) includes an electrical conductor (1008) coupled to the sheath catheter (702), and an electrical contact (1006) may be fixedly coupled to the rotational bearing (1004) which makes contact with the electrical conductor (1008), such that the contact (1006) and electrical conductor (1008) form an electrical circuit that drives a voltage meter (1302) as illustrated in FIG. 13. As apparent to one skilled in the art, based on the measured voltage and the resistivity (e.g., the inherent resistive property of the material, the length or amount of the material, etc.) of the conductor (1008), the angular rotation or position of the ICE catheter (402) may be determined. In some embodiments, instead of the potentiometer system, an electrostatic resolver or a magnetic resolver may be used to determine the angular position of the ICE catheter (402). For these embodiments, the electrostatic resolver or magnetic resolver might be operatively coupled to the sheath catheter (702) and the ICE catheter (402).

Figure 12:
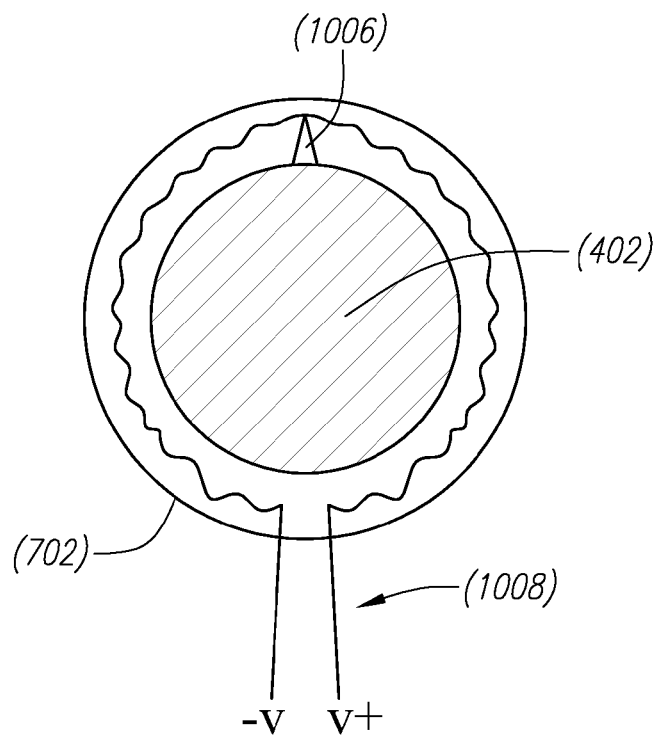
FIG. 12 illustrates a cross sectional view of another embodiment of an intracardiac echocardiographic catheter.

Following a similar engineering principle as the potentiometer system (1002), FIG. 12 illustrates another embodiment that configures an electrical contact (1006) directly on the body of the ICE catheter (402). Similarly, the electrical contact (1006) completes an electrical circuit with electrical conductor (1008) that drives the voltage meter (1302) as illustrated in FIG. 13.

Figure 14:
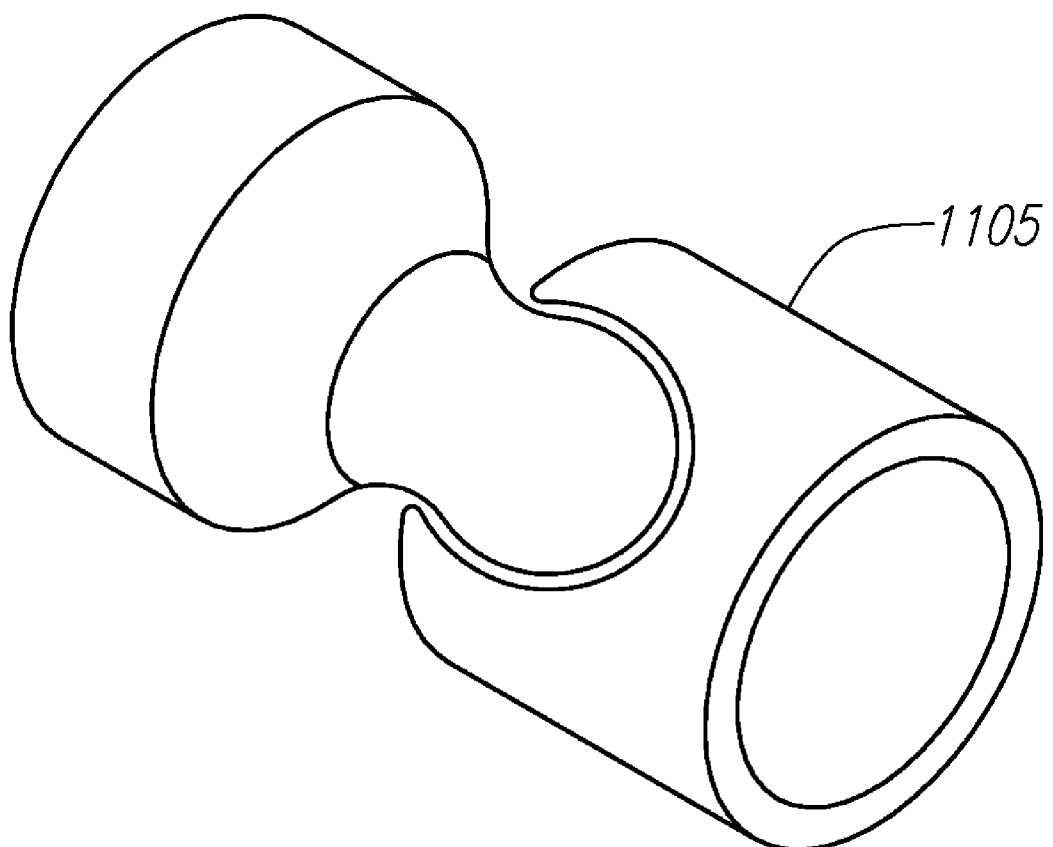
FIG. 14 illustrates portion of the body structure of an intracardiac echocardiographic catheter.

FIG. 14 illustrates a portion of the body structure (1105) of the ICE catheter (402). The segments of the body structure show that the ICE catheter (402) is substantially flexible in either pitch or yaw; however, it may be substantially rotationally stiff, such that the ICE catheter (402) may be rotated by the rotational drive (704) without any significant loss of angular movement or rotation from the proximal portion (e.g., input portion) to the distal portion (e.g., the output portion) of the ICE catheter (402). In addition, any loss or impact due to friction may be significantly minimized or eliminated by dithering ICE catheter (402). For example, the ICE catheter (402) may be dithered within the sheath catheter (702) or any lumen to significantly minimize or eliminate the effects of friction to the movements of the ICE catheter.

Figure 15:
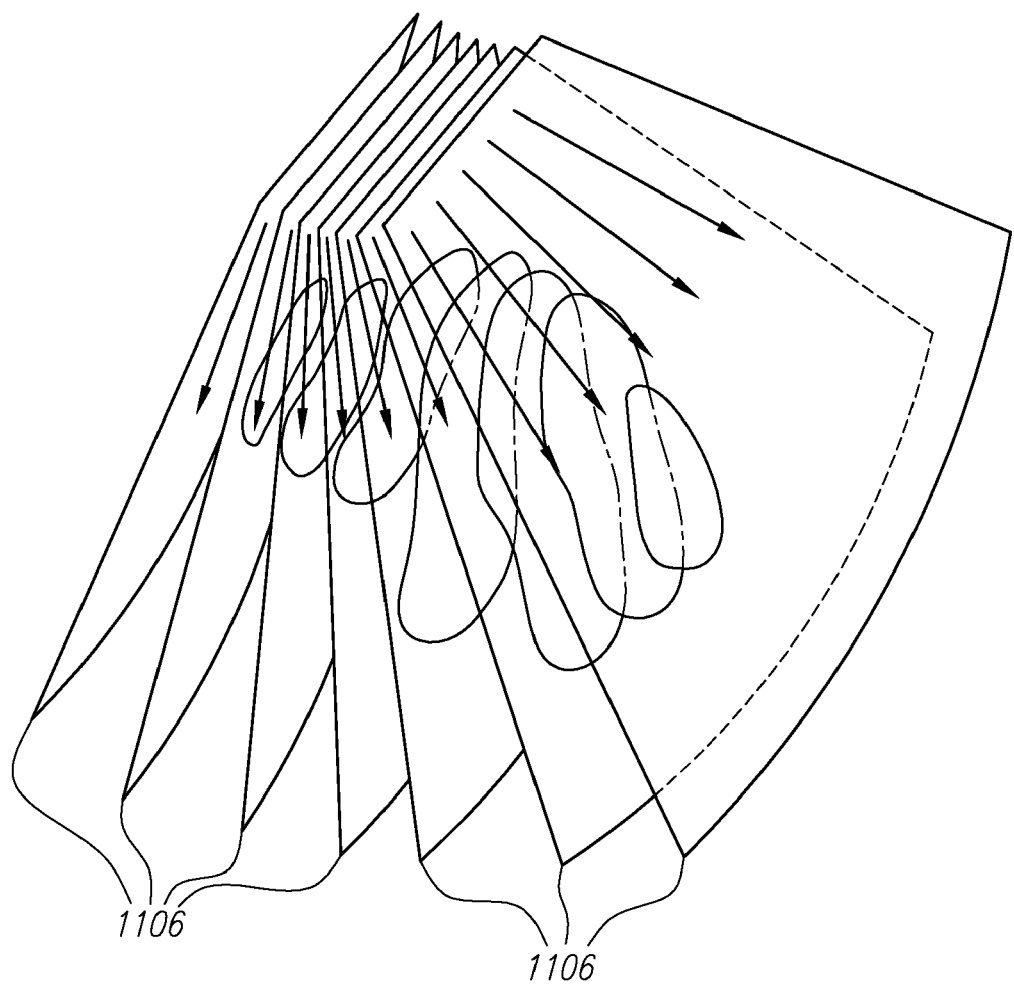
FIG. 15 illustrates two-dimensional slices of intracardiac echocardiograms.
Figure 16:
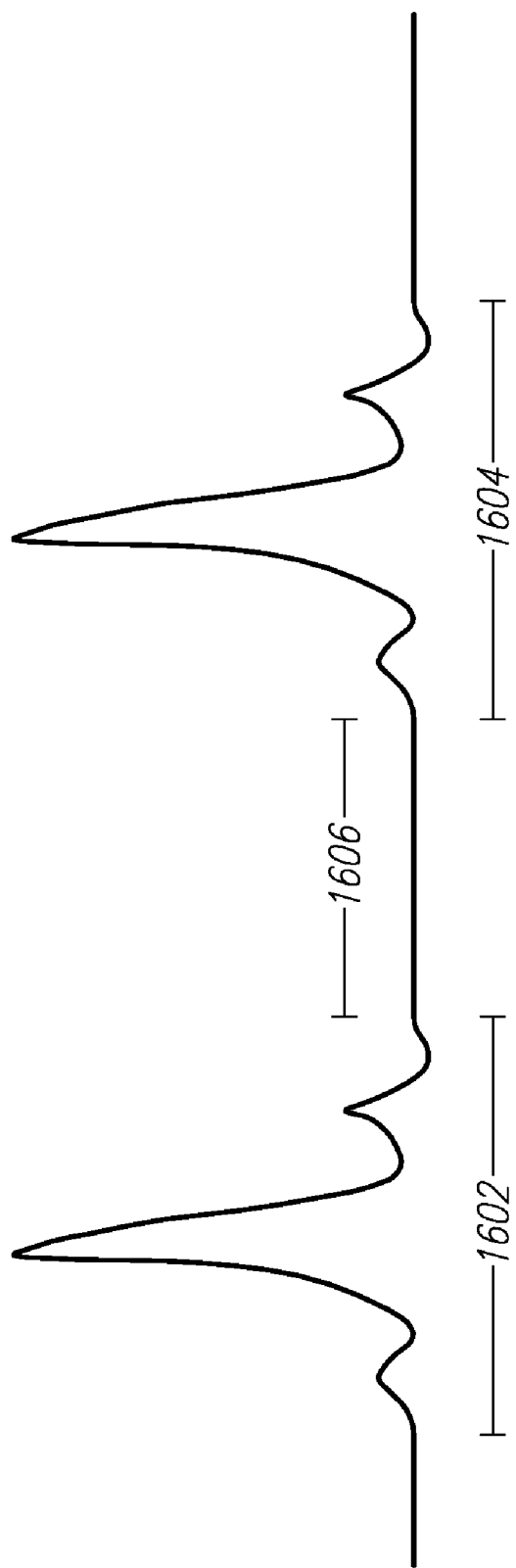
FIG. 16 illustrates a heart cycle.

FIG. 15 illustrates two-dimensional slices (1106) of the intracardiac echocardiograms of an organ in the patient that may be produced from the ICE catheter (402) as the ICE catheter is rotated. The intracardiac echocardiogram may show a complete organ, e.g., heart, stomach, kidney, urinary bladder, uterus, etc. or a portion of an organ, e.g., one or more chambers of the heart, a portion of the stomach, kidney, urinary bladder, uterus, etc. As will be explained in further detail, the two-dimensional slices of the intracardiac echocardiogram may be "stitched" or assembled together to produce a three-dimensional map of an organ, e.g., heart, or a portion of an organ, e.g., left atrium. To minimize the distortion of stitched three-dimensional map, the ultrasound image of the two-dimensional intracardiac echocardiogram may be taken during the rest period of relatively low heart activity or the diastolic period of the heart cycle. That is, the acquisition of an intracardiac echocardiogram may be gated by the periods of the heart or breathing cycles to substantially reduce or eliminate the impact of cyclic motions of the heart associated with these cycles. FIG. 16 illustrates a typical heart cycle of a healthy patient, wherein 1602 and 1604 indicate the two systolic segments of a heart cycle, and 1606 indicates the diastolic segment of a heart cycle.

Figure 17A:
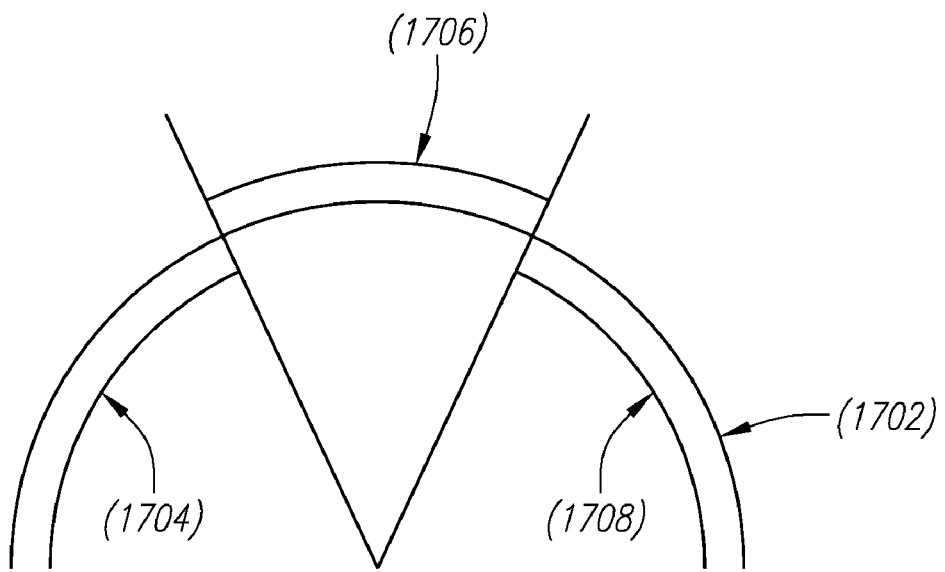
FIG. 17A-17C illustrate one embodiment of producing three-dimensional map of an organ in a patient.
Figure 17B:
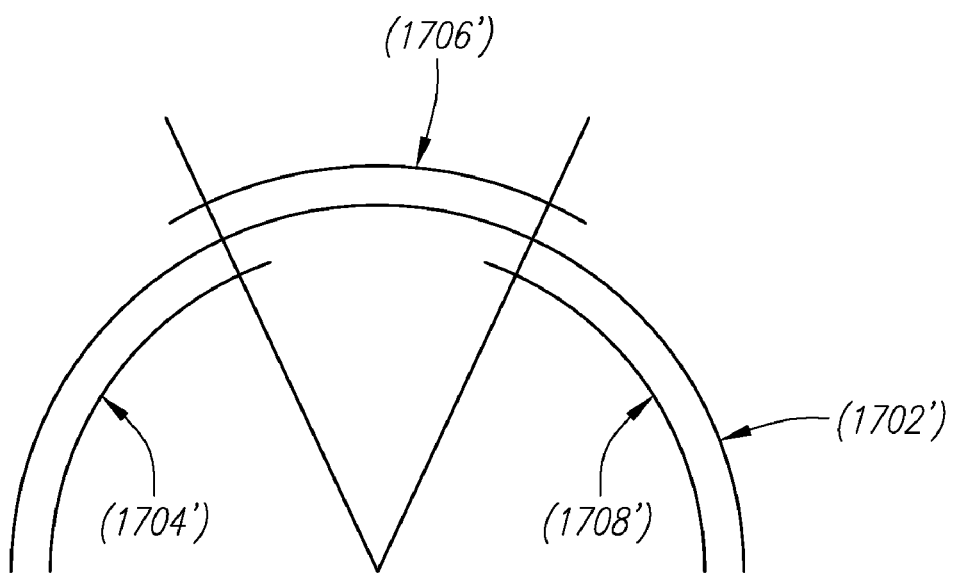
Figure 17C:
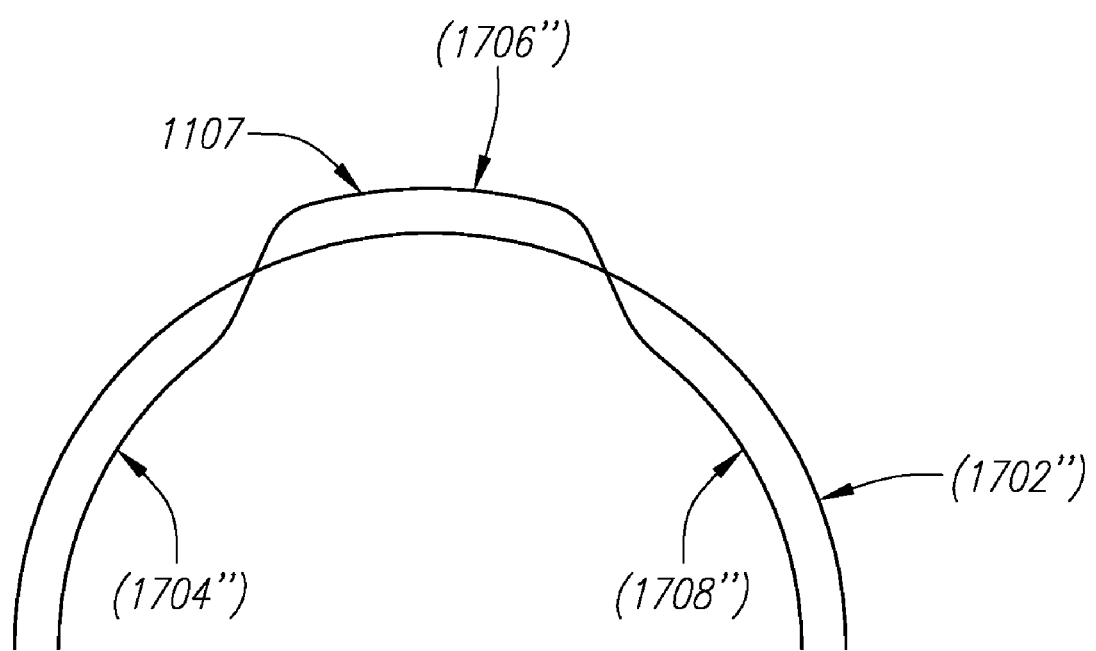

FIGS. 17A-17C illustrate one embodiment of stitching or assembling a series of slices of two-dimensional intracardiac echocardiogram by stacking overlapping images together to form a three-dimensional shape or map of the organ, e.g., heart, or portion of the heart such as the left atrium. FIGS. 17A-17C are cross sectional views of the stacked two-dimensional intracardiac echocardiograms. For example, as illustrated in FIG. 17A, a first portion of the surface (1704) of the heart may be captured by a first slice of intracardiac echocardiogram taken at some time T1, a second portion of the surface (1706) of the heart may be captured by a second slice of intracardiac echocardiogram taken at some time T2, and a third portion of the surface (1708) of the heart may be captured by a third slice of intracardiac echocardiogram taken at some time T3. As can be seen in FIG. 17A, the three surfaces (1704), (1706), and (1708) may not form a substantially continuous or smooth surface. Accordingly, a three-dimensional map produced by combining many substantially discontinuous or non-smooth surfaces, at the minimum, would appear distorted and may provide only limit utility to a surgeon who may be attempting to use such a three-dimensional map to accurately place an ablation catheter at precise locations of the heart to perform ablation therapy.

Figure 18:
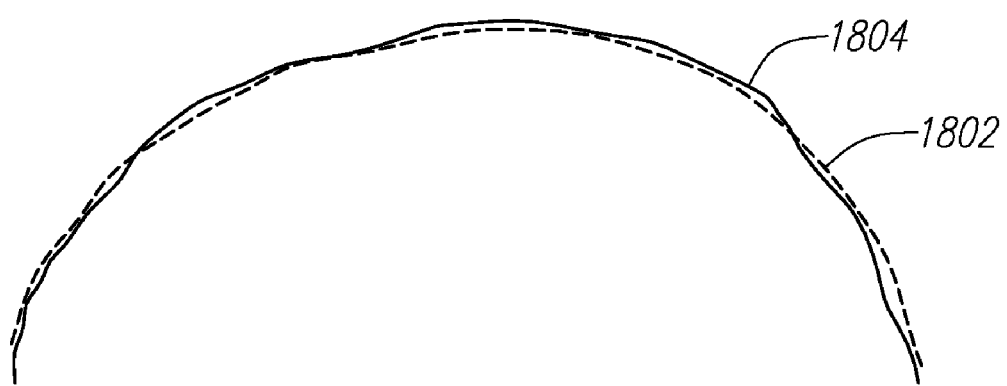
FIG. 18 illustrates a substantially continuous surface after a filtering process.

FIG. 17B illustrates the two-dimensional intracardiac echocardiograms are stacked together in a slightly overlapping manner, such that the first surface (1704') slightly overlaps with the second surface (1706'), and the second surface (1706') slightly overlaps with the third surface(1708'). Conventional filtering algorithms may be applied to the overlapping surfaces to substantially reduce, minimize, or eliminate the discontinuity to produce a substantially non-discontinuous or smooth surface for a three-dimensional map. FIG. 17C illustrates a substantially non-discontinuous surface after one or more filtering processes have been performed on the initially somewhat discontinuous surface the processed or filtered surface (1107) comprises of processed first surface (1704''), processed second surface (1706''), and processed third surface (1708''). FIG. 18 illustrates that further "smart" filtering may be performed to produce a substantially continuous or smooth surface of a three-dimensional map of an organ. The profile of the smart filtered surface (1804) is show with the profile an actual surface (1802) of an organ in FIG. 18. As illustrated in FIG. 18, the smart filtered surface (1804) is substantially continuous or smooth and substantially matching the surface profile of the actual surface (1802) of the organ.

Figure 19:
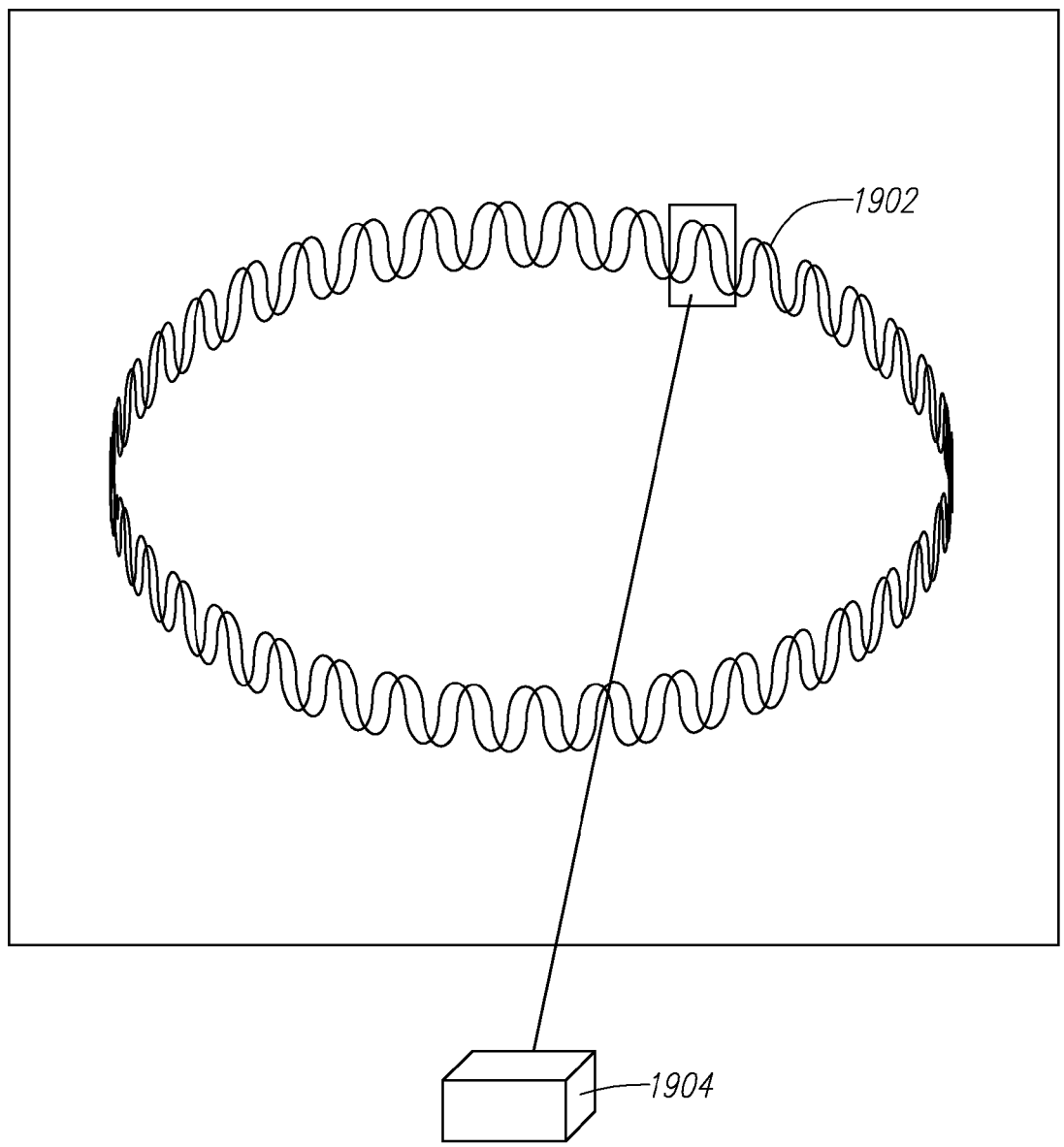
FIG. 19 illustrates a two-dimensional intracardiac echocardiogram.

FIG. 19 illustrates a two-dimensional intracardiac echocardiogram or a cross sectional view of a three-dimensional map produced by stacking two-dimensional intracardiac echocardiogram. As illustrated in FIG. 19, a surface (1902) of an organ as shown in a typical intracardiac echocardiogram does not have clear and distinct boundaries. Instead, the surface may be discerned by clusters of pixels. Another method of producing a three-dimensional map of an organ, e.g., heart, or portion of an organ such as the left atrium of the heart, is grouping the pixels into voxels (1904) or volumetric pixels (1904) and then filtering the voxels (1904) or volumetric pixels (1904) by performing segmentation methodology or algorithm on the voxels to produce a mesh surface for the three-dimensional map of the organ. The threshold for segmentation may be in the range about 3 mm to about 5 mm.

Figure 20:
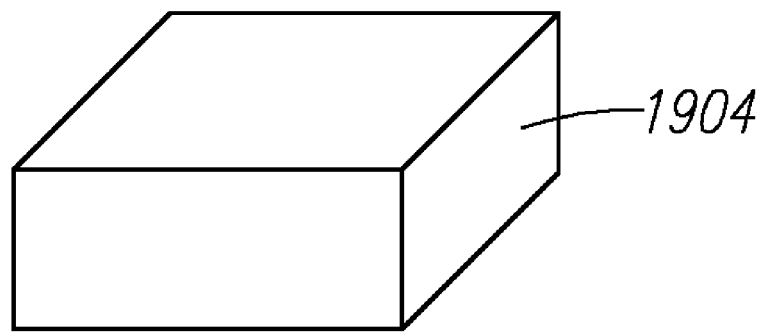
FIG. 20 illustrates a process of using a segmentation algorithm to produce a mesh surface.
Figure 20:
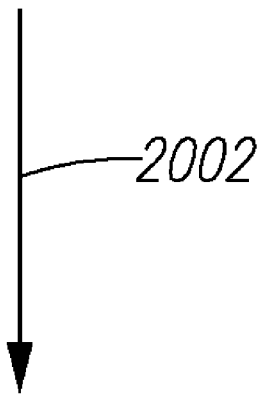
Figure 20:
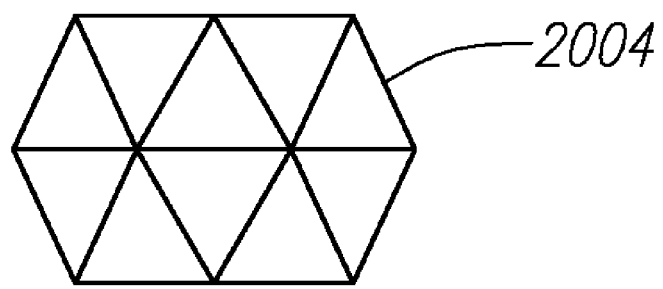

FIG. 20 illustrates a process of using a segmentation algorithm to produce a mesh surface. As illustrated in FIG. 20, voxels (1904) or volumetric pixels (1904) may be filtering by using a segmentation algorithm (2002) to produce a mesh surface (2004) as a portion of a three-dimensional map.

Pre-Processing of Voxel or Pixel Data Before Segmentation:

(a) Conventional filtering techniques such as linear filtration, nonlinear filtration, morphological filtration (filtering based upon predetermined shapes) may be utilized to filter raw data comprising, for example, voxel or volumetric pixel data, before processing with segmentation algorithms; other filtering techniques may also be applied to refine the raw data before segmentation, such as Gaussian low pass filtration.

(b) To decrease ultrasound "speckle", conventional "compounded scan" techniques may be utilized wherein the capturing transducer is moved slightly to acquire a similar field of view from a different position, in one embodiment accomplished via precision robotic movement of the imaging platform assembly (e.g., 402) after a first round of raw data acquisition.

(c) The same structures may be imaged and captured multiple times from the same or different transducer location, then combined to filter out imperfections, etc. using localization data, knowledge of fixed structure reference points, etc. to improve the quality of the image before segmentation.

(d) Subsequent to capture and assembly of image data for a subject volume of interest, discrete portions may be imaged again at closer range, or in a repeated fashion from the same or different position, to increase the quality of the image data at such portions. For example, in a left atrial electrophysiology scenario, the four pulmonary vein ("PV") entrances are of significant interest and would preferably be selected for increased quality image capture using such technique.

(e) Notwithstanding gating techniques to accommodate movement of the heart, diaphragm, etc, certain portions of structures of interest may be imaged throughout such movement cycles and the arrays of images versus time associated with the otherwise gated raw data for the surrounding structures. For example, in the right atrium, gated acquisition of data may be utilized to produce a volumetric raw data representation of the right atrium, while more than one image versus time may be captured of a particular structure of interest, such as the tricuspid valve, to enable the operator to visualize the valve versus time in the form of a short "movie" of processed images of that region which is associated with a subsequently segmented model of the right atrium, or collection of voxel data of the right atrium. In other words, the operator would be able to visualize the entire right atrium for one period of time given the gating, but would be able to visualize the movement of the discrete region versus time given the extra data acquired versus time for such region.

(f) Enhanced threshold processing may be utilized to highlight pertinent structures of interest in a given voxel of pixel collection before segmentation. For example, utilizing parameterized inputs from various sources (such as preoperative CT or MR imaging, preoperative or intraoperative ultrasound, fluoroscopy with or without contrast agent injection, velocity/Doppler information from ultrasound, etc.), the operator, or if automated the system, may determine shapes, curves, or other descriptors that should be sought out in the raw data before segmentation. For example, given the knowledge of the approximate maximum diameter, approximate centroid of flow velocity, and roughly elliptical geometry of the four PVs coming into a given left atrium, a collection of ultrasound data for the volume defined by a left atrium may be thresholded with different thresholding values and different cutting planes through the raw data to locate each of the four PVs, and preferably other valuable information, such as the location and orientation of the plane which best fits each of the four semi-elliptical PV entrances into the left atrium; similar technique may be used for analyzing other surfaces or structures other than the PVs before and/or after the first round of segmentation to produce a surface model.

Segmentation to Form Surface Model:

(a) Conventional segmentation techniques may be utilized on an entire set of raw data to produce a solitary surface model, or several sub-portions of the raw data set may be segmented to produce several surface models, which may be combined with joining or stitching techniques.

(b) Parameterized modeling may be utilized to improve the results of segmentation. For example, maximum geometries and general shapes of objects within the raw data may be known and utilized to improve the segmentation algorithm processing and results.

(c) For raw data acquired versus time, ("4-D"), parameterized modeling and differential equations in time may be utilized to represent moving segmented surfaces. Alternatively, discrete point based techniques, such as particle filtration techniques, such as those described in the publication "Particle Filter with Analytical Inference for Human Body Tracking", IEEE Workshop on Motion and Video Computing, November 2002, Florida, may be utilized to analyze the motion of points relative to neighboring points, to represent moving surfaces, and this publication is herein incorporated by reference its entirety.

Subsequent to a First Round of Segmentation:

(a) Additional newly acquired data slices or images may be utilized to fill out the first round segmented model. Such new data may be integrated into the pre-processing and the whole volume or region re-processed, or the new data may be separately processed, segmented, and integrated into the first round surface model using averaging, interpolation, parameterized smoothing, or other techniques.

(b) Indeed, parameters found from the first round processing may be utilized to improve the results of second round processing. For example, given a first round understanding of the surfaces of the four PVs of a given left atrium, the raw data may be re-processed before segmentation in a different manner (for example, different thresholding values or cutting plane orientations, different parameter variables as inputs to thresholding, etc), different filtration, or other variations of the aforementioned pre-segmentation treatments of raw data, to produce an improved second round segmentation product.

(c) Furthermore, the combination of localization and ultrasound-based mapping of a volume, with variations in the quality of data coming from each modality given variables such as time, nearby magnetic localization interference from ferromagnetic materials, etc., presents the opportunity for what has become known as "SLAM"—or simultaneous localization and mapping—a term used in reference to the utilization of the strengths and weaknesses of the two modalities to produce a net imaging understanding better than the product achievable with either one by itself. For example, if it is known that the subject electromagnetic localization modality is generally more accurate in determining relative spatial positioning than is ultrasound-based image or surface model processing techniques for determining relative spatial positioning, with the exception of the case where a strong magnetic interference is present from a nearby ferromagnetic structure, such as a fluoroscopy C-arm support assembly, then the system may be configured to weigh the localization-based spatial positioning data more heavily except in regions of high magnetic interference—the integration of the two modalities producing a more accurate result than either individually.

Alternative Method:

(a) Use the imaging assembly (e.g., 402) and localization data from the second assembly (e.g., 404) to automatically have the imaging assembly and the pertinent imaging assembly transducer field of view follow the second assembly and some designated slice of volume on each side, in addition to capture of the second assembly (e.g., 404) distal portion.

(b) Optionally fly in a cartoon object on the display to overlay an imaged catheter or instrument. For example, if a system operator was looking at a lasso catheter with known dimensions and electrode positions, once the operator has located the relatively fuzzy image of the lasso using the ultrasound techniques, overlay a clean cartoon of the lasso for better operator interpretation.

(c) When iterating to improve the entire surface or portions thereof, one may completely go back to voxel data and re-segment or segment only new data and mesh the new data into the previous surface, etc.

(d) There may not be any need to capture in raw data every bit of a subject volume. One may capture certain portions, perhaps certain planes, regions, etc., and have these data represented either as voxel groups with gaps in between to be segmented as a whole or left as voxel data with gaps (and perhaps stitched or joined together using conventional techniques), or as separate voxel sets to be segmented individually, and perhaps combined using conventional stitching or joining techniques. Generally it will not be the case that one has the time or need to acquire a completely spherical, etc dataset—it is more desirable to image what is pertinent and spend one's processing power and time on that.

(e) One may start out with a simple parameterized model. For example, an "atlas model" or generic model of a piece of anatomy such as the left atrium, and then build out the model by utilizing the data captured from ultrasound. In other words, it is not necessary to start with no model and generate the very first model by segmenting the raw data. One may use parameters, anthropometric data, etc. to start with a starter model, and build out/integrate the model from there using captured data from the actual anatomy.

(f) SLAM: localization is not perfect; either is ultrasound; notion in robotics is "simultaneous localization and mapping"; use both systems to help each other; the measurements have random noise; over time, one can hone in on things and improve by averaging out the noise in both localization and mapping sensors; get a better result; works for robots navigating hallways, undersea robotics where GPS data is imperfect, etc. In one embodiment, SLAM techniques may be utilized with a system such as those depicted in FIG. 5E or 5H for building a map, and at the same time, utilizing this evolving map to understand where the various instruments are positioned within the map. It is a sort of common filter wherein one may utilize the data one has and continue to refine one's database and utilize statistical and/or information weighting techniques. In a preferred SLAM embodiment, the system may be used to build a map and localize the instrument or instruments in the heart without having a preexisting map or localization sensor. It may be useful in scenarios wherein the kinematics model utilized to operate the instrument or instruments is not entirely accurate but is adequate for safely navigating to build a map using such techniques.

(g) One can also track other catheters that might not have sensors on them—or sensors such as inertial sensors—to improve one's knowledge of where those instruments may be located.

(h) The ultrasound acquisition in the above examples and embodiments may utilized fast sweep ultrasound techniques (as disclosed in the abovementioned patent application, Ser. No. 10/923,660), or conventional slice-by-slice acquisition over a series of heart cycles, for example.

(i) One example of a sample protocol for electrophysiology intervention in the left atrium:

(1) Perform the first round of sweeping using roll of the robotic catheter assembly (or roll of just the ultrasound catheter) along with whatever steering, bending, insertion, yaw, pitch, etc. are valuable to create a large voxel map of the pertinent volume and structures of interest (such as interventional tools, etc.); would likely using gating for heart motion, although it would be useful for at least certain structures to acquire data versus time for 4-D analysis.

(2) Pre-process the data, pixels, or voxel (using various combinations or permutations of the above options) and then perform segmentation to build surface. It may be desirable to build one big surface model, or build subsurfaces for different regions and potentially stitch or assemble them together.

(3) Then it may be desirable to iterate or acquire additional raw data to fill in details for pertinent structures/issues—e.g., for PVs and left atrial appendage; locate them with various techniques; perhaps use Doppler analysis and/or thresholding; one may obtain a large set of voxel data—ideal plane for thresholding may not be obvious—but one can do multiple planes and search for shapes, etc.; this may be optimized, parameterized, and automated. For example, one may take a plane for each of the PVs (based upon your knowledge of generally where they are in the stack and their general shape), and smart threshold each one; perhaps go back and gather more raw data for some particular areas. Since one knows approximately where the PV of interest is, one can use the robot to get substantially good angle of approach, etc.

(4) Continue to iterate by collecting more data and processing it into the surface model, or keeping it as raw data in the voxel world for examination/analysis there.

(j) Embodiment of a scenario for heart chamber use of a system such as those depicted in FIGS. 1011A or 1011B, such as in the left atrium:

(1) Take a 3-D scan of the atrial space at the start of the case using a configuration such as that depicted in FIG. 5E or FIG. 5H. Scan or shoot from the right atrium ("RA") over toward the left atrium ("LA") with a 30 degree fast sweep roll of the ultrasound field of view ("FOV") to assemble a stack of slices, or voxel data. Have other localized catheter assembly (e.g., the second assembly 404 of FIG. 5E or FIG. 5F) with a point reflector [or alternatively one or more reflecting coatings or structures, such as microspheres, positioned along, in one variation in a detectable graduated measurement format, the second assembly 404 for preferably clear ultrasound depiction of such assembly relative to other structures], etc. sitting right in the FOV of the ultrasound scan from the other assembly (e.g., 402)—which is designed and configured to be capable of doing this; then one may have 3-D dataset which includes the RA volume as well as the tip of the second catheter assembly.

Regarding initially lining up the ultrasound FOV to capture the desired volume—a basic technique may be to get the working catheter assembly (404) into position utilizing fluoro, then bring the FOV of the ultrasound catheter assembly (402) into position where it can capture the working catheter (404); or use combination of fluoro (to get the ultrasound catheter assembly (402) and working catheter assembly (404) generally into the right place—in one embodiment waggle each assembly (402, 404) back and forth in fluoro to get pitch and yaw lined up—then use real-time ultrasound to get the ultrasound FOV into position.

Alternatively one may register a segmented CT model into the navigation interface, then drive, steer, and/or advance the ultrasound catheter assembly (402) into position in the CT model (associated with localization, inverse kinematics, etc.).

Alternatively, one may just capture everything around the ultrasound catheter assembly (402) in a series of ultrasound images positioned 360 degrees, or a portion thereof, around such assembly (402), the images including the working catheter assembly (404), and register to the position of the localized (or kinematics-model-localized) working catheter assembly (404).

(2) Then one may segment and fly the segmented ultrasound data, or simply unsegmented voxel data, onto the user interface cartoon view of the second catheter assembly (without moving this catheter) in multiple views [could do manually, or could have a localization sensor on the ultrasound catheter platform and do automatically] and one may register the ultrasound model to the catheter cartoon. Subsequently, one may drive the cartoon around relative to the ultrasound model in the user interface.

(3) In another variation, once one is able to navigate the cartoon and/or other view (e.g., fluoro view) of a catheter instrument around in the user interface with the registered and scaled 3-D ultrasound model on the same display, one may present data on the ultrasound model. For example, in one embodiment, it is desirable to monitor electrophysiological isolation and project data upon the ultrasound model (for instance, when a second catheter assembly, such as 404 depicted in FIG. 5E or FIG. 5H, is utilized to touch points of the left atrium, the user interface may be configured to leave points with numerical and/or gradiently colored information at such points on the ultrasound model to depict an electrophysiological isolation scenario in an information-rich display).

(k) When the calculated and/or displayed difference between commanded catheter position and actual catheter position (based upon localization, multi-planar analysis of fiducials, etc.) becomes too great, this delta may be interpreted as collision between the catheter and a structure such as a tissue wall. Indeed, the kinematics of the catheter may be utilized to estimate force of such collision based upon the difference. In one embodiment, one may add haptics to provide an indication of the contact and/or force feedback to the user. One may also scale up the haptic load to the user with an increased difference between commanded catheter position and actual catheter position to "drive" the operator's navigation of the catheter back to a point of very light or no contact.

(1) An additional localization sensor positioned near the subject localized instrument or instruments may be utilized as a valuable tool for interpreting or analyzing localization data associated with an instrument placed within the body. In one embodiment, a reference sensor may be adhered with a patch or suture to the skin of a patient to work as a common mode filter—to decrease noise from things in the operating room such as magnetic field variations which may be associated with nearby ferromagnetic structure (such as a fluoroscopy C-arm), detect movements of organs, etc.

Indeed, the use of two localization sensors at different locations on the same deformable member (such as a catheter body), along with the known kinematics of such deformable member, to detect contact and force, can be highly accurate. Such differential measurement is a preferred technique and can be much more accurate than absolute measurement/calculation of contact and/or force utilizing an absolute measurement of, for example, instrument tip deflection relative to the operating table.

(m) Data processed and displayed by advanced CT and/or MR systems may be voxel data which is subsequently segmented into one or more surface models. That surface model conventionally lives on the imaging system. In one embodiment, such model is moved to the subject robotic catheter system where it is scaled, oriented, and registered so the operator may navigate the robotic catheter around in it in the user interface, haptically feel the model through the master input device, perform reachability analysis, utilize an interpreted motion logic layer, and/or conduct instrument path or trajectory planning and/or automation analysis.

CT and MR imaging typically imply gating to deal with motion artifacts. One significant advantage of the ultrasound system and techniques described herein is that one can acquire real-time and not be tied to a specific window of gating. One can be driving on a 3-d-versus-time (or "4-D") movie made from the ultrasound data. If one really want to avoid certain nerve bundles or other structures, this kind of data is very desirable—or at least the ability to switch from dead CT model mode to live ultrasound model mode when navigating near critical structures.

Models created with MR or CT imaging modalities may be registered into the navigation interface of the subject robotic catheter system by having an experienced physician put the catheter at an anatomic landmark using fluoro ("ok—I know I am at the X"). One may then fly the CT or MR model around and scale it into registration. After a few points, the system may be configured to "snap" the model into registration. One can use as much information as one have, such as SLAM type analysis (simultaneously improving one's map and one's knowledge of location)—use everything one know—may be utilized.

(n) Regarding integration of magnetic localization sensors such as those available from manufacturers such as Ascension Technologies:

(1) Certain structures comprising variations of robotically-steerable catheters of the subject system, such as metallic braids or tubular metallic structures may interfere with magnetic fields and work as variations of a Faraday cage for localization sensors placed within the working lumens of such robotically-steerable catheters—so it may be desirable to advance the sensor portions past such catheter structures.

(2) The leads for electromagnetic localization sensor structures may be floated in lumens for stress relief, layered into the subject catheter, braided or woven into the subject catheter, etc. Such leads (and/or sensors) may need shielding or heat protection, which may be handled utilizing layers or material, such as heat shrink material, to at least partially encapsulate such leads—and/or portions of the associated sensor or junction between the sensor and leads. In one embodiment, a 5-degrees-of-freedom sensor is preferred for catheter structures such as those depicted in FIGS. 5E and 5H;

(o) Thresholding values of voxel data can have a significant impact on models resulting from segmentation of the voxel data. In one embodiment, the subject voxel data is thresholded at multiple different values—e.g., three with a fairly broad range of expected desirability. Subsequently, all of the thresholded voxel data may be segmented, and whichever depicts the subject tissue and other instrument structures most desirably may be utilized. This embodiment requires more data processing, but can be very valuable given the significant impact of thresholding value on the ultimate model results.

(p) Injection of contrast agent may be utilized to develop a volume or voxel data set for a volume of interest; for example. In one embodiment, a quick shot of contrast agent into the calices of a kidney may be immediately followed by single or multiplanar imaging to build a quality dataset representing the pertinent volume of the kidney with contrast sufficient for accurate thresholding at the voxel level and post processing and/or segmentation to produce a surface model associated with the volume.

(q) Electromagnetic localization and associated ferromagnetic field issues:

Ferromagnetic structures (such as metallic fluoroscopy C-arm which may be instrumented with an inclinometer or other angle sensing device) may disrupt or alter the accuracy of electromagnetic localization systems such as those available from suppliers such as Biosense Webster or Ascension Technologies, Inc. Several techniques may be utilized to preserve the accuracy of such systems when adjacent to ferromagnetic structures.

(1) Create an operating table environment based lookup table for magnetic localization distortion versus position of the C-arm (or other ferromagnetic structure). For example, use the edge lines of a cube-like structure, and take a number of readings with localized catheter on one line of testing cube with C-arm moving all around. Following the same procedure, the next line of the cube, and continue with all 8 lines of the cube. Using the collected data, develop a lookup table to transform raw localization data into C-arm-compensated localization data which may be more accurate. Then, the lookup table may be utilized in subsequent operation of the system with a patient to compensate for the C-arm position.

(2) Similarly, one could have a vest (to be wore by the patient) or other structure for positioning a series of localization sensors (e.g., 4) adjacent a patient's chest (for a cardiac catheterization procedure; other anatomic region may be more pertinent for other procedures) and a separate localized catheter (e.g., 5 total sensors in this example). Then, in a similar fashion as discussed above, move the C-arm or other structure through various positions relative to the sensors and create a lookup table. In one variation, start by capturing a series of localization readings without the C-arm near the sensors at all, and then bring over the C-arm to develop an understanding of how the C-arm affects the localization data.

(3) Alternatively, one can utilize multiple planes of fluoro shots, along with the associated inclinometer data, to calculate precise position of sensors without the C-arm in the environment. Then one can analyze localization data for the same positions when moving the C-arm around in various positions and create a compensation lookup table.

(4) Alternatively, optical fiducials and multi-planar imaging (with inclinometer data, etc) may be utilized to precisely localize one or more sensors, and this precise data may be compared with readings as disrupted by a C-arm or other structure in various positions to develop an understanding of how to compensate for the C-arm position in the localization data.

(5) Pre-op calibration with sensor on catheter:

Without a vest or cube, the catheter by itself with an electromagnetic ("EM") localization sensor on its tip may be used to create a lookup table. The catheter is inserted into the patient then placed at an extreme point of a workspace and the C-arm takes a reading now having the instant location of the tip. The catheter is then moved to several different points defining the extreme limits of the workspace with a C-arm reading taken at each position. This data is compiled into a lookup table.

This pre-operative calibration doesn't have to be with the subject robotic catheter system.

(6) Calibration of the room or system:

Another perspective is to not create a lookup table for a workspace but create a lookup table for a particular operating room. The operating table itself can have fiducials and readings with the C-arm can be taken of the table as it is moved back and forth.

The localization sensor is calibrated to an alternative sensing means assumed to be accurate and reliable. The reliable sensor can be, for example, fluoroscopy or a mechanical setup jig.

A very large lookup table may be created in an operating room on the bench-top in an automated fashion to slowly step the catheter with an EM localization sensor on its tip through hundreds of positions. The C-arm may take a reading of each position. Such process may take a relatively long period of time but be completed only once to the system for a given configuration. One may have a read position from the C-arm matching the known kinematic position based on the positioning of a given instrument or instrument set, such as a robotic catheter system. Thus a lookup table would then be very detailed and could be used as an accurate calibration or transformation means during a procedure.

In this case the relative location and orientation of the table may be found using a variation comprising fiducials associated with the table. This gives a position of the C-arm without influence of the distortion that the metal in the table (or C-arm) may cause during an electromagnetic reading.

(7) Calibrating fiducials:

In some embodiments it is desirable to have permanent fiducials to calibrate various things.

Using line fiducials (or patterns of lines, dots, etc—which may comprise lead or other radio opaque materials in the case of fluoroscopy) detectable with optical cameras, fluoroscopy, etc can be utilized to garner a lot of information. With different lengths, thicknesses, patterns, and/or orientations, one can measure the length and distances between line fiducials to give scaling, position, orientation of structures such as an operating table utilizing an imaging device such as a camera or fluoroscope.

(8) Magnetic Field Distortion one aspect of looking at EM localization sensor data even in a distorted magnetic field is that even if the field is distorted, the relative distance between two sensors may be configured to remain substantially constant.

Then with a sensor in a magnetic field, one can make more exact calculations of the position of the sensor using knowledge of the behavior of magnetic fields.

(9) Localization and kinematics:

"Adaptive Kinematics"—using localization-based knowledge of where one's instrument is actually located to improve one's kinematic model's ability to place the instrument where one desires to place it:

When we command to a certain position the localization sensor will give us our actual position. In real time we can use a control loop in our control algorithms to minimize the error between our commanded and our actual position.

In one variation localization data may be utilized to update the kinematic model (forward and reverse kinematics) to minimize the error between commanded and actual position. The kinematic behavior is catheter based so this may be done to tune the model per the specific catheter sample, thermal issues, fluid viscosity issues, friction issues, mechanics related to other structures (i.e., what other instruments are placed down the working lumen—their mechanics will vary), etc. Such calibration may be handled on the bench top.

(10) Safety logic and Localization:

If the system is configured to continually use a control loop to minimize the error between commanded and actual position, once the catheter hits tissue or some other structure, the error increases as the catheter presses more and more against such structure. In an effort to minimize the error, the control loop will command the catheter further and further toward the structure.

This challenge may be obviated by creating an updated kinematic model of the pertinent system setup in free space; then when the catheter hits tissue or other structures, the behavior of the catheter will represent the stiffness in the catheter (as opposed to the above scenario where the stiffness of the control loop is represented). This embodiment also ensures that the catheter is driven within a model (within a certain safety threshold).

(11) Preventing pull wire slack:

With a pull-pull type steerable catheter configuration, it is desirable to keep the pull wires in tension for better control. One problem that can occur is that if the physician intentionally presses the catheter against tissue, the controls may command the catheter into a position that it does not hit (because its movement is stopped by the tissue). In such a scenario, the controls may be configured to command the pull wires on one side to pull in tension but command the pull wires on the other side to release slack under the logic that the catheter is moving to a given position, notwithstanding that in such a stuck scenario, the catheter is not moving to such position and does not need the slack to get there. Using localization sensors, the controls will have the actual position of the catheter tip and be configured to not release more slack than needed, retaining the tension in all control wires.

Localization sensors may be used to detect the orientation of the catheter tip, and this information may be used to pre-tension the slack in the pull wires. In other words: look at the position of the catheter tip and tension a pull wire until you see movement.

(12) Localization data pertinent to various images captured by an image capture device may also be utilized to associate the various images relative to each other in space in a mosaic form. For example, the origin location and vector information of an image capture device may be utilized to "stitch" a series of images together in space.

(13) Analogous to the discussion above regarding creating a lookup table and/or transformation matrix for compensating for the magnetic presence and positioning of a structure such as a fluoroscopy C-arm or metal operating table when utilizing electromagnetic localization interoperatively, a lookup table may be created for other structures desirably near the EM field, such as instrument support structures, or even electronics structures, such as RF generators and racks, or electrophysiology intervention systems, such as the Carto system from Biosense Webster.

(14) Micro-transmitters:

Tiny EM localization coils may be placed as micro-transmitters within the heart so that the transmitter is very close to the receiver. Transmitter can be embedded into a guide or sheath instrument, or in a reference catheter.

(15) Reference Measurement:

Transmitters may be used to measure the magnetic field in a metal free environment as a base measurement. Then they may be used to correcting for the introduction of metal associated with structures such as a fluoroscopy C-arm. Transmitter can be, for example, mounted upon a robotic catheter instrument driver.

Can have markers in space (e.g., above patient on a lightweight frame structure) which one may measure during C-arm movement. Then one may use this data to update one's transformations.

(16) Transmitters in one plane:

If we had transmitters that also acted as receivers in the same plane, the transmitter would transmit the signal (ultrasound or RF) which would bounce off a surface and hit a receiver in that plane. When metal is introduced, the signal is distorted and this forms a detecting means.

(17) Transmitters down the length of the sheath:

One may place small EM localization devices down the length of an elongate instrument—in a line, in a spiral configuration about the instrument (to get more variation in magnetic flux capture or signal transmission). In this way, not only are the transmitters spaced fairly closely together but one can also get information of the shape of the sheath along with the absolute position of the catheter tip. The transmitters can ping each other acting as both transmitters and receivers. Somewhat analogous to using kinematics to position a rigid robot with an encoder at each joint. One may go sequentially down the line and put the location together, rather than a single subset of this (which is similar to what one has with transmitters on table and one EM localization coil at instrument tip). With some EM localization systems, one may have three transmitters. In this example, one may use a trio of three to transmit (e.g., all on the sheath distal tip, or all linearly shooting in sequence), then detect with a detecting sensor nearby.

One can use the series of sensors and knowledge of the shape to do metal compensation ala the cage or vest:

Because the position is triangulated using some localization systems, there would be three micro-transmitters positioned orthogonally.

With this idea one can see the difference in error down the length of the catheter and one can correct for the error in real time.

In running a set of three orthogonal sensors down the length, more information can be gathered if the sets are rotated from each other (so that the sets are not identically positioned down the length).

Current use of these magnetic coils is based upon measuring the magnitude of the signal captured by a simple circuit. Each transmitter has a specific signal with a different look. Then a lookup table is created so that position can be determined based on the look and magnitude of the specific signal.

(18) Correcting field issues:

To determine if there is a material that is distorting the magnetic field, one can increase the power of transmission from a sensor. For example, one may transmit and receive a signal and then transmit and receive a signal at a higher power. If the signals look the same, there is no distortion of the magnetic field.

(19) data not being fully utilized in medical EM localization systems:

In one embodiment, phase information or altering frequency is utilized to obtain more data which is not used currently.

Dynamic compensation is another aspect that is not currently being employed. Moving a coil through a magnetic field induces a current. In one embodiment, measuring this current is integrated into the magnetic flux capture analysis to produce a more accurate localization output (i.e., magnetic flux associated with dynamically moving a given sensor circuit loop is compensated for in the analysis of where the given loop is positioned or oriented in space).

(20) developing a transformation matrix to correct for magnetic effects of objects such as C-arms:

Some systems are configured to gather many localization points, then go back and find out what the transformation should have been, and apply that transformation to all of the previously calculated points. In another embodiment, a localized instrument may be driven through a range of motion in which the kinematics is known to be accurate. Points gathered in such range of motion may be utilized to build out a transformation between localization data and actual data based on precise zone of kinematic operation. Having this transformation, the system could then move forward and transform to correct for ferromagnetic effects, etc.

In one embodiment, one can have a structure to support four points in space (the desire being to localize somewhere within that local reference frame defined by the cage). One may know where they are relative to the transmitters underneath the table. For example, maybe they are sensors and one may capture a clean shot (or do biplane localization, etc). Then, bring in the C-arm and everything else to set up a compensation model for the C-arm metal presence and movement—and maybe also the table metal presence and movement.

Configure the cage with points and sensors either sort of around the patient, or under the table.

Identify a local reference frame by placing transmitters below the surgical table and a set of 4 points above the patient in space. One may measure the 4 points and perform a least squares fit to create a reference frame. One may know the position of the 4 points relative to each other and relative to the transmitters to locate the reference frame. Then, any point that falls within that frame, one may now approximate its position within that frame.

Assuming that the kinematics are substantially accurate near the origin (e.g., near the sheath tip), one method is to simply drive the catheter collecting points knowing that the data is substantially accurate. With sensors down the length of the catheter, this is feasible because one may know the orientation of the catheter (with a sensor at only the tip this is a less feasible method). This has the capability of being constantly updated.

So a practical way of completing this is to use the calibration cube described above and let the physician drive around to different parts of the cube. Knowing mathematically how this should look one may be able to infer from the errors what the local bias is.

For even better accuracy, one may place an end effector on the tip of the catheter which has a fixed transformation from the tip of the end effector to the sensor on the catheter then one could touch with the tip of the end effector to obtain a closer approximation to a point.

If one does not use a cage (which is very intrusive), one may put patches on the patient instead. Knowing the location of the patches before the C-arm and fluoro is introduced, then after the C-arm, fluoro are introduced and other objects (e.g., catheters, surgical instruments, etc.) are introduced, one can compare the initial positions of the patches and the subsequent position of the patches, e.g., changed positions. In this case, this accounts for patient motion due to respiration, coughing etc.

If one uses a cage, one can see the cage in fluoro and use this image as well.

(r) other aspects of mixed-modality integration (MR, CT, ultrasound) and navigation:

Having a specialized ultrasound scanning configuration as described above does not inherently obviate the utility CT or MR imaging. For example, in one embodiment, a preoperative CT or MR scan may be acquired as voxel data, segmented, and reconstructed. This may be potentially faster and higher in quality than what can be achieved with ultrasound scans (and probably seed based). The CT or MR scanning may be done by a technician before the cath lab procedure with ample time for processing before then—for example, the day before the procedure.

Given such a preoperative model from CT or MR, and given the software and hardware architecture disclosed above in reference to ultrasound, the following are embodiments of interest:

(1) Run robotic catheter platform based ultrasound scans as described above. Use a voxel based representation of the ultrasound data and a 3-plane user interface for the operator to manipulate the 3-D dataset. Configure the user interface software to allow the operator to select contours and or landmarks which are then used to register to the super high-quality pre-existent CT-based data, as opposed to doing segmentation and reconstruction. This may be faster and produce higher quality models in the end. Also, it may accomplish better registration than the 3 point approach utilized with technologies such as Biosense's Carto. This represents an alternative to conventional techniques for registering CT models, such as those featured in variations of the Carto system.

(2) Perform segmentation and reconstruction with ultrasound as described above for left atrium applications. In one embodiment, one may start by using a completely generic left atrium model. In an alternative embodiment, one may use the pre-operative CT model. In other words, one may start with a patient-personalized left atrium model, as opposed to a generic one. Landmarks could then be located using the shape of the pulmonary veins from the CT scan, or other landmarks, which preferably are fairly well-defined in such data.

(3) Additionally, in another embodiment, if one assume that the position of the pulmonary vein inlets into the left atrium are not going to change much, one may not actually pick the landmarks by hand, but keep them fixed with respect to the rest of the anatomy, i.e. place them in the same location as in the CT model. This would significantly cut down on the overall time to create the model and give us higher quality pulmonary vein modeling.

(4) Build a deformable version of the CT model (i.e., use the nodes in the mesh model as masses, and the lines connecting the nodes as spring+dampers). Use real time ultrasound data to (a) deform the model and (b) register it so that it is closer to what it currently is, i.e. it is a good real time image of reality.

Each of these embodiments above may be somewhat automatically. For each of the above, registration of the model to a working catheter such as that depicted in FIG. 5E or FIG. 5H (404) may be accomplished utilizing localization or other techniques, as described above.

Figure 21:
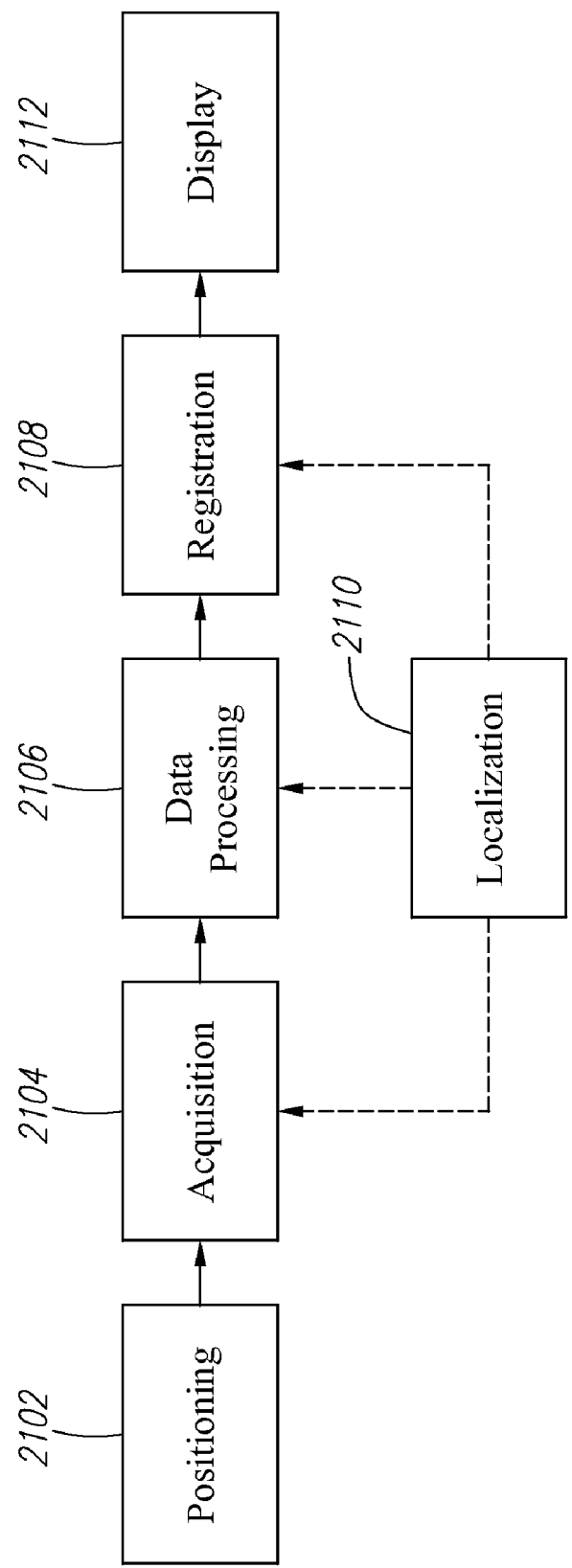
FIG. 21 illustrates a block diagram of the process of producing a three-dimensional map.

FIG. 21 illustrates a block diagram of the process for producing a three-dimensional map of an organ while minimally invasive procedures are being performed. The three-dimensional map would include the instruments that are being used in the organ, e.g., catheters that are being used to perform cardiac ablation in left atrium of a beating heart. The surgeon who is performing the minimally invasive procedures could use the three-dimensional map to determine the relative positions of the catheters in relation to the left atrium that is being operated upon. The process begins, in step 2102, by positioning the ICE catheter in the appropriate location, e.g., the right atrium of the heart, for producing the necessary two-dimensional intracardiac echocardiograms. The ICE catheter may be configured with position, orientation, and shape sensing means (e.g., shape sensing optical fibers, etc.). The acquisition of the two-dimensional intracardiac echocardiogram may be gated by the heart and/or breathing cycles to substantially minimize or eliminate the impact of movement of the heart due to these cycles, wherein the acquisition of intracardiac echocardiogram is taken during the diastolic segment of the heart cycle, in step 2104. The two-dimensional intracardiac echocardiograms are processed by using various filtering methods and algorithms to process a three-dimensional map of the organ that is being operated upon, e.g., the left atrium of the heart, in step 2106. In addition, a registration process is executed to determine the relative position of a robotic catheter that is being used to perform diagnostic and/or interventional procedures in the left atrium, in step 2108. Furthermore, the registration process includes determining the distance of the robotic catheter, e.g., the distal portion of the catheter, to the target site where the diagnostic and/or interventional procedures are being performed. The process of data acquisition, data processing, and registration may be characterized as localization, in step 2110. In other words, the relative positions, locations, distances, etc., for all relevant objects, e.g., tissue walls, robotic catheter, target site, etc., are all determined in this localization phase. As previously described, the spatial relationship of the ICE catheter and robotic catheter within a spatial volume, such as the left atrium, may be determined in the localization phase. An image of a three-dimensional map of the left atrium including the robotic catheter with the localization information is displayed to the surgeon to assist him or her with accurate and precise navigation and placement of robotic catheter for addressing the target site, in step 2112.

Figure 22:
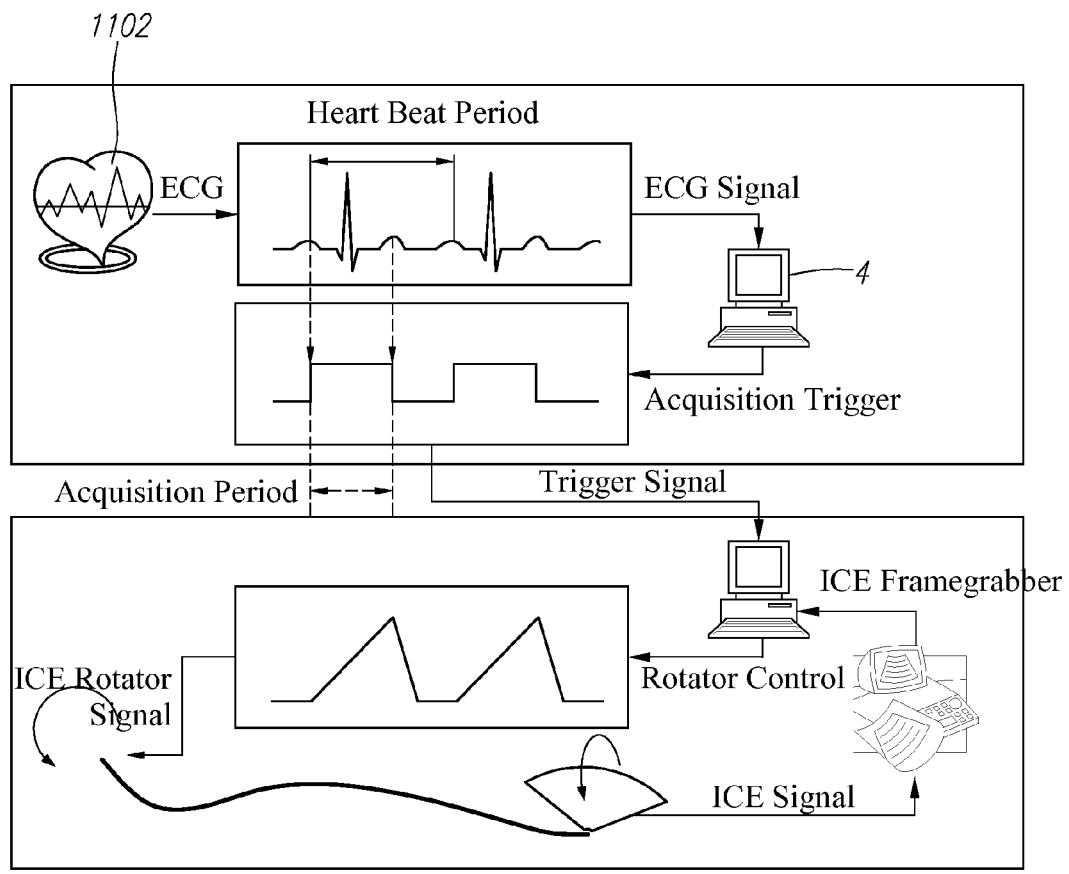
FIG. 22 shows diagrams that illustrate the data acquisition process in a pictorial format.

FIG. 22 shows diagrams that illustrate the data acquisition process in a pictorial format for ease of understanding.

Figure 23:
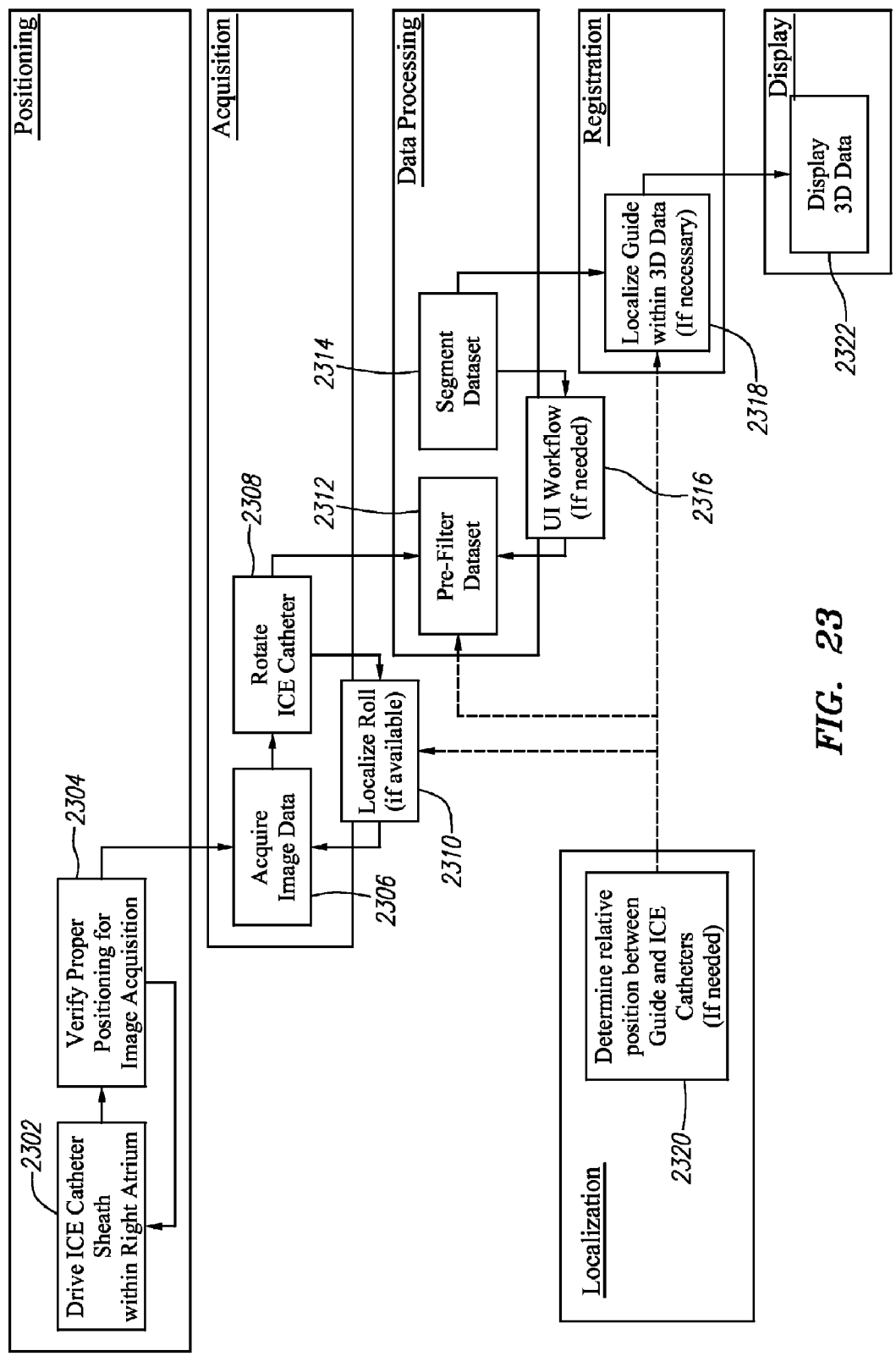
FIG. 23 illustrates a more detailed block diagram for producing a three-dimensional map in accordance with embodiments of the present invention.

FIG. 23 illustrates a more detailed block diagram for producing a three-dimensional map in accordance with embodiments of the present invention. In step 2302, an imaging catheter, e.g., ICE catheter, is advanced into a target volume, e.g., right atrium of the heart of a patient. In step 2304, localization devices identify and verify and the position of the imaging catheter. In step 2306, the imaging catheter transmits image acquisition signals, e.g., ultrasound signals, and acquires information and/or feedback for image data. In the image acquisition phase, the imaging catheter may be rotated to acquire three-dimensional data, in step 2308, to acquire localization data of a working catheter and the guide catheter of the working catheter. Roll localization data for the imaging catheter may be acquired, in step 2310. A pre-filtering process may be performed to the acquired data, i.e., grouping acquired data into pixel volumes or voxels, in step 2312. In step 2314, a segmentation algorithm is performed on the pixel volumes or voxels to produce mesh surfaces of the target volume. The pre-filtering process and/or the segmentation process may be repeated, in step 2316. Localization data from localization sensor or devices coupled to the imaging catheter are processed, in step 2318. Relative position of the imaging catheter and the working catheter (which may include the guide catheter of the working catheter) is determined, in step 2320. A three-dimensional model of the target volume and/or working catheter is display on a user interface, e.g., computer monitor, in step 2322.

While multiple embodiments and variations of the many aspects of the invention have been disclosed and described herein, such disclosure is provided for purposes of illustration only. Many combinations and permutations of the disclosed system, apparatus, and methods are useful in minimally invasive medical diagnosis and intervention, and the invention is configured to be flexible and adaptable. The foregoing illustrated and described embodiments of the invention are suitable for various modifications and alternative forms, and it should be understood that the invention generally, as well as the specific embodiments described herein, are not limited to the particular forms or methods disclosed, but also cover all modifications, alternatives, and equivalents as defined by the scope of the appended claims. Further, the various features and aspects of the illustrated embodiments may be incorporated into other embodiments, even if not so described herein, as will be apparent to those skilled in the art. In addition, although the description describes data being mapped to a three dimensional model, data may be mapped to any mapping or coordinate system, including two dimensional, static or dynamic time-varying map, coordinate system, model, image, etc. All directional references (e.g., upper, lower, upward, downward, left, right, leftward, rightward, top, bottom, above, below, vertical, horizontal, clockwise, counter-clockwise, etc.) are only used for identification purposes to aid the reader's understanding of the invention without introducing limitations as to the position, orientation, or applications of the invention. Joining references (e.g., attached, coupled, connected, and the like) are to be construed broadly and may include intermediate members between a connection of elements (e.g., physically, electrically, optically as by an optically fiber, and/or wirelessly connected) and relative physical movements, electrical signals, optical signals, and/or wireless signals transmitted between elements. Accordingly, joining references do not necessarily infer that two elements are directly connected in fixed relation to each other. It is intended that all matters contained in the description or shown in the accompanying drawings shall be interpreted as illustrative only and not limiting. Modifications, alternatives, and equivalents in the details, structures, or methodologies may be made without departing from the spirit and scope of the invention as defined by the appended claims.

What we claim is:

1. A method for determining a roll orientation of an instrument assembly positioned within a patient, comprising:
    rotating a transducer on a first instrument assembly and emitting a plurality of ultrasound signals in different planes;
    receiving, by a computing system configured to process ultrasound signals, an indication that the plurality of ultrasound signals are being transmitted from the transducer on the first instrument assembly positioned within the patient, and are being received by a transponder on a second instrument assembly positioned within the patient;
    determining, by the computing system, an intensity for each of the plurality of ultrasound signals;

evaluating, by the computing system, the intensity of each of the plurality of ultrasound signals received by the transponder to identify which of the received signals is a direct signal; and determining, by the computing system, a roll orientation of the first instrument assembly relative to the second instrument assembly based on the identified direct signal.

2. The method of claim 1, wherein determining the roll orientation of the first instrument assembly comprises determining a distance between the transducer and the transponder based at least in part on the identified direct signal;

receiving an indication of a transmission line and a transmission plane of the identified direct signal; and determining the roll orientation of the first instrument assembly relative to the second instrument assembly based on the distance between the transducer and the transponder, the transmission line of the identified direct signal, and the transmission plane of the identified direct signal.

3. The method of claim 2, wherein determining the distance between the transducer and the transponder comprises receiving an indication of a response signal being transmitted from the transponder on the second instrument assembly, and received by the transducer on the first instrument assembly;

determining a time-of-flight from the initiation of the identified direct signal to the reception of the response signal by the transducer on the first instrument assembly; and determining the distance between the transducer and the transponder based on the determined time-of-flight.

4. The method of claim 1, wherein evaluating the relative intensities of the plurality of ultrasound signals to identify the direct signal comprises measuring an intensity of each one of the signals; and comparing the measured intensities to a threshold value.

5. The method of claim 1, wherein evaluating the relative intensities of the plurality of ultrasound signals to identify the direct signal comprises producing a graph of the plurality of signals; and using the graph to identify which of the signals is the direct signal.

6. The method of claim 1, wherein the identified direct signal is a signal on a transmission line and a transmission plane that is substantially directed towards the transponder on the second instrument assembly.

7. The method of claim 1, wherein the first and second instrument assemblies respectively comprise first and second robotically-controlled flexible guide catheters, and wherein the method further comprises transmitting electrical signals to the first and second robotically-controlled flexible guide catheters in order to control movement of the first and second robotically-controlled flexible guide catheters.

* * * * *